United States Patent [19]
Dionne et al.

[11] Patent Number: 5,834,001
[45] Date of Patent: Nov. 10, 1998

[54] METHODS FOR MAKING IMMUNOISOLATORY IMPLANTABLE VEHICLES WITH A BIOCOMPATIABLE JACKET AND A BIOCOMPATIBLE MATRIX CORE

[75] Inventors: Keith E. Dionne, Rehoboth, Mass.; Dwaine F. Emerich, Providence, R.I.; Diane Hoffman, Cambridge, Mass.; Paul R. Sanberg, Spring Hill, Fla.; Lisa Christenson, New Haven, Conn.; Orion D. Hegre, Green Valley, Ariz.; David W. Sharp, St. Louis, Mo.; Paul E. Lacy, Webster Grove, Mo.; Patrick Aebischer, Lutry, Switzerland; Alfred V. Vasconcellos, Cranston, R.I.; Michael J. Lysaght, Greenwich, R.I.; Frank T. Gentile, Warwich, R.I.

[73] Assignee: Brown University Research Foundation

[21] Appl. No.: 449,214

[22] Filed: May 24, 1995

Related U.S. Application Data

[60] Division of Ser. No. 179,151, Jan. 10, 1994, which is a continuation-in-part of Ser. No. 692,403, which is a continuation-in-part of PCT/US92/03327 Apr. 22, 1992, abandoned.

[51] Int. Cl.[6] .............................. A61K 9/50; A61K 9/14
[52] U.S. Cl. ..................... 424/422; 424/423; 424/424; 424/426; 424/427; 424/430; 424/434; 424/437; 424/489; 424/490
[58] Field of Search ..................... 424/422, 423, 424/424, 426, 427, 430, 434, 437, 489, 490

[56] References Cited

U.S. PATENT DOCUMENTS 3,093,831  6/1963  Jordan .
3,615,024  10/1971  Michaels .
4,251,387  2/1981  Lim et al. .
4,298,002  11/1981  Ronel .
4,324,683  4/1982  Lim et al. .

(List continued on next page.)

FOREIGN PATENT DOCUMENTS 127989  12/1984  European Pat. Off. .
147939  7/1985  European Pat. Off. .
188309  7/1986  European Pat. Off. .
228067  7/1987  European Pat. Off. .

OTHER PUBLICATIONS

Aebischer et al., *Trans. Am. Soc. Artif. Intern. Organs*, vol. XXXII, pp. 134–137 (1986).
Aebischer et al., *Biol. Abstr.*, 91, p. 762 (1991).
Aebischer et al., *Biomaterials*, 12 pp. 50–56 (1991).
Aebischer et al., *Brain Research*, 560, pp. 43–49 (1991).
Aebischer et al., *Exp. Neurol.*, 111, pp. 269–275 (1991).
Aebischer et al., *J. Biomech. Eng.*, 113, pp. 178–183 (1991).
Aebischer and Goddard, *Science*, 252, p. 133 (1991).
Algire et al. *J. National Cancer Institute*, 15, pp. 493–507 (1954).

(List continued on next page.)

*Primary Examiner*—Raj Bawa
*Attorney, Agent, or Firm*—Ivor Elrifi Mintz, Levin

[57] ABSTRACT

A method of forming an implantable and retrievable immunoisolatory vehicle is disclosed, the method comprising the steps of first forming a jacket of biocompatible thermoplastic or hydrogel, and then loading the jacket with a core comprising a volume of at least 1 $\mu l$ and at least $10^4$ cells capable of secreting a biocompatible matrix comprising a hydrogel or extracellular matrix, said jacket having a molecular weight cutoff permitting passage of molecules thereacross to provide said biologically active product or said function.

25 Claims, 9 Drawing Sheets

U.S. PATENT DOCUMENTS

| | | |
|---|---|---|
| 4,352,883 | 10/1982 | Lim . |
| 4,353,888 | 10/1982 | Sefton . |
| 4,391,909 | 7/1983 | Lim . |
| 4,407,957 | 10/1983 | Lim . |
| 4,409,331 | 10/1983 | Lim . |
| 4,479,796 | 10/1984 | Kallok . |
| 4,663,286 | 5/1987 | Tsang et al. . |
| 4,670,014 | 6/1987 | Huc . |
| 4,686,098 | 8/1987 | Kopchick . |
| 4,689,293 | 8/1987 | Goosen . |
| 4,749,620 | 6/1988 | Rha . |
| 4,789,550 | 12/1988 | Hommel . |
| 4,806,355 | 2/1989 | Goosen . |
| 4,868,121 | 9/1989 | Scharp . |
| 4,883,666 | 11/1989 | Sabel . |
| 4,892,538 | 1/1990 | Aebischer . |
| 4,902,295 | 2/1990 | Walthall . |
| 4,942,129 | 7/1990 | Goosen . |
| 4,960,415 | 10/1990 | Reinmuller . |
| 5,002,661 | 3/1991 | Chick . |
| 5,026,365 | 6/1991 | Rossini . |
| 5,082,670 | 1/1992 | Gage . |
| 5,084,350 | 1/1992 | Chang . |
| 5,106,627 | 4/1992 | Aebischer . |
| 5,156,844 | 10/1992 | Aebischer . |
| 5,158,881 | 10/1992 | Aebischer et al. . |
| 5,283,187 | 2/1994 | Aebischer et al. . |
| 5,284,761 | 2/1994 | Aebischer et al. . |
| 5,292,515 | 3/1994 | Moro . |
| 5,389,535 | 2/1995 | Aebischer et al. . |

FOREIGN PATENT DOCUMENTS

| | | |
|---|---|---|
| 2 094 750 | 9/1982 | United Kingdom . |
| 2 094 832 | 9/1982 | United Kingdom . |
| 2 094 833 | 9/1982 | United Kingdom . |
| 2192171 | 1/1988 | United Kingdom . |
| 84/01287 | 4/1984 | WIPO . |
| 87/03802 | 7/1987 | WIPO . |
| 87/04367 | 7/1987 | WIPO . |
| 88/00237 | 1/1988 | WIPO . |
| 88/10103 | 12/1988 | WIPO . |
| 89/04655 | 6/1989 | WIPO . |
| 90/02580 | 3/1990 | WIPO . |
| 90/05552 | 5/1990 | WIPO . |
| 90/15637 | 12/1990 | WIPO . |
| 91/00119 | 1/1991 | WIPO . |
| 91/07951 | 6/1991 | WIPO . |
| 91/09119 | 6/1991 | WIPO . |
| 91/10425 | 7/1991 | WIPO . |
| 91/10470 | 7/1991 | WIPO . |
| 92/07525 | 5/1992 | WIPO . |
| 93/00063 | 1/1993 | WIPO . |
| 93/00127 | 1/1993 | WIPO . |
| 93/00128 | 1/1993 | WIPO . |
| 93/00439 | 1/1993 | WIPO . |
| 93/03901 | 3/1993 | WIPO . |
| 93/21902 | 11/1993 | WIPO . |
| 93/22427 | 11/1993 | WIPO . |

OTHER PUBLICATIONS

Altman et al., *Trans. Am. Soc. Artif. Intern. Organs*, vol. XXX, pp. 382–386 (1984).
Altman et al., *Diabetes*, 35, pp. 625–633 (1986).
Amicon Corp. Publication No. 442C, pp. 1–4.
Archer et al., *J. Surgical Research*, 28, pp. 77–85 (1980).
Bontempo et al., *Blood*, 69, pp. 1721–1724 (1987).
Brandrup et al., *Polymer Handbook* 3rd Ed., John Wiley & Sons, N.Y. (1989).
Britt et al., *Diabetes*, 30, pp. 580–583 (1981).
Cabasso, *Encyclopedia of Chemical Technology*, Kirk Othmer, ed., Wiley, NY, 12, pp. 492–517 (1980).
Cai et al., *Artificial Organs*, 12, pp. 388–393 (1988).
Cepko, *Neuron*, 1, pp. 345–353 (1988).
Christenson et al., *J. Biomed. Mat. Res.*, 23, pp. 705–718 (1989).
Christenson, Ph.D. Thesis, Brown University (1990).
Cohen et al., *J. Am. Chem. Soc.*, 112, pp. 7832–7833 (1990).
Cole et al., *Diabetologia*, 35, pp. 231–237 (1992).
Darquy et al., *Diabetologia*, 28, pp. 776–780 (1985).
Darquy et al., *Trans. Am. Soc. Artif. Intern. Organs*, vol. XXXIII, pp. 356–358 (1987).
Dionne, Thesis Ph.D., Massachusetts Institute of Technology, pp. 170–184 (1989).
Dupuy et al., *J. Biomed. Mat. Res.*, 22, pp. 1061–1070 (1988).
Edmunds et al., *Applied Biochemistry and Biotechnology*, 20–21, pp. 603–619 (1989).
Faithfull, *Anaesthesia*, 42, pp. 234–242 (1987).
Fan et al., *Diabetes*, 39, pp. 519–522 (1990).
Fu et al., *Transplantation*, 47, pp. 432–435 (1989).
Gordon et al., *Nature*, 326, pp. 403–405 (1987).
Hama et al., *Pain*, 52, pp. 223–231 (1993).
Hoffman et al., *Exp.Neurol.*, 110, pp. 39–44 (1990).
Hong et al., *Int. J. Radiation Oncology Biol. Phys.* 16, pp. 1097–1099 (1989).
Iwata et al., *Diabetes*, 38, pp. 224–225 (1989).
Jaeger et al., *Progress in Brain Research*, 82, pp. 41–46, Elsevier Science Publishers B.V. (1990).
Jaeger et al., *Brain Research*, 551, pp. 163–170 (1991).
Jarret et al., *The Lancet*, 2, pp. 1009–1012 (1976).
Jolley et al., *Transplantation Proceedings*, IX, pp. 363–365 (1977).
Klomp et al., *Journal of Biomedical Materials Research*, 17, pp. 865–871 (1983).
Lacy et al., *Science*, 204, pp. 312–313 (1979).
Lacy et al., *Science*, 254, pp. 1782–1784 (1991).
Land et al., *Nature*, 304, pp. 596–602 (1983).
Leung et al., *Artificial Organs*, 7, pp. 208–212 (1983).
Lim et al., *Science*, 210, pp. 908–910 (1980).
Livett, *Physiology Reviews*, 64, pp. 1103–1161 (1984).
Maniats et al., *Can J. Comp. Med.*, 42, pp. 428–437 (1978).
Matthews et al., *Recent Advances in Germfree Research*, Tokai University Press, pp. 61–64 (1981).
NASA Tech. Briefs MSC–21480, U.S. Gov't. Printing Office, Washington, D.C.
NASA Tech. Briefs NPO–17517, vol. 15 #1 p. 54, U.S. Gov't. Printing Office, Washington, D.C.
Sun et al., *Applied Biochem. Biotechnol.*, 10, pp. 87–99 (1984).
O'Shea et al., *Diabetes*, 35, pp. 943–946 (1986).
Reach, *Biomed. Biochim. Acta*, 43, pp. 569–576 (1984).
Ricordi et al., *Transplantation*, 45, pp. 1148–1151 (1988).
Ronel et al., *Journal of Biomedical Materials Research*, 17, pp. 855–864 (1983).
Sagen et al., *Proc. Natl. Acad. Sci. USA*, 83, pp. 7522–7526 (1986).
Sagen et al., *Pain*, 42, pp. 69–79 (1990).
Sagen et al., *J. Neuroscience*, 13, pp. 2415–2423 (1993).
Sanberg et al., *Exp. Neurol.*, 66, pp. 444–466 (1979).
Scharp et al., *World J. Surg.*, 8, pp. 221–229 (1984).
Sefton et al., *Biotech. and Bioeng.*, XXIX, pp. 1135–1143 (1987).
Short et al., *Dev. Neurosci.*, 12, pp. 34–45 (1990).

Soeldner et al., *Diabetes,* 14, pp. 771–779 (1965).
Sugamori et al., *Trans. Am. Soc. Artif. Intern. Organs,* XXXV, pp. 791–799 (1989).
Sun et al., *Diabetes,* 26, pp. 1136–1139 (1977).
Sun et al., *Trans. Am. Soc. Artif. Intern. Organs,* XXXII, pp. 39–41 (1986).
Sun et al., *Biomat., Art. Cells, Art. Org.,* 15, pp. 483–496 (1987).
Sun et al., *CRC Critical Reviews in Therapeutic Drug Carrier Systems,* 4, pp. 1–12 (1987).
Sun, *Trans. Am. Soc. Artif. Intern. Organs,* XXXIII, pp. 787–790
Sun, *Methods in Enzymology,* 137, pp. 575–580 (1988).
Tresco et al., *ASAIO Journal,* 38, pp. 17–23 (1992).
Tze et al., *Nature,* 264, pp. 466–467 (1976).
Tze et al., *Diabetologia,* pp. 247–252 (1979).
Tze et al., *Transplantation,* 33, pp. 563–564 (1982).
Weber et al., *Transplantation,* 49, pp. 396–404 (1990).
Will et al., *Behav. Brain Res.,* 17, pp. 17–24 (1985).
Wilson et al., *J. Biol. Chem.,* 263, pp. 2712–2718 (1988).
Winn et al., *Exp. Neurol.,* 105, pp. 244–250 (1989).
Winn et al., *J. Biomed. Materials Res.,* 23, pp. 31–44 (1989).
Winn et al., *Exp. Neurol.,* 113, pp. 322–329 (1991).
Winnie et al., *Anesthesiology,* 79, pp. 644–653 (1993).
Wu et al., *Int'l. Jour. Pancreatology,* 3, pp. 91–100 (1988).
Wu et al., *Trans. Am. Soc. Artif. Intern. Organs,* XXXV, pp. 736–738 (1989).

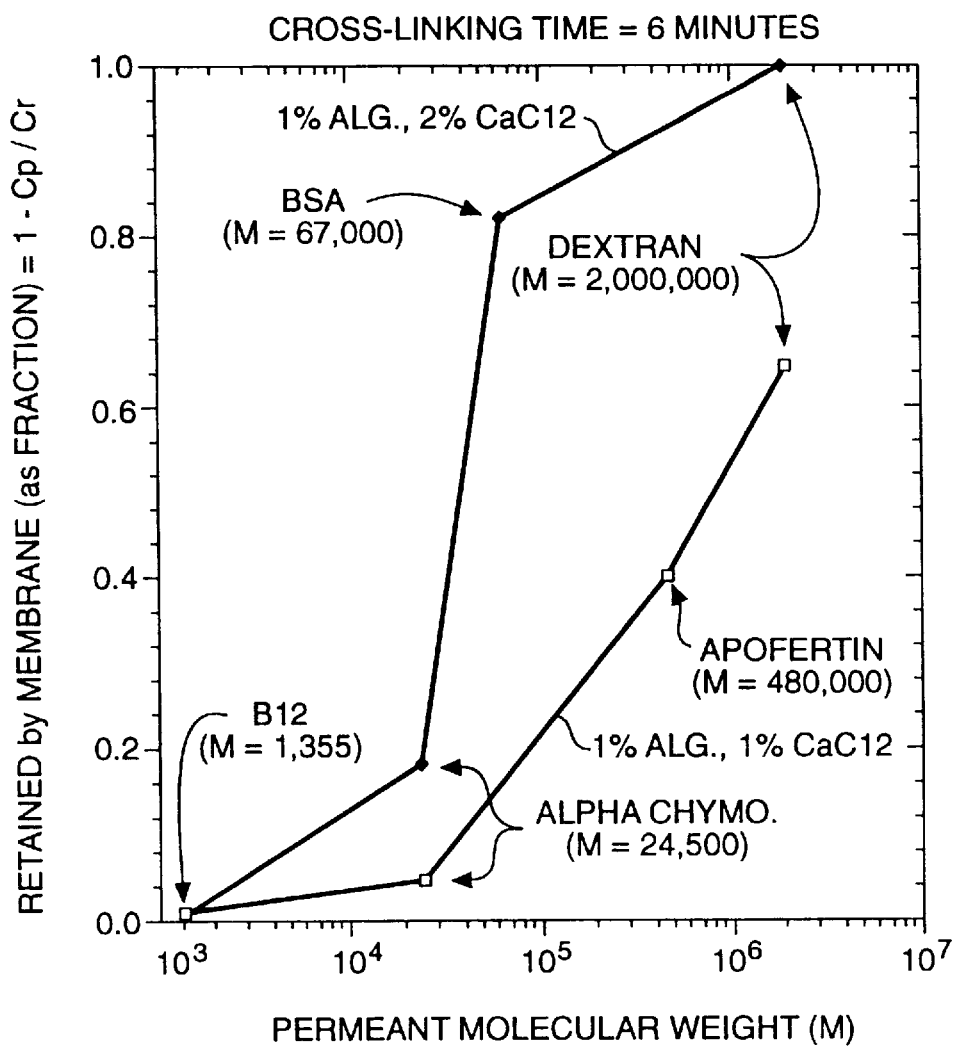
FIG._1

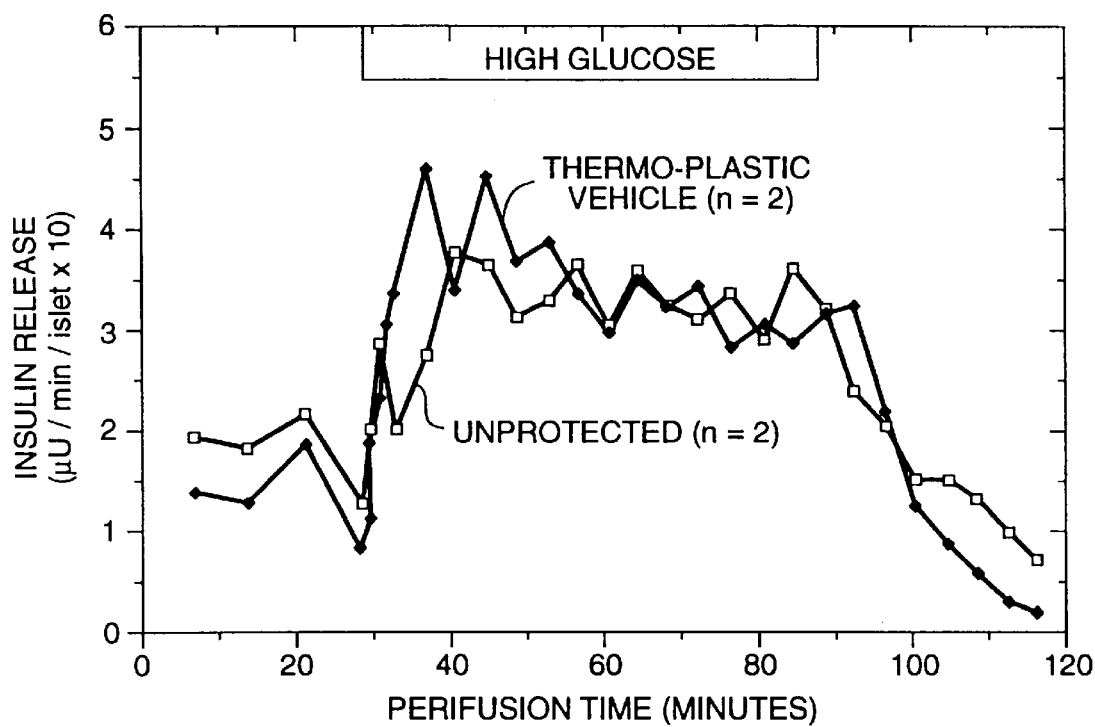
FIG._2A
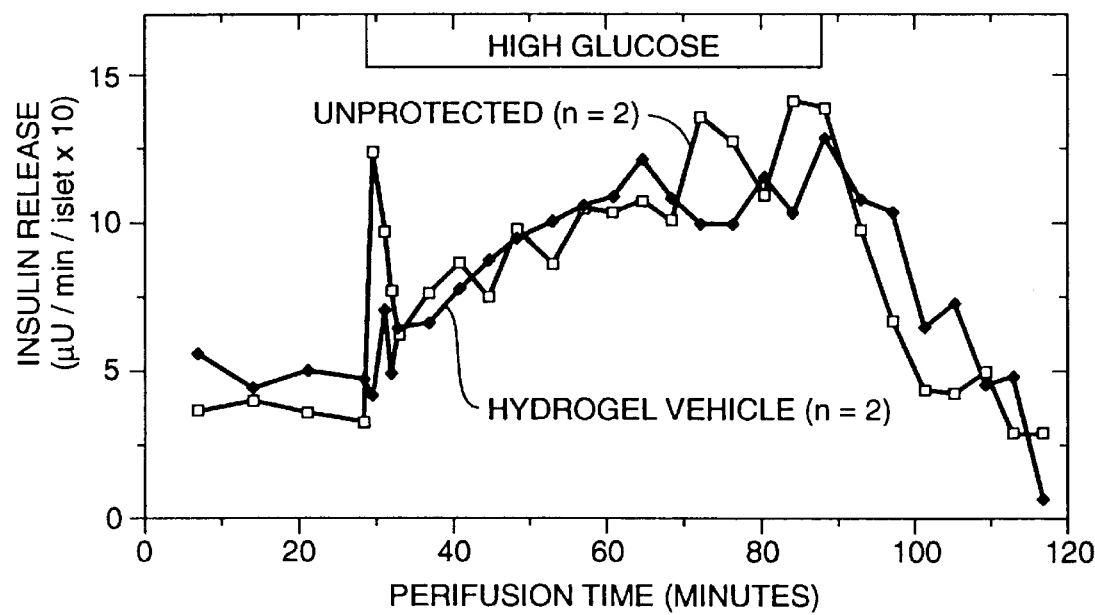
FIG._2B

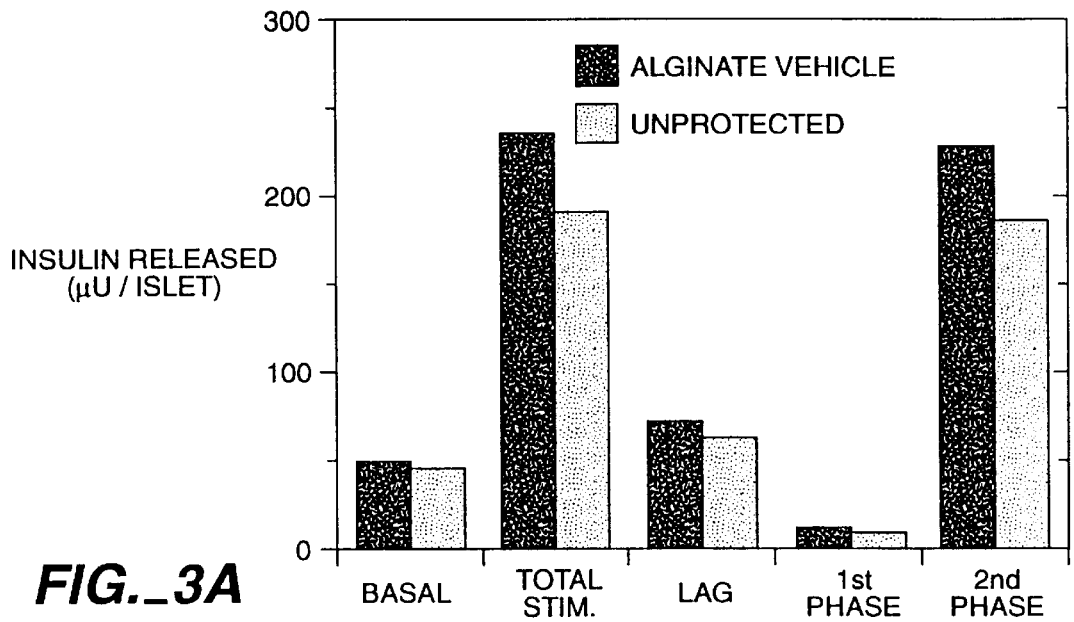
FIG._3A
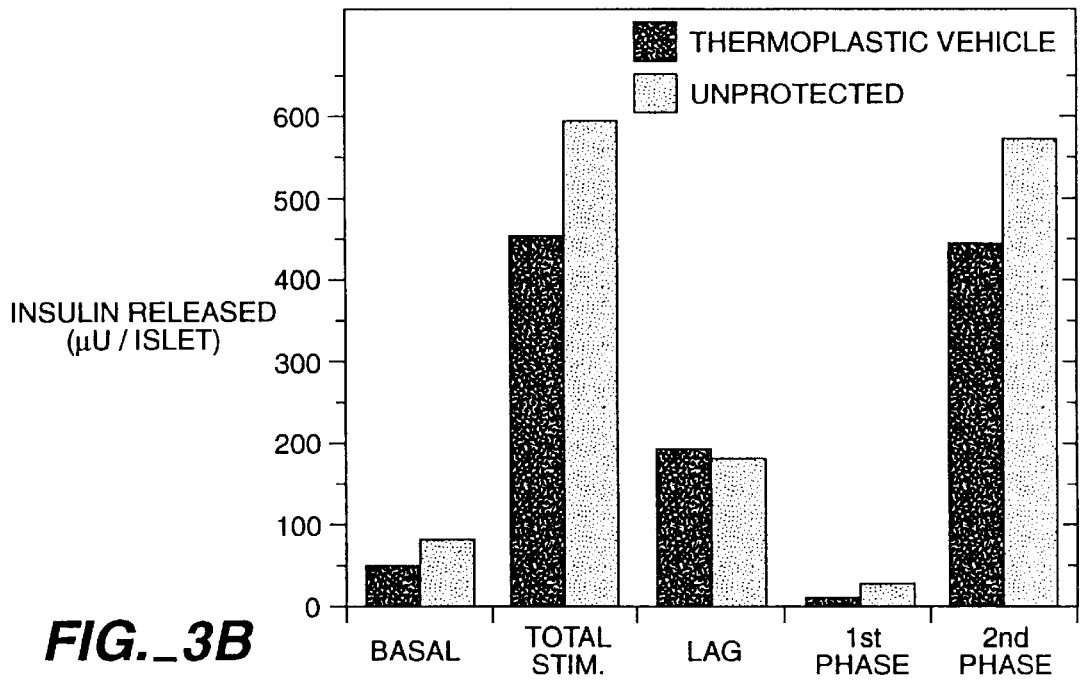
FIG._3B

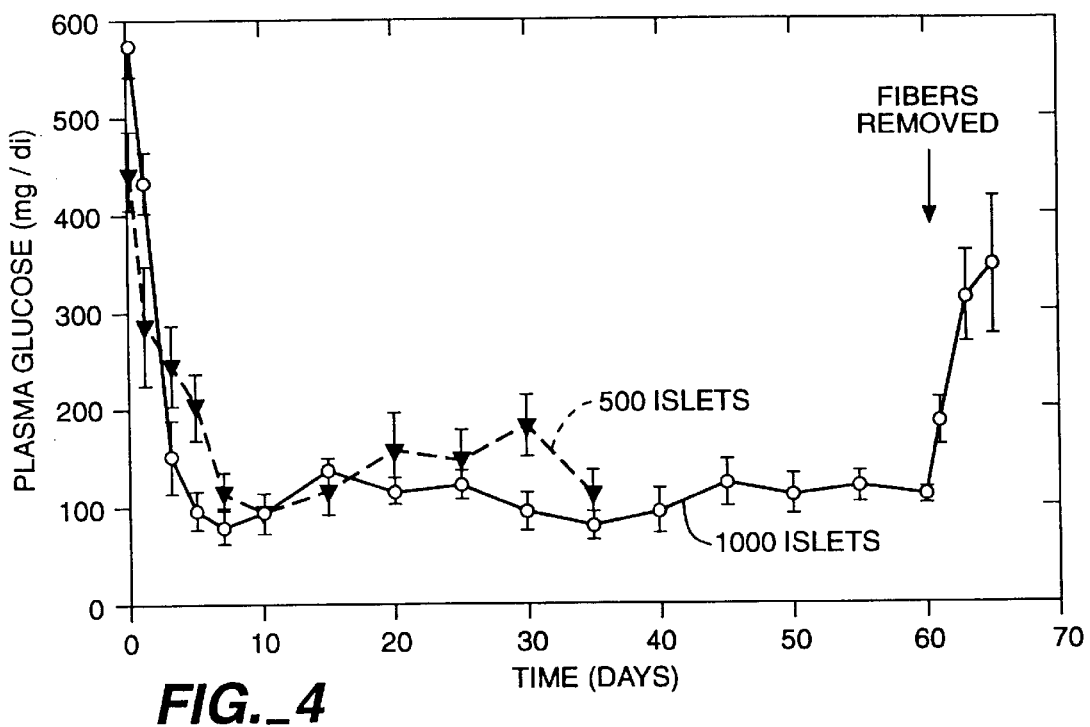
FIG._4
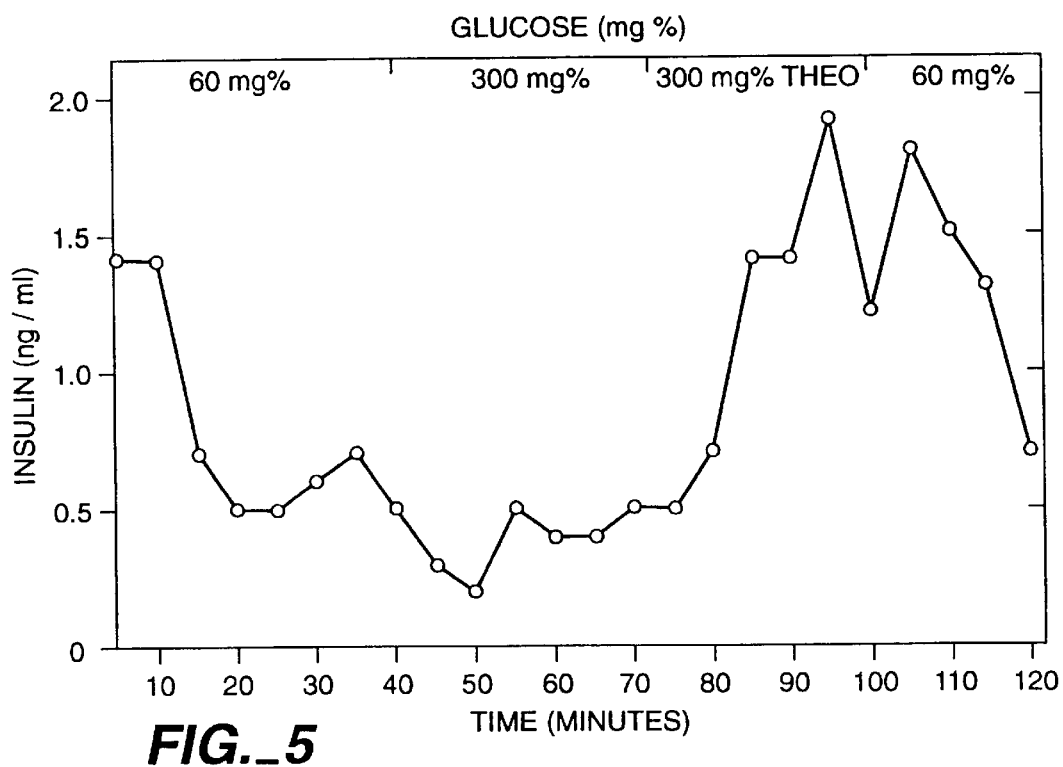
FIG._5

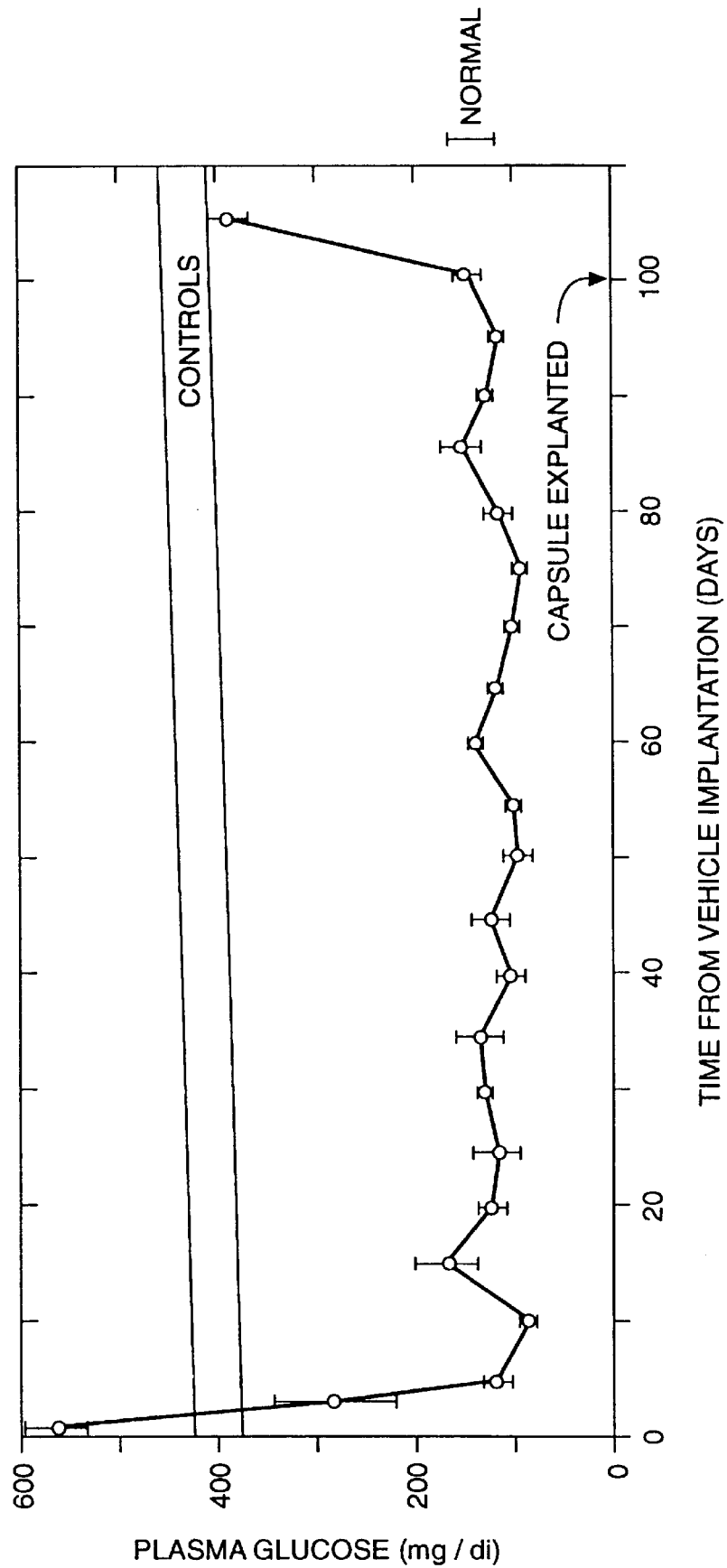
FIG._6

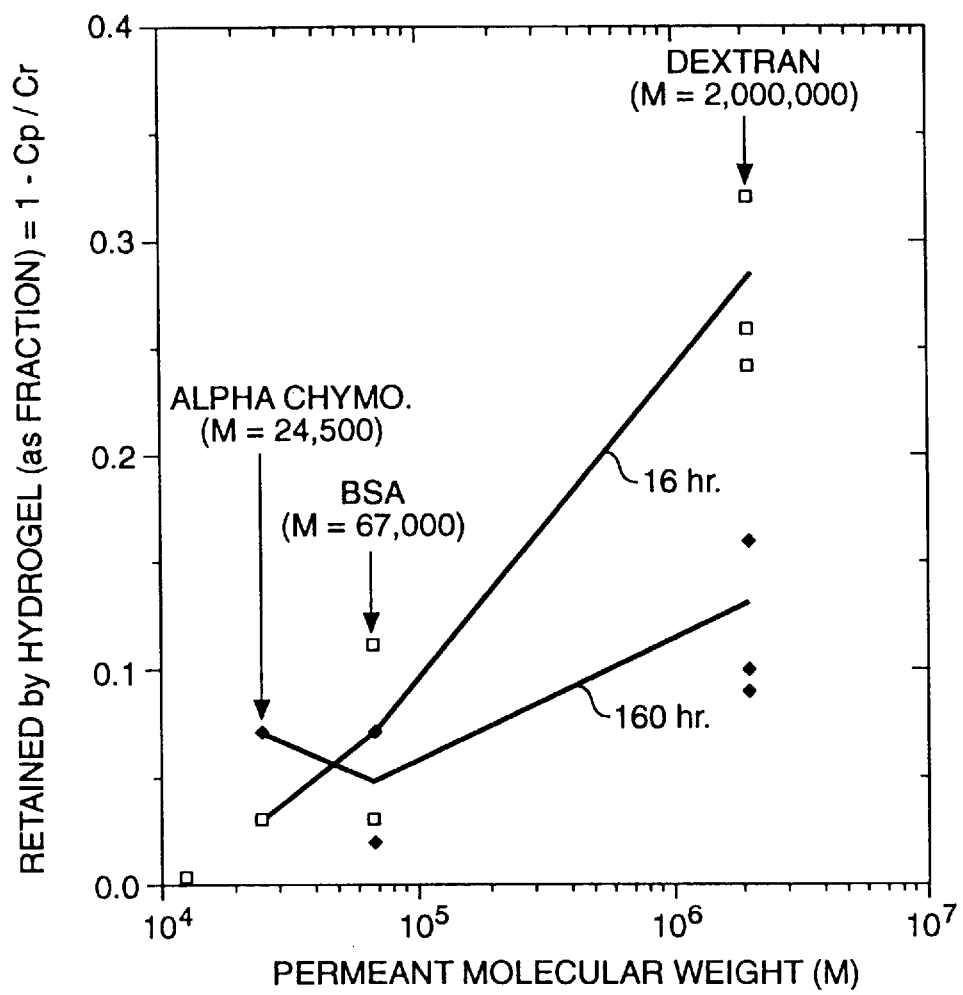
FIG._7

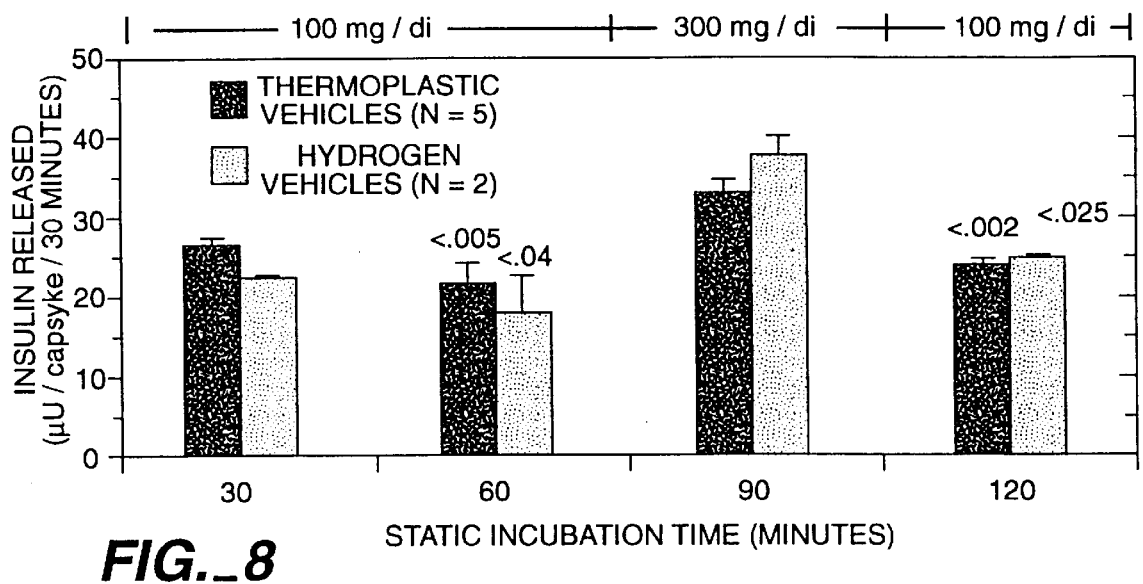
FIG._8
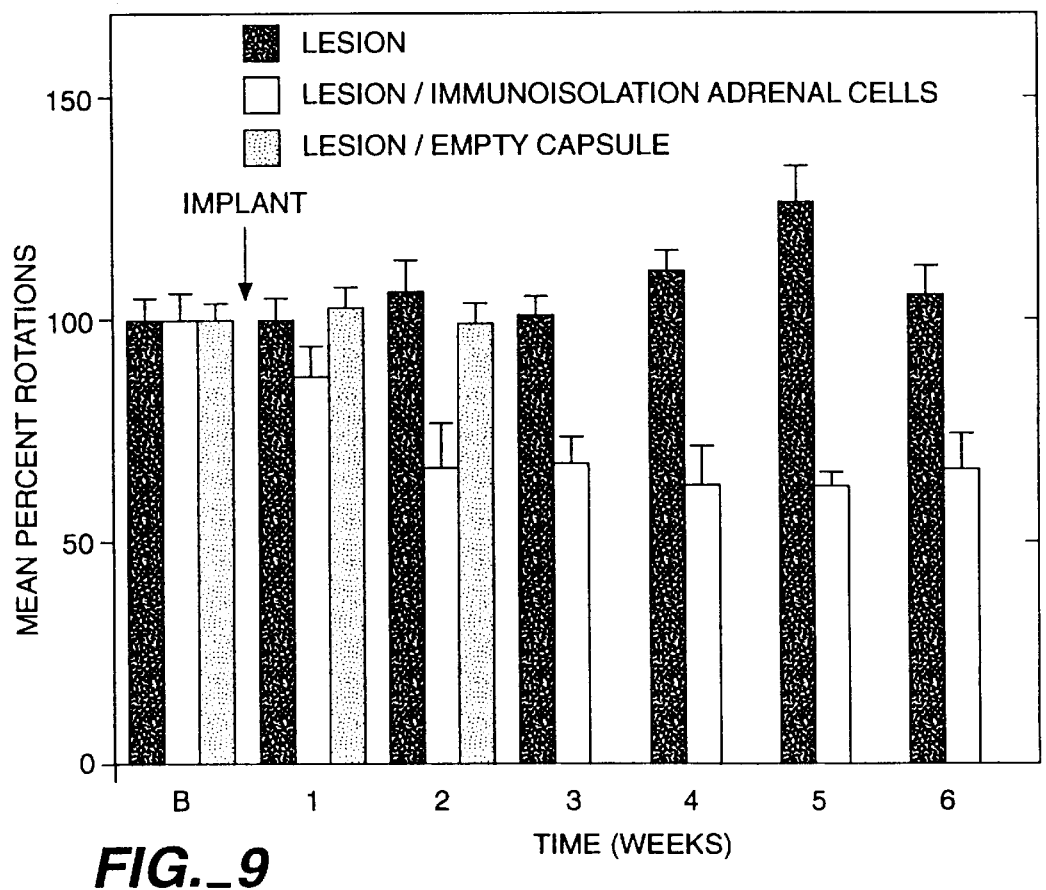
FIG._9

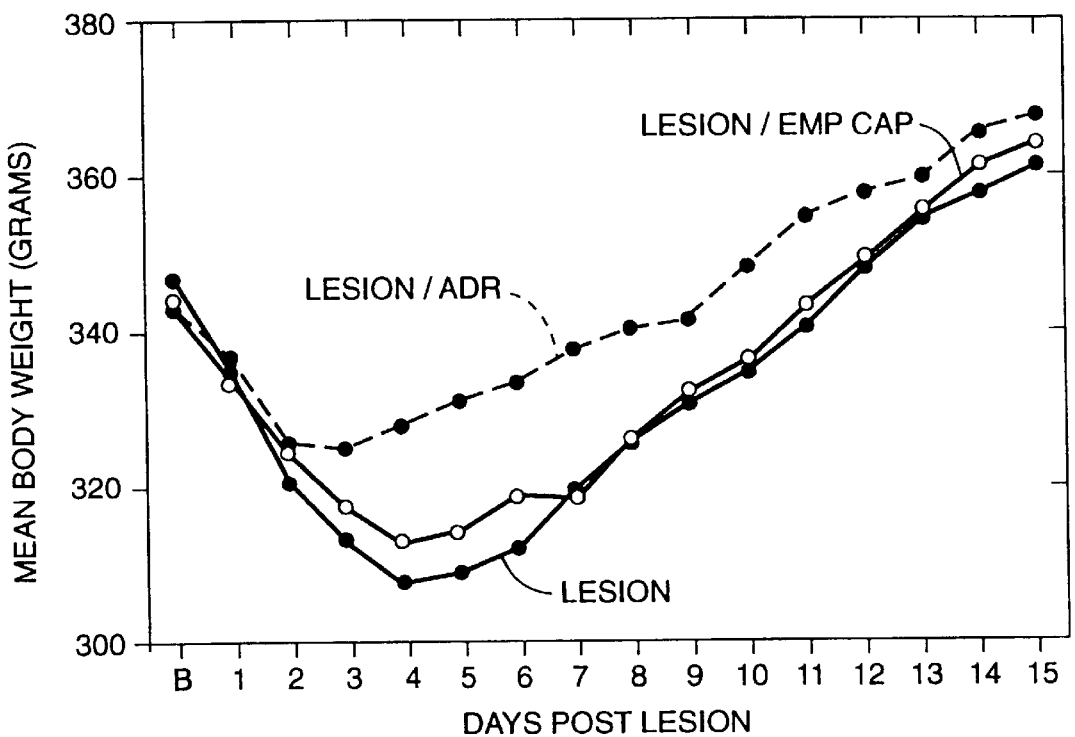
FIG._10
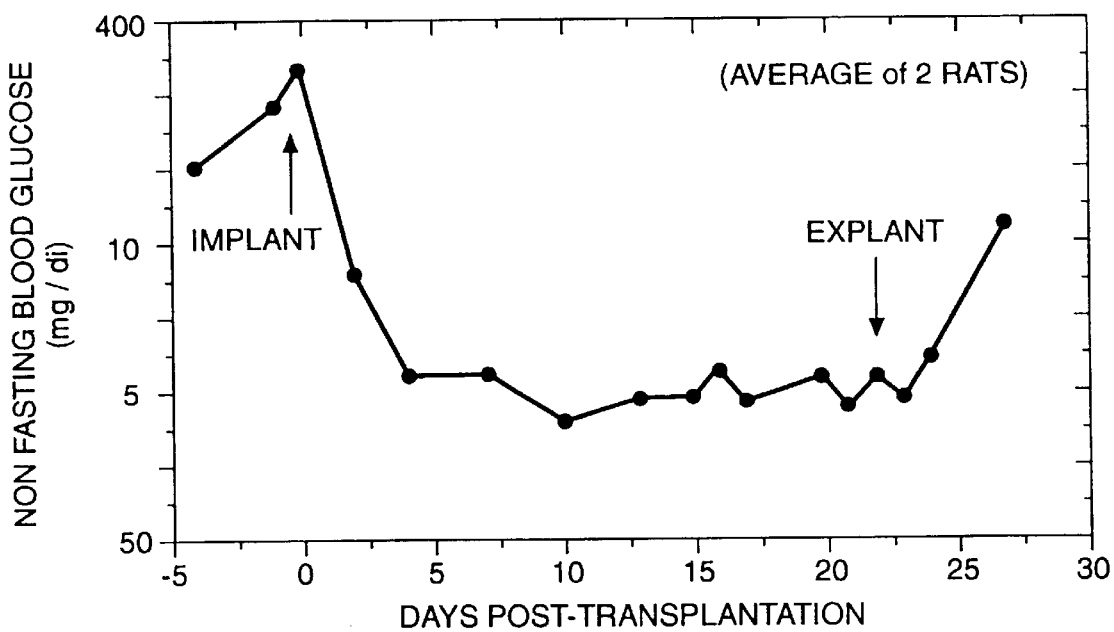
FIG._12

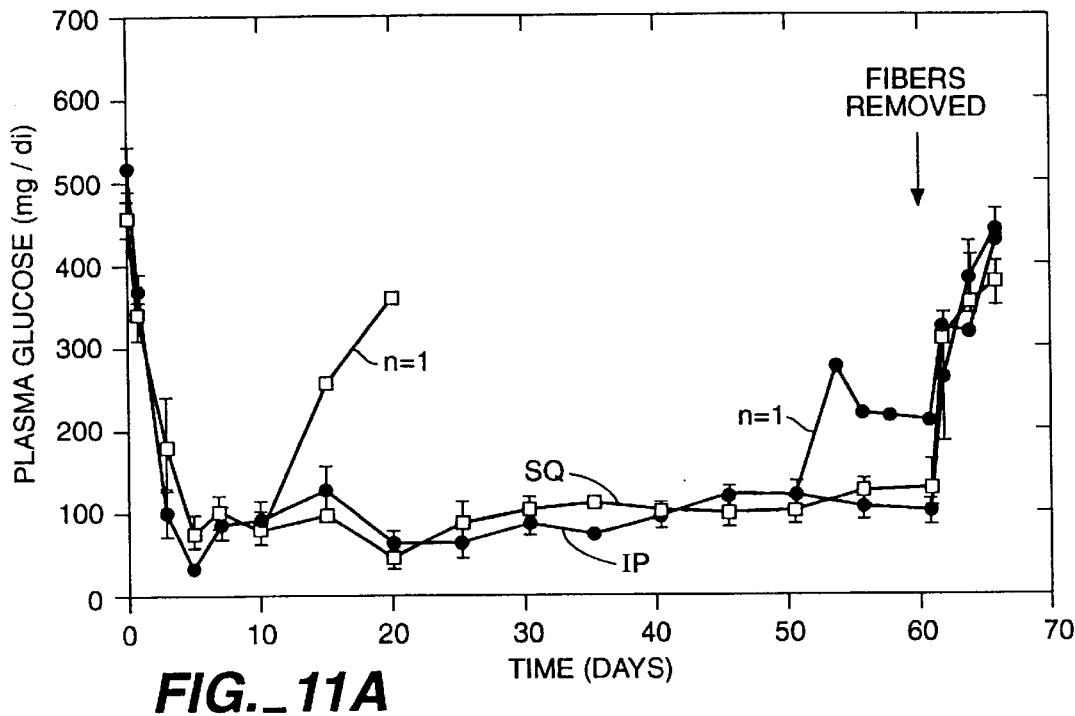
FIG._11A
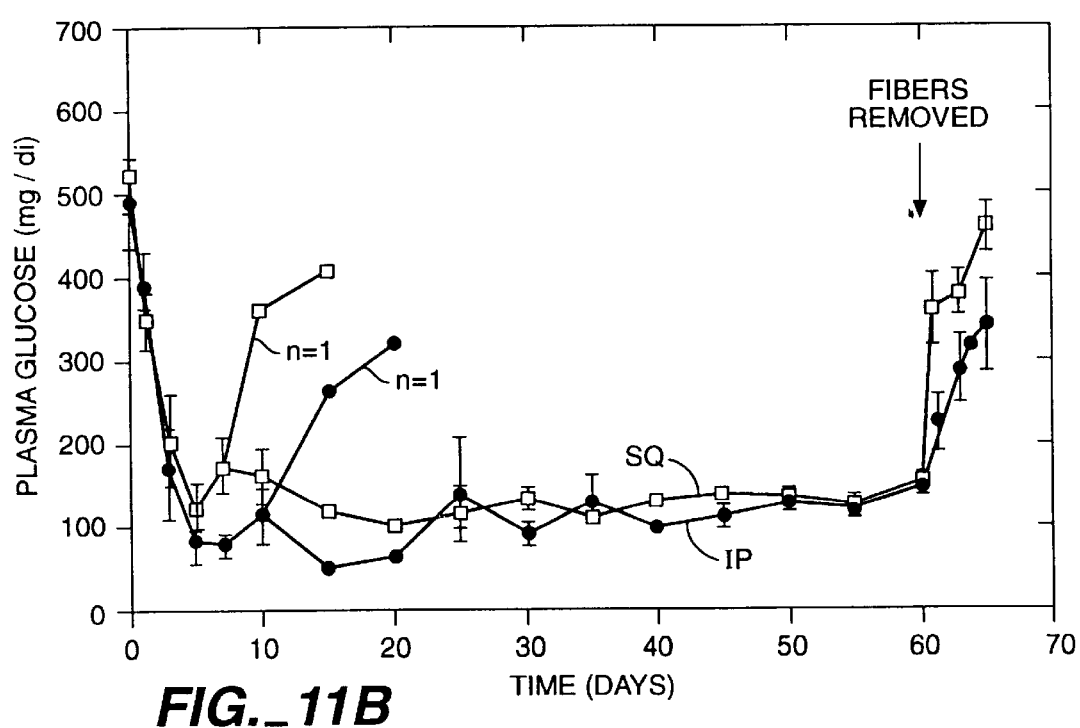
FIG._11B

METHODS FOR MAKING IMMUNOISOLATORY IMPLANTABLE VEHICLES WITH A BIOCOMPATIABLE JACKET AND A BIOCOMPATIBLE MATRIX CORE

RELATED APPLICATIONS

This is a division of Ser. No. 08/179,151, filed Jan. 10, 1994, which is a continuation-in-part application of PCT application serial No. US 92/03327, filed April 22, 1992, which is a continuation-in-part of application Serial No. 07/692,403, filed April 25, 1991, now abandoned.

BACKGROUND

Many clinical conditions, deficiencies, and disease states can be remedied or alleviated by supplying to the patient a one or more biologically active moieties produced by living cells or removing from the patient deleterious factors which are metabolized by living cells. In many cases, these moieties can restore or compensate for the impairment or loss of organ or tissue function. Examples of disease or deficiency states whose etiologies include loss of secretory organ or tissue function include (a) diabetes, wherein the production of insulin by pancreatic islets of Langerhans is impaired or lost; (b) hypoparathyroidism, wherein the loss of production of parathyroid hormone causes serum calcium levels to drop, resulting in severe muscular tetany; (c) Parkinsonism, wherein dopamine production is diminished; and (d) anemia, which is characterized by the loss of production of red blood cells secondary to a deficiency in erythropoietin. The impairment or loss of organ or tissue function may result in the loss of additional metabolic functions. For example, in fulminant hepatic failure, liver tissue is rendered incapable of removing toxins, excreting the products of cell metabolism, and secreting essential products, such as albumin and Factor VIII. Bontempo, F. A., et al., *Blood*, 69, pp. 1721–1724 (1987).

In other cases, these biologically active moieties are biological response modifiers, such as lymphokines or cytokines, which enhance the patient's immune system or act as anti-inflammatory agents. These can be particularly useful in individuals with a chronic parasitic or infectious disease, and may also be useful for the treatment of certain cancers. It may also be desirable to supply trophic factors to a patient, such as nerve growth factor or insulin-like growth factor-one or -two (IGF1 or IGF2).

In still other cases, the biologically active moiety can be a secretory substance, such as a neurotransmitter, neuromodulator, hormone, trophic factor, or growth factor, or a neuroactive substance for the reduction of pain sensitivity. Such neuroactive substances include catecholamines, enkephalins, and opioid peptides.

In many disease or deficiency states, the affected organ or tissue is one which normally functions in a manner responsive to fluctuations in the levels of specific metabolites, thereby maintaining homeostasis. For example, the parathyroid gland normally modulates production of parathyroid hormone (PTH) in response to fluctuations in serum calcium. Similarly, B cells in the pancreatic islets of Langerhans normally modulate production of insulin in response to fluctuations in serum glucose. Traditional therapeutic approaches to the treatment of such diseases cannot compensate for the responsiveness of the normal tissue to these fluctuations. For example, an accepted treatment for diabetes includes daily injections of insulin. This regimen cannot compensate for the rapid, transient fluctuations in serum glucose levels produced by, for example, strenuous exercise. Failure to provide such compensation may lead to complications of the disease state; this is particularly true in diabetes. Jarret, R. J. and Keen J., (1976) *Lancet*(2):1009–1012.

Many other diseases are, likewise, characterized by a deficiency in a biologically active moiety that cannot easily be supplemented by injections or longer-term, controlled release therapies. Still other diseases, while not characterized by substance deficiencies, can be treated with biologically active moieties normally made and secreted by cells. Thus, trophic and growth factors may be used to prevent neurodegenerative conditions, such as Huntington's and Alzheimer's diseases, and adrenal chromaffin cells which secrete catecholamines and enkephalins, may be used to treat pain.

It is also fairly well established that the activation of noradrenergic or opioid receptors in the spinal cord by direct intrathecal injection of $\alpha$-adrenergic or opioid agonists produces antinociception, and that the co-administration of subeffective doses of these agents can produce potent analgesia. The presence of enkephalin-secreting neurons and opiate receptors in high densities in the substantia gelatinosa of the spinal cord and the resultant analgesia observed following local injection of opiates into the spinal cord have suggested a role for opioid peptides in modulating the central transmission of nociceptive information. In addition, catecholamines also appear to be important in modulating pain sensitivity in the spinal cord since injection of noradrenergic agonists into the subarachnoidal space of the spinal cord produces analgesia, while the injection of noradrenergic antagonists produces increased sensitivity to noxious stimuli.

Many drugs have been administered intraspinally in the clinical setting, and numerous methods are available to deliver intraspinal medications. For instance, the most common method of intraspinal drug delivery, particularly anesthetics, is continuous infusion by way of spinal catheters. However, the use of these catheters, particularly small-bore catheters, has been implicated in such complications as cauda equina syndrome, a neurological syndrome characterized by loss of sensation or mobility of the lower limbs. In fact, the FDA was prompted to issue a safety alert in May, 1992, alerting Anesthesia Care Providers to the serious hazard associated with continuous spinal anesthesia by small-bore catheters and has taken action to remove all small-bore catheters from the market.

Accordingly, many investigators have attempted to reconstitute organ or tissue function by transplanting whole organs, organ tissue, or cells which provide secreted products or affect metabolic functions. Moreover, transplantation can provide dramatic benefits but is limited in its application by the relatively small number of organs suitable and available for grafting. In general, the patient must be immunosuppressed in order to avert immunological, rejection of the transplant, which results in loss of transplant function and eventual necrosis of the transplanted tissue or cells. In many cases, the transplant must remain functional for a long period of time, even for the remainder of the patient's lifetime. It is both undesirable and expensive to maintain a patient in an immunosuppressed state for a substantial period of time.

A desirable alternative to such transplantation procedures is the implantation of cells or tissues within a physical barrier which will allow diffusion of nutrients, waste materials, and secreted products, but block the cellular and molecular effectors of immunological rejection. A variety of devices which protect tissues or cells producing a selected product from the immune system have been explored. These include extravascular diffusion chambers, intravascular diffusion chambers, intravascular ultrafiltration chambers, and implantation of microencapsulated cells. Scharp, D. W., et al., *World J. Surg.*, 8, pp. 221–9 (1984)2. These devices would alleviate the need to maintain the patient in an immunosuppressed state. However, none of these approaches have been satisfactory for providing long-term transplant function. A method of delivering appropriate quantities of needed substances, such as enzymes, hormones, or other factors or, providing other needed metabolic functions, for an extended period of time is still unavailable and would be very advantageous to those in need of long-term treatment.

SUMMARY OF THE INVENTION

This invention relates to a biocompatible, immunoisolatory, implantable vehicle. The instant vehicle is suitable for isolating biologically active cells or substances from the body's protective mechanisms following implantation into an individual. The instant vehicle is comprised of (a) a core which contains isolated cells, either suspended in a liquid medium or immobilized within a hydrogel matrix, and (b) a surrounding or peripheral region ("jacket") of permselective matrix or membrane which does not contain isolated cells, which is biocompatible, and which is sufficient to protect the isolated cells in the core from immunological attack.

The immunoisolatory vehicle is useful (a) to deliver a wide range of biologically active moieties, including high molecular weight products, to an individual in need of them, and/or (b) to provide needed metabolic functions to an individual, such as the removal of harmful substances. The instant vehicle contains a multiplicity of cells, such that implantation of a few or a single vehicle is sufficient to provide an effective amount of the needed substance or function to an individual. A further advantage offered by the instant vehicle is practicality of retrieval.

In one embodiment of the invention, which is particularly useful with islets of Langerhans, both the core and the surrounding or peripheral region of the instant vehicle are hydrogels, which can be the same composition hydrogel or different composition hydrogels.

This invention also relates to a method of delivering a biologically active moiety or altering a metabolic or immunologic function in an individual in need of the moiety or altered metabolic function. An immunoisolatory vehicle of the present invention is implanted into the individual (referred to as the recipient), using known techniques or methods and selected for the particular immunoisolatory vehicle and site of implantation. Once implanted, cells isolated within the biocompatible immunoisolatory vehicle produce the desired moieties or perform the desired function (s). If moieties are released by the isolated cells, they pass through the surrounding or peripheral permselective membrane or hydrogel matrix into the recipient's body. If metabolic functions are provided by the isolated cells, the substances to be metabolized (e.g., degraded or inactivated) enter the vehicle from the recipient's body and are removed from the recipient's bloodstream.

Thus, this invention relates to a method of isolating cells within a biocompatible, immunoisolatory implantable vehicle, thereby protecting the cells within the vehicle from immunological attack after being implanted into an individual. Although some low molecular weight mediators of the immune responses (e.g. cytokines) may be permeable to the membrane, in most cases local or circulating levels of these substances are not high enough to have detrimental effects. The isolated cells are protected from attack by the recipient's immune system and from potentially deleterious inflammatory responses from the tissues which surround the implanted vehicle. In the core of the vehicle, the isolated cells are maintained in a suitable local environment. In this manner, needed substances or metabolic functions can be delivered to the recipient even for extended periods of time, and without the need to treat the recipient with dangerous immunosuppressive drugs.

This invention relates further to a method of making a biocompatible immunoisolatory vehicle. In a first embodiment, the vehicle is formed by coextruding from a nested-bore extrusion nozzle materials which form the core and surrounding or peripheral regions, under conditions sufficient to gel, harden, or cast the matrix or membrane precursor(s) of the surrounding or peripheral region (and of the core region). A particular advantage of this coextrusion embodiment is that the cells in the core are isolated from the moment of formation of the vehicle, ensuring that the core materials do not become contaminated or adulterated during handling of the vehicle prior to implantation. A further advantage of the coextrusion process is that it ensures that the surrounding or peripheral region is free of cells and other core materials. The permeability and biocompatibility characteristics of the surrounding or peripheral region are determined by both the matrix or membrane precursor materials used, and the conditions under which the matrix or membrane is formed.

In another embodiment of the present method, the immunoisolatory vehicle is formed stepwise. For example, if the immunoisolatory vehicle being made includes a hydrogel core containing the isolated cells, the core can be formed initially, and the surrounding or peripheral matrix or membrane can be assembled or applied subsequently. Conversely, the surrounding or peripheral matrix or membrane can be preformed, and then filled with the preformed isolated-cell containing core material or with materials which will form the core (i.e., core precursor materials). The vehicle is sealed in such a manner that the core materials are completely enclosed. If a core precursor material is used, the vehicle is then exposed to conditions which result in formation of the core.

BRIEF DESCRIPTION OF THE FIGURES

FIG. 1 is a graphic representation of the differences in the permeability of alginate matrices formed under different conditions to test solutes of various molecular sizes.

FIG. 2 is a graphic representation of the results of a perfusion test of the functionality of immunoisolated versus unprotected islets maintained in vitro for four weeks. FIG. 2A depicts the results obtained with an immunoisolatory vehicle having a hydrogel core matrix and a peripheral jacket made of a permselective thermoplastic membrane. FIG. 2B depicts the results obtained with an immunoisolatory vehicle having a hydrogel core matrix and a peripheral hydrogel jacket.

FIG. 3 is a graphic representation showing the total amount of insulin released, and the amounts released during the first and second phase responses in the perfusion test also shown in FIG. 2. FIG. 3A depicts the results obtained with the dual-matrix immunoisolatory vehicle and FIG. 3B depicts the results obtained with the core matrix-permselective membrane immunoisolatory vehicle.

FIG. 4 is a graphic representation of the decrease in plasma glucose levels observed when immunoisolated xenogeneic islets are implanted into streptozotocin-induced diabetic mice for a period of 60 days. The immunoisolatory vehicle used was of the configuration described in Example 5.

FIG. 5 is a graphic representation of insulin release in a perfusion experiment using an immunoisolatory vehicle containing rat islets, of the configuration described in Example 5, recovered after a period of residence in vivo and challenged with glucose, with and without theophylline stimulation.

FIG. 6 is a graphic representation of the decrease in plasma glucose levels observed when immunoisolated xenogeneic islets are implanted into streptozotocin-induced diabetic mice for a period of 100 days. The immunoisolatory vehicle used was of the configuration described in Example 4.

FIG. 7 is a graphic representation of the permeability of an alginate matrix to various test solutes. Permeabilities were tested after storage in Hank's solution after 16 hours and 160 hours. The change in permeability is due to leaching of $Ca^{++}$ from the matrix.

FIG. 8 is a graphic comparison of the response to glucose challenge of rat islets isolated within dual matrix immunoisolatory vehicles with either thermoplastic or alginate jackets, following a period of residence in vivo in discordant xenogeneic recipients (guinea pigs).

FIG. 9 is a graphic representation of the partial restoration of normal motor behavior to rodents with experimentally induced Parkinson-like behavior, following implantation of an immunoisolatory vehicle containing adrenal chromaffin cells in a core matrix, with a surrounding jacket of permselective thermoplastic membrane.

FIG. 10 is a graphic representation of the mean body weight changes seen in quinolinic acid lesioned rats. Rats receiving immunoisolatory capsules containing bovine adrenal chromaffin cells maintained body weight significantly better than the other lesioned rats.

FIG. 11 is a graphic representation of the nonfasting plasma glucose concentrations of diabetic mice after implantation of type 2 acrylic copolymer hollow fibers containing either 1000 rat islets (A) or 500 rat islets (B) implanted either intraperitoneally (circles) or subcutaneously (squares).

FIG. 12 is a graphic representation of the effects on blood glucose in diabetic rats implanted with rat islets encapsulated in flat sheet devices.

DETAILED DESCRIPTION OF THE INVENTION

This invention relates to a biocompatible immunoisolatory vehicle suitable for long-term implantation into individuals. More particularly, the biocompatible immunoisolatory vehicle of the instant invention comprises (a) a core which contains a biologically active moiety, either suspended in a liquid medium or immobilized within a hydrogel or extracellular matrix, and (b) a surrounding or peripheral region of permselective matrix or membrane (jacket) which does not contain isolated cells, which is biocompatible, and which is sufficient to protect isolated cells if present in the core from immunological attack.

The term "individual" refers to a human or an animal subject.

A "biologically active moiety" is a tissue, cell, or other substance, which is capable of exerting a biologically useful effect upon the body of an individual in whom a vehicle of the present invention containing a biologically active moiety is implanted. Thus, the term "biologically active moiety" encompasses cells or tissues which secrete or release a biologically active molecule, product or solute; cells or tissues which provide a metabolic capability or function, such as the removal of specific solutes from the bloodstream; or a biologically active molecule or substance such as an enzyme, trophic factor, hormone, or biological response modifier.

When the biologically active moiety within the core of the biocompatible immunoisolatory vehicle comprises cells, the core is constructed to provide a suitable local environment for the continued viability and function of the cells isolated therein. The instant vehicle can be used to immunoisolate a wide variety of cells or tissues, spanning the range from fully-differentiated, anchorage-dependent cells or primary tissues, through incompletely-differentiated fetal or neonatal tissues, to anchorage-independent transformed cells or cell lines.

Many transformed cells or cell lines are most advantageously isolated within a vehicle having a liquid core. For example, PC12 cells (which secrete dopamine and are herein shown to be useful for the treatment of Parkinsonism) can be isolated within a vehicle whose core comprises a nutrient medium, optionally containing a liquid source of additional factors to sustain cell viability and function, such as fetal bovine or equine serum.

Unless otherwise specified, the term "cells" means cells in any form, including but not limited to cells retained in tissue, cell clusters, and individually isolated cells.

Implants of the vehicle and contents thereof retain functionality for greater than three months in vivo and in many cases for longer than a year. In addition, the vehicle of the current invention may be prepared of sufficient size to deliver an entire therapeutic dose of a substance from a single or just a few (less than 10) implanted and easily retrievable vehicles.

The core of the immunoisolatory vehicle is constructed to provide a suitable local environment for the particular cells isolated therein. In some embodiments, the core comprises a liquid medium sufficient to maintain the cells. Liquid cores are particularly suitable for maintaining transformed cells, such as PC12 cells. In other embodiments, the core comprises a gel matrix which immobilizes and distributes the cells, thereby reducing the formation of dense cellular agglomerations. The gel matrix may be composed of hydrogel or extracellular matrix components.

Suitably, the core may be composed of a matrix formed by a hydrogel which stabilizes the position of the cells in cell clumps. The term "hydrogel" herein refers to a three dimensional network of cross-linked hydrophilic polymers. The network is in the form of a gel substantially composed of water, preferably but not limited to gels being greater than 90% water. Cross-linked hydrogels can also be considered solids because they do not flow or deform without appreciable applied shear stress.

Compositions which form hydrogels fall into three classes for the purposes of this application. The first class carries a net negative charge and is typified by alginate. The second class carries a net positive charge and is typified by extracellular matrix components such as collagen and laminin. Examples of commercially available extracellular matrix components include Matrigel™ and Vitrogen™. The third class is net neutral in charge. An example of a net neutral hydrogel is highly crosslinked polyethylene oxide, or polyvinylalcohol.

Cores made of a hydrogel matrix are particularly suitable for maintaining cells or tissues which tend to form agglomerates or aggregates, such as the cells in islets of Langerhans, or adrenal chromaffin cells. The matrix should be of sufficient viscosity to maintain cell dispersion within the matrix. Optionally, the core of the instant vehicle can contain substances which support or promote the function of the isolated cells. These substances include natural or synthetic nutrient sources, extracellular matrix (ECM) components, growth factors or growth regulatory substances, or a population of feeder or accessory cells or $O_2$ carriers such as hemoglobins and fluorocarbons.

Herein, the term "aggregating" refers to a process of promoting cell clustering. The cells which form clusters may be obtained from naturally occurring agglomerates, such as pancreatic islets which are dispersed into single or small-clump suspension and subsequently reaggregated according to the methods described. Alternatively, the cells may be obtained originally as single cells or small cell clumps, and then aggregated to form the desired cluster size. Such cell clusters will generally contain about 3–400 cells, depending upon cell size and aggregation characteristics. Typically, the cluster contains about 10 to about 50 cells. The use of reaggregated pancreatic islet cells is advantageous for insuring proper diffusion characteristics within the core and maintaining islet viability.

Reaggregated islets also allow the use of smaller capsules. For instance, 500 non-reaggregated islets would generally require a capsule of approximately 14 cm in length (2% density). In contrast, capsules containing islets reaggregated to a size smaller than an intact islet may be as small as 1 to 2 cm in length because of more efficient packing. More efficient packing allows a lower pO2 outside the fiber to be tolerated without resultant necrotic cores. Built in tolerance for lower outside $pO_2$ has at least two advantages. Firstly, a smaller capsule size may be used to contain the same number of cells, i.e. increased tissue density within the implant is better tolerated. Secondly, implantation sites with known reduced $pO_2$., such as subcutaneous locations, may be used successfully. The presence of the alginate matrix further insures that the aggregates will not reassociate to large cell masses where internal cells would be deprived of nutrients and/or oxygen.

In one advantageous application of the invention, the cells are formed by reaggregating natural cell clusters into a form adapted for increased packing per unit volume as described supra.

Such reaggregated clusters are preferably characterized by improved diffusion of critical solutes to and from the cells within the cluster in comparison to natural cell clusters.

Cells which do not require an anchorage substrate are those which are able to form clumps or agglomerates and thus provide anchorage for each other. Exemplary clumping cell types are pancreatic islets, pancreatic beta-cell lines, Chinese hamster ovary (CHO) cells, and adrenal chromaffin cells. These cells are suitably enclosed in a negatively charged matrix such as alginate.

Fibroblasts generally survive well in a positively charged matrix and are thus suitably enclosed in extracellular-matrix type hydrogels. Certain cell types tend to multiply rapidly and could overgrow the space available within the core if they do not exhibit growth arrest. If the isolated cells do not exhibit growth arrest upon confluence, substances which induce quiescence can be included in the interior of the vehicle. In some instances, a hydrogel core may suffice to limit continued proliferation. For example, a hydrogel matrix precursor solution can be included but not exposed to polymerizing conditions. In the case of sodium alginate, a hydrogel will form slowly after implantation as calcium ions are scavenged from the surrounding tissues. Alternatively, growth inhibitory factors, or stimulators of differentiation can be incorporated into microbeads of a slowly degraded polymer such as polycarbonate, and cosuspended with the product-secreting cells. For instance, NGF or FGF can be used to stimulate PC-12 cell differentiation and terminate cell division.

Other cells, particularly primary cells or tissues, tend to adhere to each other and form dense agglomerations which develop central necrotic regions due to the relative inaccessibility of nutrients and oxygen to cells embedded within the agglomerated masses. These dense cellular masses can form slowly, as a result of cell growth into dense colonies, or rapidly, upon the reassociation of freshly-dispersed cells or tissue mediated by cell-surface adhesion proteins. Cells or tissues which are highly metabolically active are particularly susceptible to the effects of oxygen or nutrient deprivation, and die shortly after becoming embedded in the center of an agglomerate. Many endocrine tissues, which normally are sustained by dense capillary beds, exhibit this behavior; islets of Langerhans and adrenal chromaffin cells are particularly sensitive. Cells or tissues which exhibit this behavior perform most satisfactorily in vehicles comprising a hydrogel matrix core, sufficient to immobilize the cells or tissue, thereby preserving the access of nutrients and oxygen to the majority of them.

In other circumstances, the immobilizing hydrogel matrix further performs the additional function of producing or preserving functional units of a size and/or shape appropriate for maintaining desirable characteristics of the isolated cells. Moreover, the presence of the core matrix allows maintenance of a uniform distribution of cells or clusters of cells within the vehicle (i.e., the core matrix prevents settling and decreases mobility of the included cells).

One particularly advantageous use of hydrogel cores pertains to the encapsulation of actively dividing cells. Alginate or other hydrogels may be included in suspensions of actively dividing cells to be encapsulated. Following encapsulation and generation of the gel, the encapsulated cells are somewhat immobilized within the gel and new cells produced during cell division stay localized near the parent cell. In this manner clusters of cells are produced within the core. Such a growth method is advantageous in the case of cells such as the beta cell derived NIT cell line. In the absence of a core matrix these cells tend to grow attached along the inner walls of the encapsulation device, with very few cells growing freely within the cavity of the device. Growth only on the walls of the capsule leads to a cell population size that is restricted by the surface area of the inner capsule wall as opposed to a population that grows to fill the vehicle cavity. When alginate is included in the core, cell growth is no longer limited to the inner capsule surface. Rather, discrete spheres of NIT cells are produced throughout the core, resulting in a significantly larger total cell population than that which occurs in the absence of alginate.

Even in the presence of a core matrix, the size of tissue fragments which can be loaded into a given vehicle volume is limited by the appearance of central necrosis within the individual fragments. In one aspect of the instant invention, the useful amount of tissue fragments or cell clusters that can be placed within the immunoisolatory vehicle is increased by preparing the cells in a form with improved diffusional characteristics. Generally this means preparation of the tissue fragments to a size less than 75 $\mu$m diameter and most optimally to about 35 μm diameter or less for vehicles to be implanted peritoneally. Aggregates or clusters of cells in improved diffusional form are prepared for spontaneously reaggregating cells (e.g. pancreatic islets or adrenal chromaffin cells) by enzymatically dispersing the tissue, to single cell and small cell aggregate suspensions, followed by controlled reaggregation to the improved diffusional form.

Pancreatic islet cells still retain functionality and secrete insulin in response to glucose in near normal fashion following enzymatic dispersion and reaggregation. Cells from dispersed islets are reaggregated to the desired cluster size prior to loading into the vehicle. Reaggregation can be accomplished by the methods described by Britt, Diabetes, 34, pp. 898–903, or by similar methods. The optimal aggregate size for islets is the smallest size cluster which still maintains the desired physiological characteristics. The matrix or matrix forming materials may then be added to the cells, and the combination may be coextruded into or loaded into biocompatible immunoisolatory vehicles. If necessary, matrix formation may then be induced. In preferred embodiments, cells are reaggregated overnight at 37° C., without agitation. The development of aggregates is monitored by light microscopy until aggregates achieve a size of 25 to 75 μm preferably 35 μm diameter. Liquid uncrosslinked alginate is then added to the cells to a concentration of from 0.5 to 2%, the cells are incorporated into vehicles, the vehicles are sealed if necessary, and polymerization is induced by immersion of the vehicle in an aqueous solution containing $CaCl_2$.

Primary cells or tissues may be useful with the vehicle of the instant invention for various medical applications. For regulatory reasons and reasons of patient safety, it may sometimes be useful to employ as sources for primary cultures, animals of carefully controlled hereditary and developmental background. The presence of unwanted virus, bacteria and other pathogens may be limited through the use of specific pathogen free or gnotobiotic source animals. References and methods for the establishment, care and use of specific pathogen free and gnotobiotic herds are provided by Maniatis, O. P., et al. Can. J. Med., 42, p. 428 (1978); Matthews P. J., et al., Recent Advances in Germ Free Research, pp. 61–64, Tokai Univ. Press (1981), and in the National Accreditation Standards publication of the National SPF Swine Accrediting Agency, Inc., Conrad, Iowa.

Optionally, a matrix core can also contain materials which support or promote the function of the isolated cells. For example, extracellular matrix (ECM) components can be included to promote specific attachment or adhesion of the isolated cells. A combination of ECM components which is particularly suitable for fostering the growth of certain types of cells is taught in Kleinman et al., U.S. Pat. No. 4,829,000. The core matrix can provide a reservoir for soluble or releasable substances, such as growth factors or growth regulatory substances, or for natural or synthetic substances which enhance or improve the supply of nutrients or oxygen to the isolated cells. Thus, it can function in a manner similar to the bone marrow ECM, which has been reported to behave as a slow-release reservoir for myeloid lineage-specific growth factors such as granulocyte-macrophage colony stimulating factor (gmcsf). Gordon, M. Y., et al., Nature, 326, pp. 403–405 (1987). Thus, the core matrix can function as a reservoir for growth factors (e.g., prolactin, or insulin-like growth factor 2), growth regulatory substances such as transforming growth factor β (TGFB) or the retinoblastoma gene protein or nutrient-transport enhancers (e.g., perfluorocarbons, which can enhance the concentration of dissolved oxygen in the core). Certain of these substances are also appropriate for inclusion in liquid media.

Additionally, a population of feeder or accessory cells can be coisolated within the vehicle.

For example, hepatocytes can be coisolated with endothelial accessory cells, Cai, Z., et al., Artificial Organs, 12, pp. 388–393 (1988), or mixed with islet cells, Ricordi C., et al., Transplantation 45, pp. 1148–1151 (1987), or adrenal chromaffin cells can be coisolated with accessory cells which provide nerve growth factor (NGF), a substance needed by the chromaffin cells. In the latter case, fibroblasts which have been transfected with an expression vector for NGF can be used as accessory cells.

The instant vehicle can also be used as a reservoir for the controlled delivery of needed drugs or biotherapeutics. In such cases, the core, rather than containing cells or tissues, contains a high concentration of the selected drug or biotherapeutic. In addition, satellite vehicles containing substances which prepare or create a hospitable environment in the area of the body in which a biocompatible immunoisolatory vehicle containing isolated cells is implanted can also be implanted into a recipient. In such instances, the vehicle containing immunoisolated cells is implanted in the region along with satellite vehicles releasing controlled amounts of, for example, a substance which down-modulates or inhibits an inflammatory response from the recipient (e.g., anti-inflammatory steroids), or a substance which stimulates the ingrowth of capillary beds (i.e., an angiogenic factor).

The surrounding or peripheral region (jacket) of the instant vehicle is permselective, biocompatible, and immunoisolatory. It is produced in such a manner that it is free of isolated cells, and completely surrounds (i.e., isolates) the core, thereby preventing contact between any cells in the core and the recipient's body.

To be permselective, the jacket is formed in such a manner that it has a MWCO range appropriate both to the type and extent of immunological reaction it is anticipated will be encountered after the vehicle is implanted and to the molecular size of the largest substance whose passage into and out of the vehicle is desirable. The type and extent of immunological attacks which may be mounted by the recipient following implantation of the vehicle depend in part upon the type(s) of moiety isolated within it and in part upon the identity of the recipient (i.e., how closely the recipient is genetically related to the source of the biologically active moiety). When the implanted tissue is allogeneic to the recipient, immunological rejection may proceed largely through cell-mediated attack by the recipient's immune cells against the implanted cells. When the tissue is xenogeneic to the recipient, molecular attack through assembly of the recipient's cytolytic complement attack complex may predominate, as well as the antibody interaction with complement.

In reference to the permselectivity of the membranes and gels of the instant invention, the phrase "molecular weight cutoff" (MWCO) is used. It is recognized that there are many methods available for the determination of the molecular weight cutoff for a permselective membrane. Depending upon the method used, somewhat different MWCO estimates may be achieved for the same membrane. In the context of the current invention, MWCO refers to the results of the empirical determinations described herein, using the specific markers described under the specific conditions of the determination. Other methods of MWCO determination, to apply to the current invention, will need to be calibrated against the protocol of the instant invention according to methods known to practitioners in the art.

The jacket allows passage of substances up to a predetermined size, but prevents the passage of larger substances.

More specifically, the surrounding or peripheral region is produced in such a manner that it has pores or voids of a predetermined range of sizes; as a result, the vehicle is permselective. The molecular weight cutoff (MWCO) selected for a particular vehicle will be determined in part by the type and extent of immunological rejection it is anticipated will be encountered after the vehicle is implanted and in part by the molecular size of the largest substance to be allowed to pass into and/or out of the vehicle. For example, materials can be used to form permselective membranes or hydrogel matrices which allow passage of molecules up to about the size of C1q, a component of complement (about 400 kD), a protein required for the assembly of the cytolytic complement attack complex. In this instance, substances smaller than C1q can pass freely. It is also possible to form permselective matrices or membranes which allow passage of molecules up to about the size of immunoglobulin G (about 150 kD) and exclude larger molecules. Further, membranes or hydrogels which allow passage of molecules up to about the size of immunoglobulin M (about 1,000 kD) can be used; only very large substances, such as cells, will be excluded in this embodiment.

The MWCO of the surrounding or peripheral region must therefore be sufficiently low to prevent access of the substances required to carry out these attacks to the core, yet sufficiently high to allow delivery of the needed product to the recipient's body. It will therefore be apparent that the MWCO need not be strictly restricted to a range which excludes immunoglobulin G from the core. In fact, there are many cases in which higher MWCOs are not only permissible, but also advantageous. Indeed, higher MWCOs allow the delivery of a wide variety of useful products from immunoisolated cells, as well as the use of such cells to provide metabolic control of high molecular weight substances.

Thus, in appropriate cases, the peripheral or surrounding region can be made of materials which form permselective membranes or hydrogel matrices allowing the passage of molecules up to about the size of C1q (about 400 kD), the largest protein required for the assembly of the complement attack complex. Therefore, any cellular product or metabolite below about the size of C1q can pass freely through the vehicle. In other cases, it may still be desirable to exclude immuno-globulins. In such cases, materials which form matrices or membranes through which molecules which are equivalent to or larger than the size of immunoglobulin G (about 150 kD) cannot pass can be used. Cellular products or metabolites which are smaller than about 150 kD will still pass through the vehicle. In still other cases, where the patient is immunosuppressed or where the implanted tissue is syngeneic to the patient, a vigorous immunological attack is not likely to be encountered, and passage of a high molecular weight molecule may be desired. In these latter cases, materials which allow passage of all molecules up to about the size of immunoglobulin M (about 1,000 kD) can be used. These materials will impede the passage of only very large substances, such as cells.

In another aspect of the invention, it has been found that a molecular weight cutoff for the jacket considerably higher than that previously contemplated may be employed while maintaining the viability and function of the encapsulated cells. This permits the macrocapsules to be used in applications where the cells secrete a substance of high molecular weight. For this purpose, a macrocapsule with molecular cutoffs in excess of say 80 to 100 kD to as high as 200 to 1000 or 2000 kD or more may be employed in accordance with the present invention.

As used herein, the term "biocompatible" refers collectively to both the intact vehicle and its contents. Specifically, it refers to the capability of the implanted intact vehicle and its contents to avoid detrimental effects of the body's various protective systems and remain functional for a significant period of time. In addition to the avoidance of protective responses from the immune system, or foreign body fibrotic response, "biocompatible" also implies that no specific undesirable cytotoxic or systemic effects are caused by the vehicle and its contents such as would interfere with the desired functioning of the vehicle or its contents.

The jacket is biocompatible. That is, it does not elicit a detrimental host response sufficient to result in rejection of the implanted vehicle or to render it inoperable. Neither does the jacket elicit unfavorable tissue responses such as fibrosis. In addition, the external surface can be selected or designed in such a manner that it is particularly suitable for implantation at the selected site. For example, the external surface can be smooth, stippled or rough, depending on whether attachment by cells of the surrounding tissue is desirable. The shape or configuration can also be selected or designed to be particularly appropriate for the implantation site chosen.

The biocompatibility of the surrounding or peripheral region (jacket) is produced by a combination of factors.

Important for biocompatibility and continued functionality are vehicle morphology, hydrophobicity and the absence of undesirable substances either on the surface of, or leachable from, the vehicle itself. Thus, brush surfaces, folds, interlayers or other shapes or structures eliciting a foreign body response are avoided. The vehicle-forming materials are sufficiently pure that unwanted substances do not leach out from the vehicle materials themselves. Additionally, following vehicle preparation, the treatment of the external surface of the vehicle with fluids or materials (e.g. serum) which may adhere to or be absorbed by the vehicle and subsequently impair vehicle biocompatibility are avoided.

First, the materials used to form the vehicle are substances selected based upon their ability to be compatible with, and accepted by, the tissues of the recipient of the implanted vehicle. Substances are used which are not harmful to the recipient or to the isolated biologically active moiety. Preferred substances include reversibly and irreversibly gellable substances (e.g., those which form hydrogels), and water-insoluble thermoplastic polymers. Particularly preferred thermoplastic polymer substances are those which are modestly hydrophobic ,i.e. those having a solubility parameter as defined in Brandrup J., et al. *Polymer Handbook* 3rd Ed., John Wiley & Sons, NY (1989), between 8 and 15, or more preferably, between 9 and 14 (Joules/m$^3$)$^{1/2}$. The polymer substances are chosen to have a solubility parameter low enough so that they are soluble in organic solvents and still high enough so that they will partition to form a proper membrane. Such polymer substances should be substantially free of labile nucleophilic moieties and be highly resistant to oxidants and enzymes even in the absence of stabilizing agents. The period of residence in vivo which is contemplated for the particular immunoisolatory vehicle must also be considered: substances must be chosen which are adequately stable when exposed to physiological conditions and stresses. There are many hydrogels and thermoplastics which are sufficiently stable, even for extended periods of residence in vivo, such as periods in excess of one or two years. Examples of stable materials include alginate (hydrogel) and polyacrilonitrile/polyvinylchloride ("PAN/PVC" or "thermoplastic").

Second, substances used in preparing the biocompatible immunoisolatory vehicle are either free of leachable pyrogenic or otherwise harmful, irritating, or immunogenic substances or are exhaustively purified to remove such harmful substances. Thereafter, and throughout the manufacture and maintenance of the vehicle prior to implantation, great care is taken to prevent the adulteration or contamination of the vehicle with substances which would adversely affect its biocompatibility.

Third, the exterior configuration of the vehicle, including its texture, is formed in such a manner that it provides an optimal interface with the tissues of the recipient after implantation. This parameter will be defined in part by the site of implantation. For example, if the vehicle will reside in the peritoneal cavity of the recipient, its surface should be smooth. However, if it will be embedded in the soft tissues of the recipient, its surface can be moderately rough or stippled. A determining factor will be whether it is desirable to allow cells of the recipient to attach to the external surface of the vehicle or if such attachment must be avoided. An open-textured or sponge-like surface may promote the ingrowth of capillary beds, whereas a smooth surface may discourage excessive overgrowth by fibroblasts. Excessive overgrowth by fibroblasts is to be avoided, except where capillary undergrowth has occurred, as it may result in the deposition of a poorly-permeable basement membrane around the vehicle and walling off of the isolated cells from contact with the recipient's body.

Certain vehicle geometries have also been found to specifically elicit foreign body fibrotic responses and should be avoided. Thus vehicles should not contain structures having interlayers such as brush surfaces or folds. In general, opposing vehicle surfaces or edges either from the same or adjacent vehicles should be at least 1 mm apart, preferably greater than 2 mm and most preferably greater than 5 mm. Preferred embodiments include cylinders, "U"-shaped cylinders, and flat sheets or sandwiches.

The surrounding or peripheral region (jacket) of the biocompatible immunoisolatory vehicle can optionally include substances which decrease or deter local inflammatory response to the implanted vehicle, and/or generate or foster a suitable local environment for the implanted cells or tissues. For example antibodies to one or more mediators of the immune response could be included. Available potentially useful antibodies such as antibodies to the lymphokines tumor necrosis factor (TNF), and to interferons (IFN) can be included in the matrix precursor solution. Similarly, an anti-inflammatory steroid can be included. Christenson, L., et al., J. Biomed. Mat. Res., 23, pp. 705–718 (1989); Christenson, L., Ph.D. thesis, Brown University, 1989, incorporated by reference.

Alternatively, a substance which stimulates angiogenesis (ingrowth of capillary beds) can be included. This may be particularly desirable where the isolated cells or tissues require close contact with the recipient's bloodstream to function properly (e.g., insulin-producing islets of Langerhans). Cell which are genetically engineered to secrete antibodies may also be included in the matrix.

Because of its biocompatibility, the vehicle is suitable for long-term isolation of biologically useful cells and/or substances from the various protective systems of the body. As used herein, the term "protective systems" refers to the types of immunological attack which can be mounted by the immune system of an individual in whom the instant vehicle is implanted, and to other rejection mechanisms, such as the fibrotic response, foreign body response and other types of inflammatory response which can be induced by the presence of a foreign object in the individuals' body.

The jacket of the present vehicle is immunoisolatory. That is, it protects cells in the core of the vehicle from the immune system of the individual in whom the vehicle is implanted. It does so (1) by preventing harmful substances of the individual's body from entering the core of the vehicle, (2) by minimizing contact between the individual and inflammatory, antigenic, or otherwise harmful materials which may be present in the core and (3) by providing a spatial and physical barrier sufficient to prevent immunological contact between the isolated moiety and detrimental portions of the individual's immune system.

The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thickness of 20 to 50 microns are particularly preferred. Types of immunological attack which can be prevented or minimized by the use of the instant vehicle include attack by macrophages, neutrophils, cellular immune responses (e.g. natural killer cells and antibody-dependent T cell-mediated cytoloysis [ADCC]), and humoral response (e.g. antibody-dependent complement mediated cytolysis).

The type and extent of immunological response by the recipient to the implanted vehicle will be influenced by the relationship of the recipient to the isolated biologically active moiety. For example, if the isolated materials comprise syngeneic cells, these will not cause a vigorous immunological reaction, unless the recipient suffers from an autoimmunity with respect to the particular cell or tissue type within the vehicle. There are several disease or deficiency states which have recently been determined to have an autoimmune etiology, most notably Type I, insulin-dependent Diabetes mellitus, wherein the insulin secreting pancreatic islet $\beta$ cells are destroyed by the individual's immune system. Fan, M. -Y. et al., Diabetes, 39, pp. 519–522 (1990).

Syngeneic cells or tissue are rarely available. In many cases, allogeneic or xenogeneic cells or tissue (i.e., from donors of the same species as, or from a different species than, the prospective recipient) may be available. The immunoisolatory vehicle allows the implantation of such cells or tissue, without a concomitant need to immunosuppress the recipient. Therefore, the instant vehicle makes it possible to treat many more individuals than can be treated by conventional transplantation techniques. For example, far more patients suffer from Type 1 diabetes than can be transplanted with human donor islets (in 1990, fewer than about 4,000 suitable cadaver organ donors became available in the U.S. for all organ transplants). The supply of donor porcine or bovine islets is far greater; if these xenoislets are appropriately immunoisolated according to the instant invention, the diabetic condition of a far greater number of patients can be remedied.

The type and vigor of an immune response to xenografted tissue is expected to differ from the response encountered when syngeneic or allogeneic tissue is implanted into a recipient. This rejection may proceed primarily by cell-mediated, or by complement-mediated attack; the determining parameters in a particular case may be poorly understood. However, as noted previously, the exclusion of IgG from the core of the vehicle is not the touchstone of immunoprotection, because IgG alone is insufficient to produce cytolysis of the target cells or tissues.

Using the macrocapsules of the present invention, preferably with allogeneic tissue, but even with xenografts, it is possible to deliver needed high molecular weight products or to provide metabolic functions pertaining to high molecular weight substances, provided that critical substances necessary to the mediation of immunological attack are excluded from the immunoisolatory vehicle. These substances may comprise the complement attack complex component C1q, or they may comprise phagocytic or cytotoxic cells; the instant immunoisolatory vehicle provides a protective barrier between these harmful substances and the isolated cells. Thus, the present immunoisolatory vehicle can be used for the delivery even from allogeneic or xenogeneic cells or tissue, products having a wide range of molecular sizes, such as insulin, parathyroid hormone, interleukin 3, erythropoietin, albumin, transferrin, and Factor VIII.

The jacket of the instant vehicle is made of a material which may be the same as that of the core or may be different. In either case, the material used results in a surrounding or peripheral region which is permselective, biocompatible and immunoisolatory. The jacket may be formed freely around the core without chemical bonding or, alternatively, the jacket may be directly cross-linked to the core matrix. In either case, formation of the vehicle of the present invention does not require polymers of opposite charge to the core being present in an interfacial layer or in the jacket.

The surrounding or peripheral region (jacket) can be made of a hydrogel matrix or of a different material, such as a thermoplastic membrane. It can also be made of a matrix-membrane composite, such that a permselective thermoplastic membrane having matrix-filled pores, is formed.

Suitably, the external jacket may be formed of a thermoplastic material known to be biocompatible, such as the ones described herein. In addition, other jackets which have been used in the microcapsule field may also be used herein, such as alginate, suitably cross-linked with a multivalent ion such as calcium.

Preferably, the core and external jacket form an interface free of "ionic bonding" between oppositely charged polymers and free of an intermediate layer of the type used in prior art microcapsules. Ionic bonding refers to an ionic interaction of a core of one charge (positive or negative) and the jacket (or an intermediate layer) of opposite charge.

In previously existing devices, the core and jacket were linked via ionic bonds between oppositely charged polymers in one of two ways. (1) The devices of Rha (U.S. Pat. No; 4,744, 933) were constructed of a charged inner core material and an outer jacket material of the opposite charge. (2) The devices of Lim and Sun (U.S. Pat. Nos: 4,352,833 and 4,409,331) included an intermediate layer of poly-L-lysine (PLL), which is positively charged, to link the negatively charged core with the negatively charged jacket material. The elimination of a PLL layer is advantageous in that PLL is believed to be fibrogenic in the host. PLL may also have unwanted growth effects for some cells. Also, the jacket of the device of the invention can be controlled for permselectivity better than those made with PLL.

The vehicle of the present invention is distinguished from the microcapsules of Lim and Sun (Lim, F., Sun, A. M., *Science* 210, pp. 908–910 (1980); Sun, A. M., *Methods in Enzymology* 137, pp. 575–579 (1988) by its outer jacket which ensures that cells cannot project outside of the core. The capsules of Lim and Sun suffered from the disadvantage that portions of encapsulated cells could potentially project from the core through the poly-L-lysine layer and thereby be more likely to elicit inflammatory responses from the host's immune system. That microcapsule technology relies on the presence of potentially bioactive ionic bonds to form the microcapsule. By virtue of their ionic nature, those microcapsules are susceptible to deterioration following implantation due to competition for the ionic bonds that take place in the body of the host after capsule implantation. This problem is minimized by the relatively non-ionic macrocapsules of the present invention. A further advantage of the macrocapsules of the present invention lies in their capacity to contain more cells in a single device than is possible in microcapsule technology.

The term "dual matrix vehicles" refers to vehicles with a cell-containing core and an external jacket free of cells. In one embodiment, the matrix core is formed of a hydrogel which is cross-linked to a hydrogel jacket, suitably in the form of a rod or other shape. The hydrogel jacket may be formed independently as a sheath around the matrix without cross-linking. The hydrogel care is not necessarily linked to the outer jacket by means of opposite ionic charges. In another embodiment, the external jacket is formed of a thermoplastic material which is not linked to the core matrix by chemical bonding.

If a dual matrix immunoisolatory vehicle is to be formed, the surrounding or peripheral region can be made of a hydrogel selected from the above-listed matrix precursors. If the surrounding or peripheral region of the vehicle is to comprise a permselective membrane, other precursor materials can be used. For example, the surrounding or peripheral region can be made from water-insoluble, biocompatible thermoplastic polymers or copolymers. Several of the polymers or copolymers taught by Michaels, U.S. Pat. No. 3,615,024, which is hereby incorporated by reference, fulfill these criteria.

A preferred membrane casting solution comprises a polyacrylonitrile-polyvinylchloride (PAN/PVC) copolymer dissolved in the water-miscible solvent dimethylsulfoxide (DMSO). This casting solution can optionally comprise hydrophilic or hydrophobic additives which affect the permeability characteristics of the finished membrane. A preferred hydrophilic additive for the PAN/PVC copolymer is polyvinylpyrrolidone (PVP). Other suitable polymers comprise polyacrylonitrile (PAN), polymethylmethacrylate (PMMA), polyvinyldifluoride (PVDF), polyethylene oxide, polyolefins (e.g., polyisobutylene or polypropylene), polysulfones, and cellulose derivatives (e.g., cellulose acetate or cellulose butyrate). Compatible water-miscible solvents for these and other suitable polymers and copolymers are found in the teachings of U.S. Pat. No. 3,615,024.

In a preferred embodiment, the core is surrounded by a biocompatible hydrogel matrix free of cells projecting externally from the outer layer. The macrocapsules of the present invention are distinguished from the microcapsules of Rha, Lim, and Sun (Rha, C. K. et al., U.S. Pat. No. 4,744,933; Sun, A. W., supra) by (1) the complete exclusion of cells from the outer layer of the macrocapsule, and (2) the thickness of the outer layer of the macrocapsule. Both qualities contribute to the immunoisolation of encapsulated cells in the present invention. The microcapsules of Rha were formed by ionic interaction of an ionic core solution with an ionic polymer of opposite charge. The microcapsules of Lim and Sun were formed by linking an external hydrogel jacket to the core through an intermediate layer of poly-L-lysine (PLL).

In the microcapsules of Lim and Sun, the intermediate PLL layer was not sufficiently thick to guarantee that portions of the encapsulated cells would not penetrate through and beyond the layer. Cells penetrating the PLL layer are potential targets for an immune response. All these capsules, including those disclosed by Rha, also suffer the following additional limitations: (a) they are round, and (b) the formation of the outer layer is dependent upon direct ionic bonding or polyamide linkage with an inner layer or core substance. The disadvantages of round shape and direct ionic bonding between polymers are described supra.

In the capsules of Rha, Lim, and Sun, since the chemical identity of the inner substance is either dictated by choice of outer layer, or PLL, the ability to vary growth conditions on the inside of these capsules is greatly limited. Since there are often specific growth conditions which need to be met in order to successfully encapsulate specific cell types, these capsules generally have a limited utility or require considerable experimentation to establish appropriate outer layers for a given internal substance. In contrast, in the instant invention, the identity of the core material does not place strict limitations on the identity of the outer jacket material or vice versa. This allows the material of the inner hydrogel to be selected according to criteria important for cell viability and growth, and the outer jacket material to be selected on the basis of immunoisolatory properties, biocompatibility, and/or manufacturing considerations.

The microcapsules of Rha, Lim, and Sun have a greater potential for bioincompatibility, fibrogenesis, and vehicle deterioration than do the macrocapsules of the present invention. A variety of biological systems are known to interact with and break down the ionic bonds required for the integrity of microcapsules. PLL evokes unfavorable tissue reactions to the capsule. Most notably, this is a fibrotic response. Thus, if there is any break in the external layer, if it is not of sufficient thickness, if the PLL layer begins to degrade, or if encapsulated cells are entrapped within the external layer sufficiently close to its outer surface, the microcapsule can trigger a fibrotic response. The term "fibrogenic" is used herein in reference to capsules or materials which elicit a fibrotic response in the implantation site. As set forth herein, the external jacket of the immunoisolatory, non-fibrogenic macrocapsule of the present invention may be formed in a number of ways.

In one embodiment, the core is preformed by cross-linking a hydrogel matrix with a cross-linking agent, preferably a multivalent cation such as calcium. However, other known hydrogel cross-linking agents may also be employed. After cross-linking, the core is dipped into a solution of hydrogel to form a second layer free of cells in the core which, simultaneously or thereafter, is cross-linked suitably in the same manner. In the instant embodiment, cross-linking of the core material with the jacket material is accomplished via the cross-linking agent. For instance, when the core and jacket materials are both negatively charged hydrogels, the core and the jacket are cross-linked with each other via their mutual attraction to the positive charges on the cross-linking agent, preferably calcium. The core and jacket may be formed of the same or different type of hydrogel, provided that both have the same charge. Notably, the instant vehicle is not formed through direct ionic bonding between anionic and cationic polymers as described in Rha, C. K., U.S. Pat. No. 4,744,933.

Herein, the term "direct ionic bonding" refers to the type of chemical bonding in which two oppositely charged polymers are attracted to one another because of their oppositely charged moieties.

The instant embodiment is distinguished from that of Rha because, in the instant embodiment, both the core material and jacket material have the same charge, and their association is via an oppositely charged cross-linking agent. This embodiment may be in the form of a microcapsule or a macrocapsule but, for reasons set forth herein, the macrocapsule form is preferred.

The present immunoisolatory vehicle can be formed in a wide variety of shapes and combinations of suitable materials. A primary consideration in selecting a particular configuration for the vehicle when cells are present is the access of oxygen and nutrients to the isolated cells or tissues, and passage of waste metabolites, toxins and the secreted product from the vehicle. The immunoisolatory vehicle can be any configuration appropriate for maintaining biological activity and providing access for delivery of the product or function, including for example, cylindrical, rectangular, disk-shaped, patch-shaped, ovoid, stellate, or spherical. Moreover, the vehicle can be coiled or wrapped into a mesh-like or nested structure. If the vehicle is to be retrieved after it is implanted, configurations which tend to lead to migration of the vehicle(s) from the site of implantation, such as spherical vehicles small enough to travel in the recipient's blood vessels, are not preferred. Certain shapes, such as rectangles, patches, disks, cylinders, and flat sheets offer greater structural integrity and are preferable where retrieval is desired.

The instant vehicle must provide, in at least one dimension, sufficiently close proximity of any isolated cells in the core to the surrounding tissues of the recipient, including the recipient's bloodstream, in order to maintain the viability and function of the isolated cells. However, the diffusional limitations of the materials used to form the vehicle do not in all cases solely prescribe its configurational limits. Certain additives can be used which alter or enhance the diffusional properties, or nutrient or oxygen transport properties, of the basic vehicle. For example, the internal medium can be supplemented with oxygen-saturated perfluorocarbons, thus reducing the needs for immediate contact with blood-borne oxygen. This will allow isolated cells or tissues to remain viable while, for instance, a gradient of angiotensin is released from the vehicle into the surrounding tissues, stimulating ingrowth of capillaries. References and methods for use of perfluorocarbons are given by Faithful, N. S. *Anaesthesia,* 42, pp. 234–242 (1987) and NASA Tech Briefs MSC-21480, U.S. Govt. Printing Office, Washington, D.C. 20402, incorporated herein by reference. Alternatively for clonal cell lines such as PC12 cells, genetically engineered hemoglobin sequences may be introduced into the cell lines to produce superior oxygen storage. NPO-17517 NASA Tech Briefs, 15, p. 54.

In general, in the absence of oxygen carrier additives, when the cells are present the vehicle will have a maximum depth-to-surface distance of no more than 2 mm in at least one dimension, with a maximum depth of 800 microns being preferred. One or several vehicles may be required to produce the desired effect in the recipient.

The thickness of the immunoisolatory vehicle jacket should be sufficient to prevent an immunoresponse by the patient to the presence of the vehicles. For that purpose, the vehicles preferably have a minimum thickness of 1 $\mu$m or more free of the cells.

Additionally, reinforcing structural elements can be incorporated into the vehicle. These structural elements can be made in such a fashion that they are impermeable, and are appropriately configured to allow tethering or suturing of the vehicle to the tissues of the recipient. In certain circumstances, these elements can act to securely seal the surrounding or peripheral region (e.g., at the ends of a cylindrical vehicle, or at the edges of a disk-shaped vehicle), completing isolation of the core materials (e.g., a molded thermoplastic clip). For many configurations, it is desirable that these structural elements should not occlude a significant area of the permselective surrounding or peripheral region.

In one preferred embodiment, the implantable immunoisolatory vehicle of the present invention is of a sufficient size and durability for complete retrieval after implantation. To be contrasted with such microcapsules, which have a typical maximum practical volume on the order of 1 $\mu$l, the preferred immunoisolatory vehicle of the present invention is termed "macrocapsule". Such macrocapsules have a core of a preferable minimum volume of about 1 to 10 $\mu$l and depending upon use are easily fabricated to have a value in excess of 100 $\mu$l.

In terms of retrievability, microspheres are generally less practical than macro-capsules. In order for tissue encapsulated in microspheres to provide a therapeutic dose of insulin, for instance, the number of microspheres must be increased to such a large extent that significant retrievability becomes impossible. Additionally, an increase in the volume of tissue placed within a microsphere requires a corresponding increase in surface area. Within a sphere, because surface area scales with $r^2$ where as volume scales with $r^3$, as the volume of encapsulated tissue volume increases, the required capsule size to provide sufficient surface area for nutrient diffusion to the encapsulated tissue quickly becomes impractical.

Macrocapsules in the shapes of cylinders or flat sheets do not have these limitations because volume increases more proportionately to surface area such that the diffusional transport of nutrients and products for increased amounts of tissue can be accommodated by increasing the surface area without unwieldy increases in total vehicle size. If, for example, about 10,000 islets are required per kg body weight to restore normoglycemia to a diabetic patient, from 1,000 to 10,000 microcapsules must be transplanted per kg body weight (e.g. 1–10 islets per capsule). This number of microcapsules could not be easily retrieved, if retrieval were required. In contrast, the macrocapsules of the instant invention may easily hold greater than 1,000 islets to as high as 500,000 islets or more per vehicle. The preferred embodiment would require fewer than 5–10 vehicles per patient, making macrocapsules more easily retrieved than a large number of microcapsules.

The macrocapsules of the present invention are distinguished from microcapsules (Sun, A. M., supra; Rha, U.S. Pat. No. 4,744,933) by the capacity of macrocapsules to contain over $10^4$ cells and maintain them in viable condition. The droplet methods used in the making of microcapsules, in order to ensure cell viability, necessarily limit the number of cells per capsule to fewer than $10^4$.

The instant invention also relates to a method for making an immunoisolatory vehicle. The vehicles of this invention can be formed either by coextrusion or stepwise assembly. Techniques for coextrusion which can be used to form the instant vehicle are taught in copending U.S. patent application Ser. No. 07/461,999, filed Jan. 8, 1990, which is herein incorporated by reference. For example, a coextrusion device similar to that taught by U.S. Ser. No. 07/461,999 is used in making the subject vehicle. The device has a nested-bore extrusion nozzle, the lumen of each bore (inner and outer) being appropriately connected to sterile chambers for delivery of the core and surrounding region materials.

The nozzle can be of any configuration appropriate to produce an immunoisolatory vehicle whose shape is appropriate to the metabolic needs of the cells to be immobilized and the permeability and strength of the matrix which will surround them. For example, the nozzle can be circular, elliptical, stellate, or slot-shaped. Optionally, the nested bores can be coaxial. The widest aperture of the nozzle must be commensurate with the maximum diffusional depth appropriate to the vehicle being formed, including the metabolic needs of the isolated cells or tissues, and the materials of the core and peripheral regions.

Upon extrusion of the core and peripheral region materials from the inner and outer chambers through the corresponding bores of the nozzle under conditions sufficient to gel, harden, or cast the matrix or membrane precursor(s) of the surrounding or peripheral region (and of the core region), an elongated vehicle of the selected shape is continuously formed. The length of the vehicle, and therefore its volume or capacity, can be controlled to produce vehicles of sizes appropriate for the particular use contemplated.

An immunoisolatory vehicle formed by coextrusion in this manner is particularly preferred because use of this means ensures that the cells in the core are isolated from the moment of formation of the vehicle. Thus, it also ensures that the core materials do not become contaminated or adulterated during handling of the vehicle prior to implantation.

Furthermore, the nature of the coextrusion process is such that it ensures that the surrounding or peripheral region (jacket) is free of the materials in the core, including the cells, thus assuring that these cells will be immunoisolated when the vehicle is implanted into an individual. The permeability, molecular weight cutoff, and biocompatibility characteristics of the surrounding or peripheral region are determined by both the chosen matrix or membrane precursor materials used, and the conditions under which the matrix or membrane is formed.

The co-extruded vehicles may be formed with a hydrogel matrix core and a thermoplastic or hydrogel jacket. Such macrocapsules may be formed with a core and jacket of the same or different hydrogel which may be cross-linked to each other or not.

If a dual-matrix immunoisolatory vehicle (e.g., an alginate matrix) is formed, the permeability of the surrounding matrix can be determined by adjusting the concentration of matrix precursor used (e.g., sodium alginate), and/or the concentration of gelling agent (in the case of alginate, a divalent cation such as $Ca^{++}$) present in an immersion bath into which the materials are coextruded.

If an immunoisolatory vehicle with a surrounding or peripheral region of thermoplastic membrane is desired, the pore size range and distribution can be determined by varying the solids content of the solution of precursor material (the casting solution), the chemical composition of the water-miscible solvent, or optionally including a hydrophilic or hydrophobic additive to the casting solution, as taught by U.S. Pat. No. 3,615,024. The pore size may also be adjusted by varying the hydrophobicity of the coagulant and/or of the bath.

Typically, the casting solution will comprise a polar organic solvent containing a dissolved, water-insoluble polymer or copolymer. This polymer or copolymer precipitates upon contact with a solvent-miscible aqueous phase, forming a permselective membrane at the site of interface. The size of pores in the membrane depends upon the rate of diffusion of the aqueous phase into the solvent phase; the hydrophilic or hydrophobic additives affect pore size by altering this rate of diffusion. As the aqueous phase diffuses farther into the solvent, the remainder of the polymer or copolymer is precipitated to form a trabecular support which confers mechanical strength to the finished vehicle.

The external surface of the vehicle is similarly determined by the conditions under which the dissolved polymer or copolymer is precipitated (i.e., exposed to the air, which generates an open, trabecular or sponge-like outer skin, immersed in an aqueous precipitation bath, which results in a smooth permselective membrane bilayer, or exposed to air saturated with water vapor, which results in an intermediate structure). Again, it will be readily appreciated that this method of forming the immunoisolatory vehicle ensures that the peripheral or surrounding membrane is free of the cells in the core which are desired to be isolated from the immune system of the individual in whom the vehicle is to be implanted.

The surface texture of the vehicle is dependent in part on whether the extrusion nozzle is. positioned above, or immersed in, the bath: if the nozzle is placed above the surface of the bath a roughened outer skin of PAN/PVC will be formed, whereas if the nozzle is immersed in the bath a smooth external surface is formed.

The immunoisolatory vehicle can also be formed in a stepwise manner. For vehicles wherein the core comprises, in addition to the cells desired to be isolated, a hydrogel matrix, the core can be formed initially, and the surrounding or peripheral matrix or membrane can be assembled or applied subsequently. The matrix core can either be formed by extrusion or by molding. In a preferred embodiment, a patch- or sheet-shaped vehicle is formed by stepwise extrusion of calendared sheets. In this embodiment, a sheet of core material is layered onto a sheet of peripheral region material, then covered by a second sheet of peripheral region material. The edges of the vehicle are then sealed by crimping, compressing, heating, sealing with a biocompatible glue, or binding into a preformed biocompatible impermeable clip or combinations of the above.

Conversely, the surrounding or peripheral matrix or membrane can be preformed, filled with the materials which will form the core (for instance, using a syringe), and subsequently sealed in such a manner that the core materials are completely enclosed. The vehicle can then be exposed to conditions which bring about the formation of a core matrix if a matrix precursor material is present in the core. Alternatively, a patch- or sheet-shaped matrix core can be formed by molding, then sandwiched between sheets of permselective membrane and sealed or clipped in the manner described above to complete the isolation of the core materials.

It is also possible for a single, continuous hydrogel matrix to provide both immunoisolation and support or immobilization. For example, this can be accomplished by including the isolated cells within the vehicle distributed in a concentric gradient about the core, such that the peripheral region of the vehicle is free of the immobilized cells. Immunoisolatory vehicles of this nature can be made in at least two ways. First, a mixture of cells suspended in a solution of a hydrogel matrix precursor, which is denser than the isolated cells, can be extruded from the nozzle of a simple extrusion device. In this manner, the cells are forced into the core region of the forming vehicle. Alternatively, the cell-matrix precursor mixture can be extruded from the core lumen of a nested-bore nozzle, while simultaneously delivering a stream of a gelling agent (e.g., for alginate, a solution of calcium chloride) through the peripheral nozzle, whereby the surface and periphery of the vehicle polymerize first, thus forcing the suspended cells into the core.

As noted previously, the vehicle can provide for the implantation of diverse cell or tissue types, including fully-differentiated, anchorage-dependent, fetal or neonatal, or transformed, anchorage-independent cells or tissue. The cells to be immunoisolated are prepared either from a donor (i.e., primary cells or tissues, including adult, neonatal, and fetal cells or tissues) or from cells which replicate in vitro (i.e., immortalized cells or cell lines, including genetically modified cells). In all cases, a sufficient quantity of cells to produce effective levels of the needed product or to supply an effective level of the needed metabolic function is prepared, generally under sterile conditions, and maintained appropriately (e.g. in a balanced salt solution such as Hank's salts, or in a nutrient medium, such as Ham's F12) prior to isolation.

In another aspect of the invention, the macrocapsules are of a shape which tends to reduce the distance between the center of the macrocapsule and the nearest portion of the jacket for purposes of permitting easy access of nutrients from the patient into the cell or of entry of the patient's proteins into the cell to be acted upon by the cell to provide a metabolic function, such as interaction with cholesterol or the like. In that regard, a non-spherical shape is preferred, such as a long tube or flat plate, or the like. The optimum shape for this purpose may be calculated by known techniques as set forth herein.

Four important factors influencing the number of cells or amount of tissue to be placed within the core of the biocompatible immunoisolatory vehicle (i.e., loading density) of the instant invention are: (1) vehicle size and geometry; (2) mitotic activity within the vehicle; (3) viscosity requirements for core preparation and or loading; and (4) pre-implantation assay and qualification requirements.

With respect to the first of these factors, (capsule size and geometry), the diffusion of critical nutrients and metabolic requirements into the cells as well as diffusion of waste products away from the cell are critical to the continued viability of the cells. Since diffusional access to the contents of the vehicle is limited by vehicle surface area, surface to volume relationships of various shapes and size vehicles will be critical in determining how much viable tissue can be maintained within the vehicle.

Among the metabolic requirements met by diffusion of substances into the vehicle is the requirement for oxygen. The oxygen requirements of the specific cells must be determined for the cell of choice. Methods and references for determination of oxygen metabolism are given in Wilson D. F. et al., *J. Biol. Chem.*, 263, pp. 2712–2718, (1988). The oxygen requirement for islet cells has been applied to coupled diffusion reaction models accounting for diffusional transport from surrounding tissue through the vehicle wall and tissue compartment (core), and used to calculate the expected viability of islet cells in a number of vehicles of different sizes and configurations, after the method of Dionne, K. E., Ph.D. Thesis, Massachusetts Institute of Technology (1989). For intact pancreatic islets, these calculations agree well with experimental observations.

For a cylindrical vehicle of 900 microns outer diameter, implanted into the peritoneal cavity (pO2≈45–50 mmHg), the optimal total cell volume is in the range of up to 20%, preferably 1–15%, most preferably about 5% of the vehicle volume. If this capsule were 20 cm in length it would have a volume of 100 mm$^3$. To provide the same amount of surface area with a single sphere, e.g. to support comparable amounts of tissue, would require a volume of 1,047 mm$^3$.

For a cylindrical vehicle of 400 microns the optimal cell volume is between 35–65% total vehicle volume, and is preferably 35%. These calculations also take into account the partial oxygen pressure at the site of implantation. At implantation sites where the oxygen pressure is less than the peritoneum (e.g., subcutaneous pO2≈20 mmHg), lower loading densities will be required. Implantation into arteries (pO2>95 mmHg) and the brain (pO2>75 mmHg) will allow support of greater tissue volume per unit vehicle.

Other vehicle configurations, such as disk- shaped or spherical, are also possible and optimal cell volumes may be similarly calculated for these geometries. Actual loading densities will consider not only these diffusional considerations but also the other considerations given below.

With respect to the second factor (cell division), if the cells selected are expected to be actively dividing while in the vehicle, then they will continue to divide until they fill the available space, or until phenomena such as contact inhibition limit further division. For replicating cells, the geometry and size of the vehicle will be chosen so that complete filling of the vehicle core will not lead to deprivation of critical nutrients due to diffusional limitations. In general, vehicles that will be filled to confluency with cells or tissue will be no more than 250 microns in cross-section, such that cells in the interior will have less than 15 cells between them and an external diffusional surface, preferably less than 10 cells and more preferably less than 5 cells.

In general, for cells not expected to divide within the vehicle, such as chromaffin cells, pancreatic islet cells and the like, the appropriate cell densities will be calculated from the diffusional considerations listed above.

With respect to the third factor (viscosity of core materials) cells in densities occupying up to 70% of the vehicle volume can be viable, but cell solutions in this concentration range would have considerable viscosity. Introduction of cells in a very viscous solution into the vehicle could be prohibitively difficult. In general, for both two step and coextrusion strategies, discussed below, cell loading densities of higher than 30% will seldom be useful, and in general optimal loading densities will be 20% and below. For fragments of tissues, it is important, in order to preserve the viability of interior cells, to observe the same general guidelines as above and tissue fragments should not exceed 250 microns in diameter with the interior cells having less than 15, preferably less than 10 cells between them and the nearest diffusional surface.

Finally, with respect to the fourth factor (preimplantation and assay requirements), in many cases, a certain amount of time will be required between vehicle preparation and implantation. For instance, it may be important to qualify the vehicle in terms of its biological activity. Thus, in the case of mitotically active cells, preferred loading density will also consider the number of cells which must be present in order to perform the qualification assay.

In most cases, prior to implantation in vivo it will be important to use in vitro assays to establish the efficacy of the biologically active moiety within the vehicle. Vehicles containing the moiety of interest can be constructed and analyzed using model systems. In a preferred embodiment of the instant invention, the diffusion of glucose into the vehicle is used to stimulate insulin release from pancreatic islet cells. The appearance of insulin outside the vehicle is monitored through the use of an appropriately specific radioimmunoassay. Such procedures allow the determination of the efficacy of the vehicle on a per cell or unit volume basis.

Following the above guidelines for vehicle loading and for determination of vehicle efficacy, the actual vehicle size for implantation will then be determined by the amount of biological activity required for the particular application. In the case of secretory cells releasing therapeutic substances, standard dosage considerations and criteria known to the art will be used to determine the amount of secretory substance required. Factors to be considered include; the size and weight of the recipient; the productivity or functional level of the cells; and, where appropriate, the normal productivity or metabolic activity of the organ or tissue whose function is being replaced or augmented. It is also important to consider that a fraction of the cells may not survive the immunoisolation and implantation procedures, as well as whether the recipient has a preexisting condition which can interfere with the efficacy of the implant. Vehicles of the instant invention can easily be manufactured which contain many thousands of cells. In preferred embodiments, therapeutically useful immunoisolatory vehicles used to provide insulin to insulin deficient rats contained on the order of 1,000 islets. Larger vehicles can also be conveniently prepared by the method of the current invention.

Because of the potentially large capacity of the immunoisolatory vehicles, the treatment of many conditions will require only one or at most a few (less than 10) implanted vehicles to supply an appropriate therapeutic dose. The use of only a few therapeutically effective implantable vehicles containing a large number of cells provides simple retrievability which, for many applications, will be preferred over microsphere or other small configurations requiring a large number of vehicles. The immunoisolatory macrocapsule of the present invention is capable of storing 10,000 to 100,000 cells to as high as 500,000 cells or more, in individual or cluster form, depending on their type.

This invention also pertains to a method of isolating or protecting biologically active moieties, such as implanted cells, tissues, or other materials from immunological attack. The methods and vehicles of the instant invention are useful to deliver a wide range of cellular products, including high molecular weight products, to an individual in need of them, and/or to provide needed metabolic functions to an individual, such as the removal of harmful substances.

Products which can be delivered using the instant vehicle include a wide variety of factors normally secreted by various organs or tissues. For example, insulin can be delivered to a diabetic patient, dopamine to a patient suffering from Parkinson's disease, or Factor VIII to a Type A hemophiliac.

Other products which can be delivered through use of the instant vehicle include trophic factors such as erythropoietin, growth hormone, Substance P, and neurotensin. This invention is useful for treating individuals suffering from acute and/or chronic pain, by delivery of an analgesic or pain reducing substance to the individual. Such pain reducing substances include enkephalins, catecholamines and other opioid peptides. Such compounds may be secreted by, e.g., adrenal chromaffin cells. Another family of products suited to delivery by the instant vehicle comprises biological response modifiers, including lymphokines and cytokines. Antibodies from antibody secreting cells may also be delivered. Specific antibodies which may be useful include those towards tumor specific antigens. The release of antibodies may also be useful in decreasing circulating levels of compounds such as hormones or growth factors. These products are useful in the treatment of a wide variety of diseases, inflammatory conditions or disorders, and cancers.

The instant vehicle can also be used to restore or augment vital metabolic functions, such as the removal of toxins or harmful metabolites (e.g., cholesterol) from the bloodstream by cells such as hepatocytes. The method and vehicle of the instant invention make possible the implantation of cells without the concomitant need to immunosuppress the recipient for the duration of treatment. Through use of the biocompatible immunoisolatory vehicle, homeostasis of particular substances can be restored and maintained for extended periods of time. The instant vehicle may contain a multiplicity of cells, such that implantation of a single vehicle can be sufficient to provide an effective amount of the needed substance or function to an individual.

In one embodiment of this invention, methods are provided for the prevention or treatment of neural degeneration. Such neural degeneration occurs naturally as a result of the aging process, typically in physically mature individuals, or may occur as a result of a neurological disorder or disease. Examples of human diseases or disorders which are thought to be associated with neural degeneration include Alzheimer's disease, Huntington's chorea, AIDS-related dementia, and Parkinson's disease. These disorders, often occur in physically mature individuals. However, these and other neurological disorders may occur in juveniles.

As used herein, an "aged" individual is an individual in whom neural degeneration has occurred or is occurring, either as a result of the natural aging process, or as a result of a neurodegenerative disorder. Neural degeneration as a result of the natural aging process means loss or decline of neural function compared to a previous state not attributable to a defined clinical abnormality or neurological disorder, such as Alzheimer's, Parkinson's or Huntington's.

Animal models for neurodegenerative conditions are based on the premise that a specific insult may damage or kill neurons. In some cases this may even lead to a cascade of neuronal death which affects trophically interdependent neurons along pathways responsible for specific brain functions.

A strategy for treatment of neural degenerative condition involves the localized administration of growth or trophic factors in order to (1) inhibit further damage to post-synaptic neurons, and (2) improve viability of cells subjected to the insult. Factors known to improve neuronal viability include basic fibroblast growth factor, ciliary neurotrophic factor, brain-derived neurotrophic factor, neurotrophin-3, neurotensin, and Substance P.

In one animal model for neurodegenerative excitotoxicity, the glutamate analog, quinolinic acid, is injected stereotaxically into the brain region known as the striatum and/or basal ganglia to produce neuropathology and symptoms analogous to those of patients suffering from Huntington's disease. Both the model and actual Huntington's disease are characterized by damage to neurons necessary for aspects of motor control.

Furthermore, one of the early symptoms of Huntington's disease is loss of body weight (Sanberg, P. R. et al. *Med J Aust.* 1, pp. 407–409 (1981). Similar effects are also seen in the model system (Sanberg, P. R. et al. *Exp Neurol,* 66, pp. 444–466 (1979). Quinolinic acid is also found at abnormally high levels in AIDS-related dementia.

According to the present invention, trophic factors are provided to the proper brain region by implanting a vehicle containing living cells which secret an appropriate factor. Suitably, the cells are adrenal chromaffin cells which are known to secrete at least one factor, basic fibroblast growth factor. Other as yet unidentified trophic factors may also be secreted by chromaffin cells. It is to be noted that this embodiment of the invention is separate from the use of chromaffin cells to secrete the neurotransmitter, dopamine, for the amelioration of symptoms of Parkinson's disease. Nerve growth factor-secreting cells such as fibroblasts engineered to express NGF represent an alternative therapy for this quinolinic acid induced neurodegeneration. Schwann cells prepared from myelin may be encapsulated and implanted in appropriate brain areas to prevent neural degeneration associated with Parkinson's disease.

In another embodiment of the invention, the animal model involves lesion of the fimbria-fornix. In particular, neurons of the septohippocampal system are axotomized which leads to degeneration and cell death. This model is thought to be analogous to the types of lesions which cause Alzheimer's disease in humans. Suitably, a growth factor, nerve growth factor (NGF), is provided by the implantation of a vehicle containing cells which secrete NGF. Astrocytes immortalized (e.g. by transformation with the Large T antigen) and genetically engineered to express NGF may be employed. Preferably, the cells are fibroblasts which have been genetically engineered to produce recombinant NGF. The fibroblasts survive best in a core composed of a matrix material which mimics extracellular matrix, such as collagen or laminin-containing hydrogels. The core is surrounded by an immunoisolatory jacket which allows the diffusion of oxygen and nutrients to the cells in the core, and also allows the secreted NGF to diffuse through the jacket and into the body of the recipient. The vehicle implant inhibits the death of cholinergic neurons as assayed by the number of neurons which contain choline acetyl transferase (ChAT), an indicator of viable cholinergic neurons.

Fimbria-fornix lesions also cause behavioral deficits in the animal subjects of the model, most easily observed in tasks involving learning and memory. It has been reported that chronic administration of NGF to rats with fimbria-fornix lesions accelerates the animals' behavioral recovery (Wills, B. et al. *Behav.Brain Res.,* 17, pp. 17–24 (1985)). In the present invention, implantation of the vehicle containing NGF-secreting cells provides a practical way to deliver NGF continuously to the appropriate brain region of the lesioned animal. By analogy, the vehicle of the present invention offers a practical form of regenerative and/or prophylactic therapy for Alzheimer's victims whose conditions may be ameliorated by continuous delivery of NGF to specific brain regions.

A wide variety of biologically active moieties or cells may be used in this invention. These include well known, publicly available immortalized cell lines as well as primary cell cultures. Examples of publicly available cell lines suitable for the practice of this invention include, baby hamster kidney (BHK), chinese hamster ovary (CHO), mouse fibroblast (L-M), NIH Swiss mouse embryo (NIH/3T3), African green monkey cell lines (including COS-a, COS-7, BSC-1, BSC-40, BMT-10 and Vero), rat adrenal pheochromocytoma (PC12) and rat glial tumor (C6). Primary cells that may be used according to the present invention include, bFGF-responsive neural progenitor-stem cells derived from the CNS of mammals (Richards et al., *Proc. Natl. Acad. Sci. USA* 89, pp. 8591–8595 (1992); Ray et al., *Proc. Natl. Acad. Sci. USA,* 90, pp. 3602–3606 (1993)), primary fibroblasts, Schwann cells, astrocytes, β-TC cells, Hep-G2 cells, AT T20 cells, oligodendrocytes and their precursors, myoblasts, adrenal chromaffin cells, and the like.

Schwann cells maybe prepared according to the method of Bunge (PCT published application WO 92/03536), mixed with a suitable substratum such as Matrigel™, and encapsulated. The encapsulated cells may be implanted in appropriate areas of the brain to prevent the degeneration of the dopaminergic neurons of the nigral striatal pathway associated with Parkinson's disease. Generally, the preferred implant site will be in or near the striatum. Encapsulating the cells may enhance secretion of trophic factors since the cells will not be in proximal contact with neurons, and myelination will not occur. Other glial cell types may be encapsulated and implanted for this purpose, including astrocytes and oligodendrocytes.

The choice of biologically active moiety or cell depends upon the intended application. The encapsulated cells may be chosen for secretion of a neurotransmitter. Such neurotransmitters include dopamine, gamma aminobutyric acid (GABA), serotonin, acetylcholine, noradrenaline, epinephrine, glutamic acid, and other peptide neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

The encapsulated cells can also be chosen for their secretion of hormones, cytokines, growth factors, trophic factors, angiogensis factors, antibodies, blood coagulation factors, lymphokines, enzymes, and other therapeutic agents or agonists, precursors, active analogs, or active fragments thereof. These include enkephalins, catecholamines, endorphins, dynorphin, insulin, factor VIII, erythropoietin, Substance P, nerve growth factor (NGF), Glial derived Neurotrophic Factor (GNDF), platelet-derived growth factor (PDGF), epidermal growth factor (EGF), brain-derived neurotrophic factor (BDNF), neurotrophin-3 (NT-3), an array of fibroblast growth factors, and ciliary neurotrophic factor.

Alternatively, one or more biologically active molecules may be delivered into the capsule. For example, the capsule may contain one or more cells or substances which "scavenge" cholesterol, or other biological factors, from the host.

Techniques and procedures for isolating cells or tissues which produce a selected product are known to those skilled in the art, or can be adapted from known procedures with no more than routine experimentation. For example, islets of Langerhans can be isolated from a large-animal pancreas (e.g., human or porcine) using a combination of mechanical distention and collagenase digestion, as described by Scharp, D. W., et al., U.S. Pat. No. 4,868,121. Islets may be isolated from small animals such as rats by the method of Scharp, et al., Diabetes 29, suppl. 1, pp. 19–30 (1980). Similarly, hepatocytes can be isolated from liver tissue using collagenase digestion followed by tissue fractionation, as described by Sun, A. M., et al., Biomat., Art. Cells, Art. Org., 15, pp. 483–496 (1987). Adrenal Chromaffin cells may be isolated by the method of Livett, B. G., Physiology Reviews, 64, pp. 1103–1161 (1984).

Many cellular products which are difficult to provide using primary donor tissues can be provided using immortalized cells or cell lines. Immortalized cells are those which are capable of indefinite replication but which exhibit contact inhibition upon confluence and are not tumorigenic. An example of an immortalized cell line is the rat pheochromocytoma cell line PC12. Transformed cells or cell lines can be used in a similar manner. Transformed cells are unlike merely immortalized cells in that they do not exhibit contact inhibition upon confluence, and form tumors when implanted into an allogeneic host. Immortalization can allow the use of rare or notoriously fragile cell or tissue types for the long-term delivery of a chosen product or metabolic function. Suitable techniques for the immortalization of cells are described in Land H. et al., Nature 304, pp. 596–602 (1983) and Cepko, C. L., Neuron 1, pp. 345–353 (1988). Candidate cell lines include genetically engineered beta-cell lines which secrete insulin such as NIT cells (Hamaguchi, K., et al., Diabetes 40, p. 842 (1991)), RIN cells (Chick, W. L., et al., Proc. Natl. Acad. Sci. USA, 74, pp. 628–632 (1977)), ATT cells (Hughes, S. D., et al, Proc. Natl. Acad. Sci. USA, 89, pp. 688–692 (1992)), CHO cells (Matsumoto, M., et al, 1990, Proc. Natl. Acad. Sci. USA, 87, pp. 9133–9137 (1990)), and beta-TC-3 cells (Tal, M., et al, 1992, Mol. Cell Biol., 12, pp. 422–432 (1992)). Additionally, recombinant cells or cell lines can be engineered to provide novel products or functions and combinations thereof, using a wide variety of techniques well known to those of ordinary skill in the art.

For example, fibroblasts can be transfected with an expression vector for the chosen product (e.g., nerve growth factor, erythropoietin, insulin, or Factor VIII). It should be recognized however, that expression of a recombinant protein in a cell type which does not normally express the protein may lead to unregulated expression which may not be desirable for certain medical applications.

B-cell hybridomas secreting a selected monoclonal antibody, or T-cell hybridomas secreting a selected lymphokine, can also be used. It may be particularly desirable to deliver a monoclonal antibody or fraction thereof, which neutralizes the biological activity of a disregulated biological response modifier using the instant invention. Engineered cells which secrete soluble fragments of receptors for these biological response modifiers can be used in a similar fashion. The disregulation or overproduction of particular biological response modifiers has been implicated in the etiology of certain cancers.

The encapsulated material can be tissue or cells able to secrete such antinociceptive agents, including any one of catecholamines, enkephalins, opioid peptides or mixtures thereof. Preferably catecholamines are secreted, most preferably a mixture of catecholamines and enkephalins. Typically, the encapsulated material can be tissue of the adrenal medulla, or more particularly, adrenal medulla chromaffin cells. Additionally, genetically engineered cell lines or other naturally occurring cell lines able to secrete at least one pain reducing agent such as a catecholamine, enkephalin, opioid peptide, or agonist analog thereof, can be used.

If the cells to be immunoisolated are replicating cells or cell lines adapted to growth in vitro, it is particularly advantageous to generate a cell bank of these cells. A particular advantage of a cell bank is that it is a source of cells prepared from the same culture or batch of cells. That is, all cells originated from the same source of cells and have been exposed to the same conditions and stresses. Therefore, the vials can be treated as identical clones. In the transplantation context, this greatly facilitates the production of identical or replacement immunoisolatory vehicles. It also allows simplified testing protocols which assure that implanted cells are free of retroviruses and the like. It may also allow for parallel monitoring of vehicles in vivo and in vitro, thus allowing investigation of effects or factors unique to residence in vivo.

In all cases, it is important that the cells or tissue contained in the vehicle are not contaminated or adulterated. If a vehicle having a matrix core is desired, the cells are mixed under sterile conditions, with an appropriate amount of a biocompatible, gellable hydrogel matrix precursor. There are numerous natural and synthetic hydrogels which are suitable for use in a biocompatible immunoisolatory vehicle of the instant invention. Suitable naturally-derived hydrogels include plant-derived gums, such as the alkali metal alginates and agarose, and other plant-derived substances, such as cellulose and its derivatives (e.g., methylcellulose). Animal tissue-derived hydrogels such as gelatin are also useful. Alternatively, the core matrix can be made of extracellular matrix (ECM) components, as described by Kleinman et al., U.S. Pat. No. 4,829,000. Suitable synthetic hydrogels include polyvinyl alcohol, block copolymer of ethylenevinylalcohol, sodium polystyrene sulfonate, vinyl-methyltribenzyl ammonium chloride and polyphosphazene (Cohen, S. et al. *J. Anal. Chem. Soc.*, 112, pp. 7832–7833 (1990)).

The newly-formed immunoisolatory vehicle obtained by any of the methods described herein can be maintained under sterile conditions in a non-pyrogenic, serum-free defined nutrient medium or balanced salt solution, at about 37° C., prior to implantation. Lower temperatures (20° C.–37° C.) may be optimal for certain cell types and/or culturing conditions. Other holding temperatures and medium compositions consistent with good cell viability may also be used. Alternatively, the vehicle can be cryopreserved in liquid nitrogen, if a cryoprotective agent such as glycerin has been incorporated into the matrix (Rajotte, R. V. et al. *Transplantation Proceedings*, 21, pp. 2638–2640 (1989)). In such a case, the vehicle is thawed before use and equilibrated under sterile conditions as described above.

Implantation of the biocompatible immunoisolatory vehicle is also performed under sterile conditions. Generally, the immunoisolatory vehicle is implanted at a site in the recipient's body which will allow appropriate delivery of the secreted product or function to the recipient and of nutrients to the implanted cells or tissue, and will also allow access to the vehicle for retrieval and/or replacement. It is considered preferable to verify that the cells immobilized within the vehicle function properly both before and after implantation; assays or diagnostic tests well known in the art can be used for these purposes. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them.

The invention will now be further illustrated by the following examples, which are not to be viewed as limiting in any way.

EXAMPLE 1

Preparation of Cells For Immunoisolation

Cells derived from cell lines or from primary sources were maintained in vitro prior to immunoisolation. (In some cases, cells can be stored cryopreserved and then thawed and acclimated in vitro.) Conditions for incubation will vary for specific cell types, but will be readily ascertainable to those skilled in the art following no more than routine experimentation. Islets of Langerhans were obtained by the methods of Scharp et al.(supra) and maintained at 37° C. in an atmosphere of 5% $CO_2$-95% air in a medium consisting of a nutrient broth (e.g., Ham's F12 (GIBCO)), supplemented with serum (e.g., 25% v/v pooled equine donor serum). Islets were maintained in culture, using Petri dishes at 24° C. for predetermined periods of time, according to the method of Lacy, P. E. et. al., *Science*, 204, pp. 312–313 (1979). Prior to immunoisolation, the islets were collected, concentrated by swirling the Petri dish, resuspended in Hank's balanced salt solution (HBSS). The washed islets were resuspended in a sufficient volume of HBSS to yield the final islet density required to form an immunoisolatory vehicle containing the desired number of islets, of an appropriate size and shape for implantation and subsequent restoration of normoglycemia to a diabetic individual. This method of preparing the cells prior to immunoisolation is thought to remove antigen presenting cells from the islet tissue thus diminishing immunologic attraction to the outside of the vehicle which could limit its function and duration.

EXAMPLE 2

Formation of Hydrogel Matrices with Different Molecular Weight Cutoffs

An alginate thin film made from a solution of 1.0% w/v sodium alginate in $H_2O$ was cross-linked for 6 minutes using either (1) a 1.0% (w/v) or (2) a 2.0% (w/v) aqueous $CaCl_2$ solution. The sheet was made by placing a film of liquid on a glass plate using a draw down blade with a 0.2 mm clearance, then immersing in the aqueous $CaCl_2$ solution. A disk was cut from the film using a 47 mm cutting die. The disk was placed in an Amicon stirred filtration cell and used to filter solutions of several marker solutes under a pressure of 10 psi. The concentration of the marker solute was measured in the retentate ($C_r$=average of initial and final retentate concentration) and similarly in the bulked permeate ($C_p$). The rejection coefficient of each hydrogel was calculated as follows:

$$R = 1 - C_p/C_r$$

Thus, a solute which is completely rejected would have a coefficient of 1, and conversely, one which is completely passed through the hydrogel would have a coefficient of 0. The hydrogel resulting from (1) was permeable to 2,000 kD Dextran (Poly Sciences corp.) (rejection coefficient equal to 0.64). The hydrogel resulting from (2) was nearly impermeable to the same Dextran solution. FIG. 1 describes permeability of the two hydrogels to the following additional solutes. Bovine Serum Albumin (BSA; ICN Biochemicals), Vitamin B12 (ICN Biochemicals), α-chymotrypsin (ICN Biochemicals), Apoferritin (Sigma). The approximate molecular weights are given in parenthesis in FIG. 1.

EXAMPLE 3

Formation of a Dual-Matrix Immunoisolatory Vehicle

A 2% solution of sodium alginate in physiological saline (PS; 150 mm NaCl) was prepared under sterile conditions. A sterile suspension of pancreatic islets in CRML1066 (GIBCO) culture media isolated from adult rats was diluted 1:1 with the alginate solution, for a final concentration of 1% alginate in the islet suspension. The islet suspension was extruded from a single chamber extrusion nozzle into a 1% $CaCl_2$ bath. Once the alginate polyions were crosslinked (approx. 2 min.) and the core containing immobilized islets formed, the core was placed in a 2% alginate solution. The core was then drawn up into tubing with a diameter approximately 500 microns larger then the core and reextruded into a second crosslinking bath of 2% alginate, surrounding the core with a jacket formed of a separate cell-free layer of alginate matrix cross-linked to the core. The thus formed macrocapsule was cylindrical with dimensions of 30 mm length, 800 mm core diameter, and 1 mm diameter core to jacket. The core volume was 15 mm. The core contained 300 islets constituting a volume fraction of 10.6% of the total core volume.

EXAMPLE 4

Formation of a Dual-Matrix Immunoisolatory Vehicle by Coextrusion

A 2% solution of sodium alginate in physiological saline (PS; 150 mm NaCl) was prepared under sterile conditions. A sterile suspension of pancreatic islets in CRML1066 culture media isolated from adult rats was diluted 1:1 with the alginate solution, for a final concentration of 1% alginate in the islet suspension.

The islet suspension was loaded into the inner chamber of a nested dual-bore coextrusion device of the configuration described previously, the inner bore of which has a diameter of 500 microns and the peripheral bore of which has a diameter of 600 microns. The outer chamber of this device was loaded with a solution of sterile 1% sodium alginate in PS.

The tip of the nozzle was immersed in a bath containing a sterile solution of 1% $CaCl_2$ in PS, which induces the hardening or gelling of alginate by crosslinkage of alginate polyions. The materials loaded into the chambers were coextruded into this bath, generating a continuously forming alginate cylinder containing a core region of alginate matrix-immobilized islets and a surrounding region of alginate matrix free of islets. The outer diameter of the jacket was 1.2 mm. The inner diameter of the core was 1.0–1.05 mm. The total islet volume of the core was 0.8 $mm^3$ (200 islets). The total core volume was 25.98 $mm^3$. The volume of the islets was 3% of the total core volume. The MWCO for 1% alginate was as depicted in FIG. 1. However, the MWCO will increase with time. similarly to FIG. 7 due to continued $Ca^{++}$ displacement. The alginate of the core was cross-linked with the alginate of the jacket.

The relative thickness of the surrounding region was modified by adjusting the speeds at which the materials were extruded from the core and peripheral bores of the nozzle. In general as flow in the core increased, wall thickness decreased. As flow in the peripheral bore was increased wall thickness increased, Ranges of flow rates used were the same for both the core and periphery (0.3–1.5 ml/min.). The ends of the cylinder were sealed by dipping the cylinder first in a sterile 2% sodium alginate bath, then in a sterile 1% $CaCl_2$ bath. The immunoisolatory vehicle so formed was maintained in sterile tissue culture medium prior to implantation.

EXAMPLE 5

Formation of Core Matrix, Permselective Membrane Immunoisolatory Vehicle BV Coextrusion A suspension of rat islets in 1% alginate was prepared as described in Example 3 and loaded into the inner chamber of the coextrusion device. The outer chamber was loaded with a membrane casting solution comprising 12.5% (w/w) PAN/PVC in DMSO (i.e., dimethyl sulfoxide). The tip of the nozzle was either positioned at a fixed distance above, or immersed in, a bath containing a sterile solution of 1% $CaCl_2$ in PS, which induced the hardening or gelling of the alginate core matrix, and simultaneously induced the hardening of the casting solution into a permselective membrane. The exterior surface characteristics of the vehicle were determined by whether the nozzle had been positioned above or below the surface of the bath. When the nozzle was positioned above the bath and exposed to low relative humidity (RH) air, an anisotropic membrane with a rough, coriaceous (i.e., leathery) external surface was formed, but when the nozzle was immersed in the bath, a membrane-bilayer with a smooth external surface was formed. Alternatively, when the nozzle was placed above the bath and the fiber exposed to high RH air, an intermediate was formed. The materials loaded into the chambers were coextruded into this bath, generating a continuously forming cylindrical vehicle, comprising a core region of alginate matrix-immobilized islets and a surrounding semipermeable membrane having a MWCO of 50 kD.

The relative thickness of the membrane was modified by adjusting the relative velocity of extrusion from the bores, as described in Example 3. The ends of the cylinder were sealed using methods similar to those described in the copending U.S. patent application Ser. No. 07/461,999 filed Jan. 8, 1990, the teachings of which are herein incorporated by reference. The immunoisolatory vehicle so formed was maintained in sterile PS, a balanced salt solution or tissue culture medium prior to implantation.

EXAMPLE 6

Formation of Core Matrix, Permselective Membrane Immunoisolatory Vehicle by "Hand Loading"

In other cases, the islets were suspended in a 1–2% alginate solution, and "hand loaded" into preformed thermoplastic hollow fibers using a syringe and the ends of the fibers were sealed by a combination of heat and polymer glue precipitation as described in copending U.S. Ser. No. 07/461,999. The MWCO of the thermoplastic jacket was approximately 50 kD. The hydrogel matrix was formed by incubating the loaded fibers in a 1% calcium chloride solution for 6 minutes.

EXAMPLE 7

Assessment of Viability and Function of Immobilized, Immunoisolated Islets in vitro Adult rat islets immunoisolated within double matrix vehicles by the methods described in Examples 3 and 6. Matrix liquid core vehicles with thermoplastic jackets were incubated in vitro for at least two weeks. The vehicle had a core outer diameter of 800 $\mu$m overlain with a wall thickness of 65 $\mu$m. Alginate/Alginate dual matrix vehicles had an 880 $\mu$m core diameter and 60 $\mu$m wall thickness. Incubation conditions were: immersion in Ham's F12 medium supplemented with 25% equine serum at 37° C. in a 5%$CO_2$-95% air atmosphere. The medium was refreshed every three to four days.

Using propidium iodide, the immunoisolated islet cells were found to be 95% viable after this incubation period in vitro. They were shown to remain functional as well. When tested by perfusion with glucose (Dionne, supra) immunoisolated islets were shown to have an insulin secretory response similar both in magnitude and pattern to that of unprotected islets incubated in vitro for a similar period of time and under similar conditions. Insulin release was measured by the method of Soeldner, J. S. et al. *Diabetes,* 14, p. 771 (1965). The results of a typical perfusion experiment are shown in FIGS. 2A and 2B. The challenge and baseline concentrations of glucose used were 300 mg% and 100 mg%, respectively. No significant delay in either the onset of the first phase of insulin release following glucose stimulation or return to baseline secretion was observed with immunoisolated islets. In addition, a rising second phase comparable to that of unprotected islets was seen. Expressed on a per-islet basis, the total amounts of insulin released by immunoisolated islets were similar to that for unprotected islets. These results are summarized in FIGS. 3A and 3B.

EXAMPLE 8

Comparison of in vivo Performance of Xenografted Islets Isolated within Vehicles Having a Thermoplastic Membrane with and without an Internal Hydroael Matrix Rat islets were immunoisolated in either matrix or liquid core thermoplastic vehicles as described in Example 6. Vehicle dimensions were 800 µm O.D., 55 µm wall thickness, 2 cm fiber length. Just under 20% loading density was used. In the case of liquid core capsules, alginate was not included in the cell suspension. In the first experiment, islets were immunoisolated within a matrix. Vehicles were implanted intraperitoneally into streptozotocin-induced diabetic mice for a concordant xenograft (i.e., between closely-related species). Free-floating implants were inserted into the peritoneal cavity. Eight animals were implanted with 500–1000 immunoisolated rat islets each. One animal showed no amelioration of hyperglycemia. The others returned to a normoglycemic state (i.e., the plasma glucose levels of these animals returned to a normal range defined as 100–125 mg%) within five days posttransplantation and remained normoglycemic until day 60 when the grafts were removed and the animals again became hyperglycemic. The average results of 7 such experiments are summarized in FIG. 4. The absence of significant fluctuations in plasma glucose levels in these animals should be noted. The recovered immunoisolatory vehicles were inspected for evidence of fibrotic overgrowth, and were assessed for the ability to release insulin in response to glucose perfusion. None of the vehicles had become completely encapsulated with fibroblasts, however in some areas three to five layers of fibroblasts around the exterior of the vehicle were observed. Recovered immunoisolatory vehicles released insulin in vitro following perfusion in response to glucose and theophylline stimulation and histological analysis revealed viable islets with evidence of insulin staining within the cells. The results of the perfusion experiment with glucose and theophylline stimulation are shown in FIG. 5.

These favorable results contrasted sharply with those obtained when rat islets were immunoisolated within a PAN/PVC membrane without an immobilizing matrix. For these immunoisolatory vehicles, functional responsiveness lasted only 12±3 days post implantation; five out of five animals tested returned to a hyperglycemic state thereafter. Histological examination of these immunoisolatory vehicles revealed agglomeration of the islets. The islets had condensed into a large mass of tissue which exhibited severe central necrosis, with only a rim of viable and identifiable islet cells surviving. Thus, the presence of a matrix to prevent islet aggregation and resulting cell death, significantly improved viability resulting in long term efficacy of the implant.

EXAMPLE 9

Assessment of the Restoration of Normoglycemia to Streptozotocin-Induced Diabetic Mice by Implantation of Immunoisolated Concordant Xenograft Islets in Immunoalobulin Permeable Vehicles In vivo performance of the double-matrix immunoisolatory vehicle was assessed using the rat-to-mouse concordant xenograft model for restoration of normoglycemia to streptozotocin induced diabetic mice. The vehicles were prepared as in Example 3 and have significant permeability to 2,000 kD Dextran (FIG. 1). Therefore, these vehicles were also readily permeable to IgG (150 kD). The results of this experiment are summarized in Table 2. The animals were divided into three groups: group 1 consisted of seven control animals into whom 300 nonimmunoisolated islets per animal were implanted at the kidney subcapsular site. Only one of these animals showed amelioration of hyperglycemia for more than 12 days. The mean duration of normoglycemia in Group 1 was 14.0±3.1 days.

Group 2 consisted of thirteen animals each implanted with 300 rat islets immobilized in an alginate matrix lacking a surrounding cell-free region. Graft function was lost within 24 days in 8/13 of these Group 2 animals, indicating that simple immobilization conferred no advantage over the Group 1 controls. The other five animals remained normoglycemic until the graft was removed. The mean duration of normoglycemia in group 2 was 29.3±5.5 days.

Group 3 consisted of ten animals, each implanted with 300 rat islets immobilized within a dual-matrix immunoisolatory vehicle of the configuration described in Example 3, i.e., with a surrounding layer of cell-free alginate matrix. In only four of these animals, graft function was lost within 14 days postimplantation. However, six animals remained normoglycemic beyond 100 days at which time the experiment was terminated and the grafts removed, precipitating a return to the diabetic state (FIG. 6). The mean duration of normoglycemia in group 3 was 65.8±15.1 days (n=10). Fibromatous reaction to the recovered alginate vehicle was minimal. Histological analysis of recovered immunoisolated islets revealed viable islets with evidence of insulin staining within the β cells. The immunoisolatory vehicles used in this experiment also demonstrate the functionality and biocompatibility of vehicles which are permeable to high molecular weight proteins such as the immunoglobulin G protein.

TABLE 1

SURVIVAL OF IMMUNOISOLATED XENOGRAFTS IN DIABETIC MICE

| | | Survival (Days) | |
|---|---|---|---|
| Group | Vehicle | Individual | Group |
| 1 | control | 7, 12, 12, 12, 12, 12, 29 | 14.0 ± 3.1 |
| 2 | immobilized | 8, 12, 12, 14, 15, 16, 18, 24, 41*-, 53*, 54*, 54*-, 60*- | >29.3 ± 5.5 |
| 3 | immuno-isolated | 8, 8, 12, 13, 102*-, 102*-, 102*-, 102*-, 104*-, 104*- | >65.8 ± 15.1 |

*Nephrectomy for removal of islet graft

A vehicle of the configuration described in Example 3 was prepared; it contained several hundred islets and had a membrane MWCO of less than 50 kD.

The vehicle was implanted into a diabetic BB rat. This strain of rat is known to be a rodent model for mimicking human Type 1 autoimmune diabetes. The vehicle was recovered after a 21-day period of residence in vivo. The immunoisolated islets were found to be viable and functional, as determined by histological analysis.

EXAMPLE 10

Assessment of the Survival of Immunoisolated Islets in a Discordant Xenogenic Recipient Dual matrix immunoisolatory vehicles containing immobilized rat islets were prepared by the process of coextrusion from a nested dual-bore nozzle as described in Example 4. The conditions for the gelling of the matrix were chosen to yield a hydrogel matrix permeable to 2,000 kD blue Dextran (as in FIG. 7), thus the vehicle so formed was permeable to immunoglobulin G and to C1q.

Segments of about 0.5 cm in length were prepared from the continuous cylindrical vehicle by periodically interrupting the flow of the core material to form cell free regions, which were readily visible. The fiber was cut in the cell free region; thus the cells were completely surrounded by a region of cell-free alginate matrix. The vehicles were implanted between the leaves of the mesentery of guinea pigs (n=2), a discordant (i.e., distantly related) host. After 21 days of residence in vivo, the vehicles were removed and tested in vitro for glucose-responsive insulin release. These results are summarized in FIG. 8. Following basal stimulation, a statistically significant rise in insulin release from the immunoisolated islets was measured when stimulated with 300 mg/dl glucose. A return to basal insulin levels occurred when glucose returned to 100 mg/dl. Thermoplastic vehicles with alginate cores gave similar results.

EXAMPLE 11

Improved Tissue Viability by Controlled Reaggregation

Purified canine islets, prepared according to the method of Scharp and Lacy, U.S. Pat. No. 5,079,160, were dispersed into cell aggregates containing from one to 50 cells according to the following protocol. 1000 canine islets were rinsed 3 times with 50 ml of Ca++ and Mg++ free Hanks medium containing 1 mm EDTA. After the final rinse, islets were centrifuged into a pellet at 100×g for 8 min., 10° C. The resulting pellet was resuspended in 5 ml of the same medium per 1000 islets. This slurry was agitated for 8 min. at 24° C. using a hand held micro-pipet. At the end of 8 min., trypsin and DNAse were added to final concentrations of 25 ug/ml and 2 ug/ml respectively. The slurry was further agitated by repeated pipetting for approximately 5 min at which time microscopic examination indicated that the largest aggregates consisted of no more than about 50 cells. The digestion was quenched by adding 10 ml of cold DMEM with 10% new born calf serum per 1000 islets. Aggregates were pelleted by centrifugation at 250×g for 6 min. Aggregates were cultured in Ham's F12 with 25% horse serum overnight during which time limited reaggregation occurred resulting in a volume average aggregate size of approximately 35 um.

Following overnight culture, aggregates were pelleted by centrifugation at 250×g for 6 min. A 2% solution of non-crosslinked alginate was added to the pellet to make a solution consisting of 1% alginate and 8% tissue (w/v). The final islet volume of the core was 0.56 mm$^3$ in the form of aggregates evenly dispersed throughout the viscous liquid. The tissue slurry was aseptically aspirated into a length of Pe 90 tubing the end of which was previously necked down so as to fit into the lumen of 670 µm inner diameter hollow fiber membranes (outer diameter=800 µm. Ten microliters of tissue containing slurry was injected into each of several PAN/PVC fibers of 2 cm length. The ends of each fiber were sealed as described previously and the fibers were stored overnight in Ham's F12 with 25% horse serum. Prior to implantation, fibers were placed into fresh Hanks without serum for 1 hour in order to remove serum residue.

After overnight culture, ½ of the vehicles were implanted into the peritoneal cavity of normoglycemic rats (2 vehicles per animal) and ½ of the vehicles were maintained in in vitro tissue culture. After 2 weeks, implanted vehicles were removed from the peritoneal cavity and subjected to an in vitro glucose challenge along with control vehicles cultured in vitro. Explanted vehicles exhibited insulin release that was as good as or better than that seen prior to implantation indicating functional survival not only of insulin release but of glucose sensitivity. Following glucose challenge, the alginate core of the vehicles was "blown out" and the tissue was stained with PI for viability. Although each aggregate had pulled together to form a tight spheroid of approximately 35 um in diameter, individual aggregates remained well distributed throughout the alginate core and had not clustered together to form necrotic regions. Failure to stain with PI stain indicated 100% viability.

EXAMPLE 12

Partial Restoration of Motor Behavior upon Implantation of Immunoisolated Adrenal Chromaffin Cells in an Experimental Model of Parkinsonism Bovine adrenal chromaffin cells were recovered from adrenal glands according to the method of Livett B. G. *Physiol. Rev.*, 64, pp. 1103–1161 (1984) by collagenase digestion and maintained in culture for 10 days to ensure lack of bacterial or fungal contamination. Clumps of chromaffin cells were washed in serum-free medium by centrifugation and resuspended in 1% alginate solution. This cell suspension was used to form a matrix-core, thermo-plastic membrane immunoisolatory vehicle by co-extrusion as described in Example 4. The aqueous precipitation bath comprised a solution of 1% $CaCl_2$ mixed 1:2 with tissue culture medium for a final concentration of 0.5 % $CaCl_2$ in the bath. The fiber was incubated in the bath for 6 minutes to allow the alginate to gel, and was then transferred to a petri dish containing Dulbecco's modified Eagle's medium (DMEM). The fiber was visually inspected for regions with good wall morphology, then spot-checked for the presence of chromaffin cells. It was then divided into 4 mm long sections by sealing the ends of the sections with a combination of heat, solvent, and pressure.

Eight Sprague-Dawley rats received injections (10 µg/5ul) of 6-hydroxydopamine (6-OHDA) into the substantia nigra. They were tested for apomorphine-induced (0.1 mg/kg) rotational behavior at weekly intervals. By the method of Ungerstedt V. U., *Acton. Physiol. Scand. Suppl.*, 367, pp. 69–93 (1971) and Ungerstedt V. U., *Brain Res.*, 24, pp. 485–493 (1970). Apomorphine induces the Parkinson's-like motor response of turning away from the side of the 6-OHDA-induced lesion. The extent of such rotational motor behavior upon apomorphine injection can be used to monitor the extent of the lesion and the degree of amelioration provided by the immunoisolated chromaffin cells. Six weeks after the induction of Parkinsonism, the animals received intrastriatal implants of either control (empty) or adrenal-chromaffin cell-containing vehicles, and were again tested for rotational behavior at weekly intervals. These results are summarized in FIG. 9.

Prior to implantation, all animals exhibited an equivalent number of rotations following apomorphine challenge. Within two weeks postimplantation, however, those animals receiving immunoisolated adrenal chromaffin cells exhibited a significant 35–40% percent decrease in rotations which remained stable throughout testing; this indicates that the implants significantly reversed the effects of 6-OHDA-induced lesions. The animals who received control vehicles did not show any reduction in the number of rotations.

EXAMPLE 13

Implantation of Adrenal Chromaffin Cells for Prevention of Neural Damage due to Excitotoxicity (Huntington's Disease Model)

This example sets forth a method for prevention of neural damage due to neural excitotoxicity in a subject by implantation of a vehicle containing cells which secrete a trophic factor. This animal model of neuroexcitotoxicity is considered analogous to the types of neural damage suffered by patients with Huntington's disease.

Subjects

Male Sprague-Dawley rats (N=23) 90–120 days old and weighing approximately 225–250 grams were used in the following experiments. All animals were housed groups of 2–3 in a temperature and humidity controlled colony room maintained on a 12 hour light/dark cycle with lights on at 0700 hours. Food and water were freely available during testing.

Preparation of Adrenal Cell-Containing Macrocapsules

Bovine adrenal chromaffin cells were isolated from adrenal glands and maintained in culture for 10 days to ensure lack of bacterial or fungal contamination. Clumps of chromaffin cells were washed in serum-free medium by centrifugation and resuspended in 1% alginate solution. This cell suspension was used as the bore solution for coextrusion in 15% PAN/PVC:DMSO solution. The coextruded fiber containing chromaffin cells was collected in a bath of 1% $CaCl_2$ mixed 1:2 with tissue culture medium. The fiber was left in that solution for 6 minutes to allow the alginate to gel, and was then transferred to a petri dish containing medium. Fiber was visually inspected for regions with good wall morphology, then spot-checked for the presence of chromaffin cells. Capsules were made by sealing the ends of 4 mm long sections with a combination of heat, solvent, and pressure. Capsules were then implanted stereotaxically into the brains of Sprague Dawley rats.

Preparation of Quinolinic Acid

Quinolinic acid (Sigma Chemical Co) was dissolved in 2N sodium hydroxide and diluted with phosphate buffer at pH 7.2 to a final pH of 7.4 and concentration of 225 nmole/1 ul.

Surgical Procedure

Rats were anesthetized with sodium pentobarbital (45 mg/kg) and positioned in a Kopf stereotaxic apparatus. A sagittal incision was made in the scalp and a hole drilled in the skull for placement of the macroencapsulated adrenal chromaffin cells. Capsules were placed in a capillary tube mounted to the stereotaxic device and lowered to the following coordinates: 0.3 mm anterior to Bregma, 3.5 mm lateral to the sagittal suture and 7.5 mm ventral from the surface of the brain.

One week later, the animals were anesthetized and mounted in the stereotaxic instrument prior to intrastriatal administration of quinolinic acid or the phosphate buffer vehicle. Solutions were slowly infused (0.125 ul/minute) using a 10 ul Hamilton syringe) through a hole drilled 0.8 mm lateral to the site of placement of the capsule. The injection site for quinolinic acid was: 0.3 mm anterior to Bregma, 2.7 mm lateral to the sagittal suture, and 5.5 mm ventral from the surface of the brain. A total volume of 1.0 ul was delivered and the injection cannula was left in place for an additional 2 minutes to promote the local diffusion of the perfusate. This procedure resulted in the formation of 3 experimental groups: adrenal capsule/quinolinic acid (N=8), empty capsule/quinolinic acid (N=8), quinolinic acid only (N=7).

Body weights were recorded on a daily basis for 15 days following quinolinic acid administration.

Histology

Thirty days following quinolinic acid administration, animals were transcardially perfused using a peristaltic pump, with 0.9% saline (50 ml/min) followed by 1% paraformaldehyde/1.25% glutaraldehyde in 0.1M phosphate buffer (4° C.) (800 ml/30 minutes). The brains were then postfixed for 2 hours in the paraformaldehyde solution prior to being placed in 20% sucrose for 24 hours. The brains were then frozen and serially cut on a sliding microtome into 30 um coronal sections. Sections were then processed for cytochrome oxidase histochemistry and adjacent sections were stained for Nissl.

Results

The presence of cytochrome oxidase was considered indicative of metabolic activity, and thus of neuronal viability. Nissl staining was used to visualize the cell processes and to assess the general structure of the neural architecture.

In the experimental group that received empty capsules, the striatum was shrunken 20–40% as compared with the lesioned animals that had received vehicles containing chromaffin cells. The striatal neurons of the empty capsule group showed lack of metabolic activity as demonstrated by the absence of staining for cytochrome oxidase. Furthermore, all animals showed significant decrease in body weight (FIG. 10).

In contrast, the neurons of the group which received vehicles containing chromaffin cells showed normal staining with both cytochrome oxidase and Nissl, and no loss of body weight.

Conclusion

The neurons of subjects which received chromaffin cell-containing implants were protected from excitotoxic damage caused by quinolinic acid.

EXAMPLE 14

Treatment of Neural Degeneration in Rats using Encapsulated Genetically Engineered Fibroblasts This example sets forth a method of treatment for animals with a fimbria-fornix lesion. This type of lesion produces neuron cell death and degeneration of post-synaptic neurons and behavioral symptoms indicating deficits in memory and learning. The degeneration of cholinergic neurons produced in this animal model are considered analogous to similar effects seen in Alzheimer's disease in humans.

Surgical Procedure

Adult male Sprague-Dawley rats (250–350 g) were anesthetized by intraperitoneal injection of sodium pentobarbital (55 mg/kg). Unilateral fimbria-fornix lesions were performed by aspiration of the fimbria, dorsal fornix, medial part of the parietal cortex, ventral hippocampal commissure, corpus callosum, and overlying cingulate cortex. An implant vehicle as described below was then placed into the ipsilateral lateral ventricle of each animal, oriented perpendicular to the interaural plane.

Preparation of PAN/PVC Fibers

Permselective hollow fibers were prepared via the dry jet-wet spinning technique. Cabasso, Hollow Fiber Membranes, vol. 12, *Kirk-Othmer Encyclopedia of Chemical Technology*, Wiley, N.Y., 3rd Ed., pp. 492–517 (1980). A 15% solution of PAN/PVC copolymer in dimethylsulfoxide (DMSO) was extruded through an annular spinneret, with solvent DMSO (for a porous inner surface) or nonsolvent water (for a smooth skinned inner surface) flowing through the bore. The resulting fiber was collected into a nonsolvent water bath, glycerinated, and dried.

Genetically Engineered Fibroblasts

R208N.8 and R208F rat fibroblasts were a gift of Dr. Xandra Breakefield, Harvard University. R208N.8 fibroblasts were engineered to secrete NGF as follows (Short et al., *Dev. Neurosci.*, 12, pp. 34–45 (1990)). A retroviral vector was constructed from Moloney murine leukemia virus. It contained the last 777-basepairs of the coding region for mouse NGF cDNA under control of the viral 5' long terminal repeat. The vector also included a dominant selectable marker encoding the neomycin-resistance function of transposon Tn5 under control of an internal Rous sarcoma virus promoter. Transmissible retrovirus was produced by transfecting vector DNA into PA317 amphotropic producer mouse fibroblast cells and by using medium from these cells to infect Ψ2 ecotropic cells. Virus from the Ψ2 clone producing the highest titer was used to infect the established rat fibroblast cell line R208F, transforming it to R208N.8. Individual neomycin-resistant colonies, selected in medium containing the neomycin analog G418, were expanded and tested for NGF production and secretion by a two-site enzyme immunoassay.

Encapsulation of Fibroblasts

R208F and R208N.8 fibroblasts were dissociated with Trypsin-EDTA, and suspended at a density of $1 \times 10^6$ cells/µl in a laminin containing matrigel resuspended in Matrigel™ or Vitrogen™, and aspirated with a 1 cc syringe into a pre-sterilized PAN/PVC hollow fiber. Fibers were cut to 4 mm length, and the fiber ends were heat sealed with a sterile surgical cautery.

ChAT Immunocytochemistry

After two weeks, the animals were sacrificed, fixed by transcardial perfusion with cold heparinized physiologic saline and 4% paraformaldehyde in phosphate buffer. The brains were immediately dissected and postfixed overnight, followed by immersion in 15% and 25% buffered sucrose solutions. Frozen sections were cut at 25 µm from anterior to posterior on a cryostat, and all coronal sections were collected onto slides or into phosphate buffer. Representative coronal sections were processed for immunocytochemistry using a monoclonal antibody to rat ChAT (2.5 µg/ml) with the biotin-avidin-DAB method. Sections were mounted and neuronal cell bodies counterstained with cresyl violet. All ChAT-positive cell bodies were counted in the medial septum and vertical diagonal band region ipsilateral and contralateral to the lesion, between the genu of the corpus callosum and the decussation of the anterior commissure. A significant prevention of ChAT(+) cell reduction was observed in rats receiving R208N.8 capsules.

EXAMPLE 15

Use of an Immunoisolatory Vehicle to Deliver a High-Molecular Weight Product to a Recipient Immunoisolatory vehicles were prepared by hand loading 350,000 hybridoma cells producing an antibody (iostype immunoglobulin G), specific for tumor necrosis factor (TNF) into a 7 mm length of a medical grade, olefinic microporous hollow fiber of the kind used for plasmapheresis (Plasmaphan; Enka). The internal diameter of the fiber was 300 microns; its MWCO was about 1,000 kD. The ends of the vehicle were sealed as described in copending U.S. Ser. No. 07/461,999. The vehicle was implanted under the renal capsule of a mouse, where it was allowed to reside for 14 days. The vehicle was thereafter recovered and found to contain many cells, over 50% of which were viable as determined by the exclusion of indicator dye (pI). The release of TNF-specific antibody into the serum of the recipient mouse was monitored by ELISA. The results are summarized below:

TABLE 2

| Days Post Implantation | Titer of TNF Specific Antibody in vivo |
| --- | --- |
| 0 | none detected |
| 1 | 10 |
| 2 | 30 |
| 6 | 70 |
| 8 | 100 |
| 11 | 60 |
| 15 | 23 |

A control immunoisolatory vehicle maintained in vitro exhibited similar antibody release.

EXAMPLE 16

Subcutaneous Implantation of Encapsulated Islets

Preparation of Islet Containing Capsules

Two types of acrylic copolymer hollow fibers, designated Type 1 and Type 2 fibers, were used. Fibers were formed by using a dry-wet spinning technique with a spinneret as described in Cabasso, Hollow Fiber Membranes, vol. 12, *Kirk-Othmer Encyclopedia of Chemical Technology*, Wiley, N.Y., 3rd Ed., pp. 492–517 (1980). The acrylic co-polymer used was poly(acrylonitrile-co-vinyl chloride)($M_n$=100,000, $M_w$=300,000 as measured by size-exclusion chromatography; CytoTherapeutics, Inc.) dissolved in dimethyl sulfoxide (12.5% w/w). The acrylic copolymer solution was pumped through the outer tube of the spinneret and water was pumped through the inner tube. Type 1 hollow fibers were extruded into water through an air gap, resulting in a fenestrated outer wall typical of fibers made by a dry-wet spinning technique. The type 2 fibers were made in a analogous fashion, except the air gap was replaced by a humidified atmosphere, resulting in a smooth outer surface.

Rat islets were isolated from male Wistar-Furth rats as described in Example 1 above. The islets were immobilized in alginate gel and encapsulated into 2-cm type 1 or type 2 fibers, 550 or 1000 islets per fiber, as described in Lacy, P. E., et al., *Science*, 254, p. 1782 (1991).

Implantation

The encapsulated rat islets were implanted intraperitoneally or subcutaneously in mice made diabetic by the injection of streptozotocin. Non-fasting plasma glucose concentrations were determined three times weekly; the diabetic recipients had concentrations greater than 400 mg/dl before transplantation. The loading density was 70 islets per centimeter for 1000 islets and 35 islets per centimeter for 500 islets. Twenty-six mice received fibers intraperitoneally, and 26 received fibers subcutaneously. In each group, 14 mice received fibers containing a total of 1,000 islets and 12 received fibers containing a total of 500 islets.

Results

The intraperitoneal type 1 fibers induced and maintained normoglycemia for greater than 60 days in seven of nine recipients that received 1000 islets and in all of the recipients receiving 500 islets. None of the recipients of subcutaneous type 1 implants of 500 islets remained normoglycemic for 60 days; three of eight recipients of 1000 islets were normoglycemic for greater than 60 days. Removal of the fibers from these three recipients returned the mice to a diabetic state. Transplants of rat islets in the type 2 fibers produced and maintained normoglycemia in the recipient mice in greater than 80% of either the intraperitoneal or subcutaneous sites with either 1000 or 500 islets. The recipients became hyperglycemic again when the fibers were removed at 60 days. Histologic examination of the removed type 1 and type 2 fibers revealed that they were biocompatible.

EXAMPLE 17

Controlled Reaggregation of Rat Islets

Rat islets were isolated, dissociated, reaggregated and encapsulated as described in example 11, with the exception that sealed fibers were not exposed to serum in vitro and were held for only 1 hour prior to implantation. Either two 2 cm long capsules or two 2 cm and one 1 cm capsules were implanted in each rat.

Islets were dissociated and reaggregated to an approximate size of 35 $\mu$m. All the reaggregated cells from approximately 500 islets were loaded into each 4–6 cm length capsule. Implanted capsules are capable of maintaining normoglycemia in rats for greater than 60 days.

EXAMPLE 18

Fabrication of Flatsheet Islet Encapsulation Vehicles

Aseptic materials and methods were used in all the following procedures. This included autoclave sterilization, EtOH sanitization, UV sterilization and /or 0.2 um sterile filtration.

Casting solution was prepared using a monoacrylic copolymer with an average molecular weight of $10^5$ daltons which was dissolved in a water-soluble, organic solvent. The casting solution was 10.0% w/w polymer in the organic solvent. The polymer was precipitated once under sterile conditions prior to its use to remove any residual monomers, oligomers, or any additives placed in the bulk polymer by the manufacturer. This polymer solution was then dried and redissolved in 100% DMSO to form a 10% w/w polymer solution. This solution was passed through a 0.2 um sterile nylon filter and collected under aseptic conditions.

Next the casting solution was uniformly spread using a casting bar over a ¼" glass substrate at a casting thickness of 125 um. In order to cast the film, the substrate, held at a 30 degree incline, was moved under the stationary casting bar into the precipitation bath. The level of the precipitation bath was between ⅛–¼' from the casting bar. The substrate can be any material which prevents premature lifting of the membrane from the substrate prior to complete precipitation. Simultaneous with spreading, the casting solution was plunged into 2420 C. water resulting in precipitation of the polymer forming an anisotropic semipermeable membrane, with the permselective layer appearing as a thin skin on the quench side (away from substrate) of the membrane. The film was left in the bath for four minutes to insure that membrane properties have been adequately established prior to its removal.

The film was then carried through a series of rinses to remove any residual solvent or toxic residue that may compromise the compatibility of the final product. These rinse baths were composed of solutions that caused no marked physical or chemical modification to the initial membrane. The first post bath consists of water processed through a Milli-Q purification system and was left to soak for a minimum of 15 min. The material was then removed and placed into a 70%v/v punctilious ethyl alcohol and water solution, which had been 0.2 um filtered, for a minimum of 60 mins and then removed. The final stage was soaking of the film in two sequential sterile normal saline baths with volumes of 2 ml/cm$^2$ fiber for a minimum of 60 min each.

Results

The final wet-as-cast membrane thickness was between 30 um to 75 um with a hydraulic permeability of 0.475 c$^3$/min/cm2 at 5.0 psig. Rejection coefficient data indicated that the membrane excluded substances larger than approximately 100,000 daltons.

Encapsulation and Implantation

Sterile, cast 10% flatsheet membrane soaking in saline was prepared as described above, and encapsulated islets were prepared as follows: A 6 by 8 inch sheet of wet membrane was folded over on itself with the skin sides facing so as to create a strip of double membrane about 1' wide. The fold was carefully pressed to form a crease. Using a #10 scalpel blade, the 1' wide strip of double membrane was cut off from the rest of the sheet. The double strip was picked up by one end and cut into 1' squares using scissors. The squares were caught in saline as they were cut off. The tip and bottom of each square were connected by the fold comprising one side.

Immediately prior to loading, a square was lifted out and placed on the lid of a 3' diameter polystyrene petri dish previously wet with 1–2 ml of 1% CaCl$_2$ solution. The membrane was unfolded and each side was floated on the CaCl$_2$ solution with care taken to assure that the solution did not flow into the tip of the membrane.

Previous to this, islets were allowed to settle into a pellet, and resuspended in 1% ungelled sodium alginate solution (solution was prepared by making a 2% alginate solution in H$_2$O and mixing this 50/50 with medium in which islets were cultured). Islet/alginate slurry was gently mixed by stirring and aspirating. Slurry was prepared at the rate of 500 islets in 25 ul alginate per sq cm useable surface area on a single membrane side. This equates to approximately 125 ul and 2500 rat islets for a 1' sq membrane sheet.

Islet/alginate slurry was aspirated into a 200 ul pipet tip and then evenly spread across the inside of one membrane leaving about 1/8 inch gap along all edges of the square sheet. Spreading was done rapidly as alginate slowly crosslinked due to Ca$^{++}$ diffusion through the membrane from the underlying CaCl$_2$ solution.

Once the alginate was sufficiently crosslinked to prevent alginate smearing (approx 1–2 min) the other side of the flat sheet device was folded over to form a tip to the flatsheet sandwich. Care was taken to eliminate air bubbles.

The two sides of the membrane were sealed using an impulse heat sealer with a ⅛' heating element set on medium heat (temp reached between 80–160° C.). Each edge, including the folded one, was individually sealed by activating the heat sealer while pressing down on the ⅛' strip of non-alginate coated membrane along each edge.

After sealing, the device was soaked in 1% CaCl$_2$ solution for 4 min so as to further crosslink the alginate. The device was held in Hank's solution until implantation (within 2 hours).

Flat sheet was implanted in the peritoneal cavity of a chemically diabetic recipient Wistar-Furth rat by making a midline incision through the skin and into the peritoneal cavity of the anesthetized rat. The flat sheet implant was placed in the cavity by grasping the sealed edge with smooth forceps and gently laying the device, free floating on top of the gut pile proximal to the peritoneal wall. The peritoneal cavity and skin were closed by suturing.

Animals were studied for 21 days, at which time the devices were explanted. Blood glucose levels dropped from 375 mg/dl to 150 mg/dl within 4 days of implant and remained there until explant, at which time glucose values rose to 275 mg/dl (n=2).

Histological examination revealed viable islets immobilized in the alginate layer with less than a monolayer of cells attached to the outside of the membrane.

EXAMPLE 19

Implantation of Encapsulated Bovine Adrenal Chromaffin Cells in the Lumbar Subarachnoid Space in Sheep Adrenal Gland Harvesting Bovine adrenal chromaffin cells were obtained from healthy livestock sources in herds tested for adventitious agents and known to be free of bovine Spongiform Enchephalitis. Two to three week old calves weighing 52–72 kg (62±7) were premedicated with atropine (100 mg/kg) and xylazine chlorhydrate (0.15 mg/kg). Anesthesia was induced with pentobarbital sodium (8 mg/kg), and maintained with 0.5–1% halothane delivered through an endotracheal tube. The aorta and vena cava were isolated through a cruciate organ harvesting ventral incision. The distal aorta and vena cava, the coeliac axis, and the superior and inferior mesenteric arteries were ligated. The proximal vena cava was clamped above the liver, and the proximal aorta above the coeliac axis. Four to six liters of cold saline solution and 2 liters of a hospital prepared organ preservation solution (formulated as the University of Wisconsin solution minus hydroxyethylstarch and adenosine) were perfused by a cannula introduced in the aorta. The organ preservation solution comprises potassium lactobionate 100 mM, $KH_2PO_4$ 25 mM, $MgSo4$ 5 mM, raffinose 30mM, glutathion 3 mM and allopurinol 1 mM. The adrenal glands were then harvested with their native vessels and placed in a sterile container filled with enough organ preservation solution to cover the gland. The container was placed on ice and send to the tissue culture laboratory for isolation of the chromaffin cells. Aseptic surgical techniques were utilized for all procedures. All harvested glands were of suitable quality for subsequent chromaffin cell isolation. The total amount of cells obtained by the isolation technique ranged from 2.0 to $3.0\times10^7$ cells per gland with viability greater than 95%, as assessed with FDA and PI stain. Cells were typically organized in clusters of 50 to 200 $\mu$m in diameter.

Chromaffin Cells Isolation and Culture

A cannula was inserted into the isolated gland through the suprarenal vein. The glands were then perfused with 10 ml of cold organ preservation solution via the cannula until clear perfusate was seen dripping from the gland. Five to seven ml of a 0.2% collagenase solution (Sigma, Type H) was then injected into each gland. The vein was clamped and the glands were placed in sterile beakers containing 100 ml of organ preservation solution and shaken in a 37° C. waterbath at 1 Hz for 30 minutes. This first digestion allowed mechanical separation of the cortex from the medulla by gentle pulling. The medullary tissue was then placed in a tissue culture dish with 1 ml of organ preservation solution and chopped into approximately 1–2 $mm^2$ sections. The chopped tissue pieces were then poured into a dissociation-filtration chamber with a 250 $\mu$m pore size filtration grid, filled with 10 ml of 0.2% collagenase solution and agitated at 1 Hz for 10 minutes at 37° C. Constant temperature in the chamber was maintained by an external water jacket. Every 10 minutes the chamber was rinsed with cold organ preservation solution. The isolated cells and cell clumps which passed through the filtration grid were collected in a sterile 50 ml conical tube. A total of three digestions were generally needed to fully digest the medullary tissue.

The tubes were then spun at 800 g for 5 minutes and washed two additional times with the organ preservation solution. An aliquot of the final wash supernatant was placed in thioglycolate medium for sterility testing.

The cells from each tube was plated in separate 100 mm tissue culture dishes, in 10 ml of PC-1 media, a defined medium containing protein from human recombinant sources (Hycor Biomedical Inc.).

Using a 10 mL pipet, cells were removed from each petri dish and were pooled in a 50 ml centrifuge tube. The cell solution was spun at 800 g at ambient temperature for 5 minutes. The supernatant was disposed and the pellet resuspended in 10 mL of HEPES buffered NaCl. Two 50 microliter aliquots of cell suspension were placed in separate Eppendorf tubes. One mL HEPES buffered NaCl and 1 mL FDA-PI were added to one tube, and 50 microliters Trypan blue solutions and 50 microliters Triton x-100 were added to the other tube. The Triton-Trypan cell suspension was examined on a hemocytomer and the cells were counted. The number of cells was found to be approximately $2-3\times10^6$ per mL. The FDA-PI cell solution was examined under a fluorescent microscope and the percentage of live cells was found to be greater than 95%.

The tissue culture dishes were held in a 5% $CO_2$ incubator at 37° C., until the cells were loaded into capsules.

Preparation of Alainate Solution

A 2% alginate solution was prepared dissolving 1 g of Protan Ultrapure alginate which had been cold cycle ETO sterilized in 50 mL of HEPES buffered 0.9% NaCl. The cell solution was diluted in the ratio of two parts alginate solution to one part cell solution.

Encapsulation Procedure

Hollow fibers were spun from a 12.5–13.5% poly (acrylonitrile vinylchloride) solution by a wet spinning technique. Cabasso, Hollow Fiber Membranes, vol. 12, *Kirk-Othmer Encyclopedia of Chemical Technology*, Wiley, N.Y., 3rd Ed. pp. 492–517 (1980). The resulting hollow fiber had an outside diameter (OD) of around 900 $\mu$m and a wall thickness of around 150 $\mu$m. The fibers had a hydraulic permeability of 18 $ml/min/m^2/mmHg$ and a rejection coefficient of more than 90% for bovine serum albumin. Fibers were impregnated with glycerine for storage purposes.

In order to make implantable capsules, lengths of fiber were first cut into 5 cm long segments and the distal extremity of each segment was sealed with an acrylic glue. Encapsulation hub assemblies were prepared by providing lengths of the membrane described above, sealing one end of the fiber with a single drop of LCM 24 (Light curable acrylate glue, available from ICI), and curing the glue with blue light, and repeating the step with a second drop. The opposite end was previously attached to a frangible necked hub assembly, having a silicone septum through which the cell solution may be introduced. The fiber was glued to the hub assembly by applying LCM 22 to the outer diameter of the hub assembly, and pulling the fiber up over it, and curing with blue light. The hub/fiber assemblies were placed in sterilization bags and were ETO sterilized.

Following sterilization with ethylene oxide and outgassing, the fibers were deglycerinated by ultrafiltering first 70% EtOH, and then HEPES buffered saline solution through the walls of the fiber under vacuum.

The cell/alginate suspension (approx. $20\times10^6$ cells/100 $\mu$l) was placed in a 1 ml syringe. A Hamilton 1800 Series 50 microliter syringe was set for a 15 microliter air bubble, and was inserted into a 1 ml syringe containing the cell solution and 30 microliters were drawn up. The cell solution was injected through the silicone seal of the hub/fiber assembly into the lumen of a modacrylic hollow fiber membrane with a molecular weight cutoff of approximately 50,000 daltons. Ultrafiltration could be observed along the entire length of the fiber. After one minute, the hub was snapped off the sub-hub, exposing a fresh surface, unwet by cell solution. A single drop of LCM 24 was applied and the adhesive was cured with blue light. The device was placed first in HEPES buffered NaCl solution and then in $CaCl_2$ solution for five minutes to cross-link the alginate. Each implant was about 5 cm long, 1 mm in diameter, and contained approximately 2.5 million cells.

After the devices were filled and sealed a silicone tether (Speciality Silcone Fabrication, Paso Robles, Calif.) (ID: 0.69, OD: 1.25) was then placed over the proximal end of the fiber. A radiopaque titanium plug was inserted in the lumen of the silicone tether to act as a radiographic marker. The devices were then placed in 100 mm tissue culture dishes in 1.5 ml PC-1 medium, and stored at 37° C., in a 5% $CO_2$ incubator for in vitro analysis and for storage until implantation.

Implantation

Devices were implanted one week following the cell loading procedure. Sheep weighing 42–90 kg (69±15) were given general, endotracheal anesthesia (pentobarbital sodium 10 mg/kg iv; halothane 0.5–2%) and preoperative antibiotics (cefazolin sodium 1 g iv). The animals were positioned in the prone position and the operating table tilted head up at 30°. A 510 cm parasaggital lumbar incision was made and a spinal tap performed with a Tuohy needle between L4 and L5 via an oblique paramedian approach. The appropriate position of the needle in the subarachnoid space was confirmed by withdrawal of several mls of CSF. This CSF was analyzed for cell counts, protein level, and microbiology. A guide wire was introduced through the lumen of the Tuohy needle until it extended 4–5 cm cranially from the needle opening. The Tuohy needle was removed and a 7 French dilator introduced over the guide wire to the level of the dura and removed, enlarging the wire track through the fascia, paraspinous muscle and ligamentum flavum. This allowed a 6 French dilator with a 20 cm long outer cannula sheath to be advanced into the subarachnoid space until the tip of the cannula was positioned 7 cm within the space. The guide wire and the dilator were then removed, leaving the cannula within the subarachnoid space to act as a protective guide for insertion of the encapsule.

The cell-loaded and fully assembled device was delivered into the operating room in a sterile container, bathed in PC-1 medium. The device was prepared for insertion by mounting the tether on a stainless steel pusher which served to stiffen the very flexible tether and allowed the capsule to be manipulated within the lumen of the cannula. The membrane portion of the device was then introduced into the cannula, handling the device by the silicone tether and the handle of the pusher. The device was advanced until the membrane portion lay entirely within the CSF containing subarachnoid space. The cannula was then removed while the device was maintained in position using the pusher. Finally, the pusher was removed and the silicone tether anchored at its free end by a non-absorbable suture and completely covered with a 2 layer closure of skin and subcutaneous tissue.

The animal was recovered, examined for possible neurological complications, and returned to the farm for boarding on the day of implantation. All animals were able to return to normal diet and activity on the day of surgery. All experimental, animal care and surgical protocols were approved by the Canton of Vaud Committee on animal research.

Explantation

Four to eight weeks post-implantation each sheep was anesthetized as described above. The subcutaneous portion of the silicone tether was isolated through a small skin issue incision. The device was then retrieved by gentle traction. The capsule was placed in PC-1 media for analysis of catecholamine release and then fixed in 4% paraformaldehyde solution for histology. A spinal tap was performed for all cell counts, protein level and microbiology prior to the removal of the device. The animal was allowed to recover and one week following retrieval of the device, CSF samples were again taken and the animal was sacrificed by overdosage of pentobarbitral.

Neurochemical Assays

The ability of the capsules to release catecholamines was determined before and after transplantation. Each capsule was first placed in 2 ml Hank's balanced buffered saline (HBSS) solution for 30 minutes and basal release samples were collected. Evoked release was obtained by incubating the capsule in 63 $\mu$m nicotine solution in HBSS for another 30 minutes. Perchloric acid (1N) was added to the collected samples as an antioxidant. Catecholamines levels were determined by reverse phase high performance liquid chromatography (HPLC) with electrochemical detection.

Histology

Following fixation in 4% paraformaldehyde, the retrieved capsules were rinsed with phosphate buffered saline (PBS), dehydrated in graded alcohol up to 95% and embedded in blycol methacrylate infiltration solution (Historesine Mounting Medium, Reichert-Jung). Three micron thick sections were cut on a microtome (Supercut 2065, Leica), mounted on glass slides and stained with cresyl violet. For immunohistochemistry the capsules were also fixed in 4% paraformaldehyde, embedded in 5% agarose and cut on a cryostat (Cryocut 1800, Leica). The immunostain consisted of a mouse monoclonal antibody to tyrosine hydroxylase (Boehringer Mannheim) using the peroxidase-antiperoxidase (PAP) technique and diaminobenzidine (DAB) coloration.

Results

Neurochemical Analysis

All capsules released a significant amount of catecholamines under nicotine stimulation. An increase in the catecholamine release from the capsules on day—1 (one day before implantation, seven days post-isolation) was observed with each subsequent isolation and encapsulation series. The mean evoked release of each batch ranged from 362±14 to 1464±300 pmol/2ml/30 min for norepinephrine and 161±11 to 1350±344 pmol/2ml/30 min for epinephrin. As indicated by the standard deviation, there were small but noticeable variations in catecholamine release between the various capsules of each batch. Basal release was below 230 pmol/2ml/30 min for both catecholamines measured.

Typically, the cohorts maintained in vitro were analyzed at day-1, +7, +14, +21 and +28 days following transplantation for evoked release of catecholamines. All capsules continued to respond to nicotine stimulation for at least one month post-encapsulation. Some showed an increase in their release over time (batch 1,2), some remained stable (batch 3), and some demonstrated a progressive decrease of their release over time (batch 4, 5).

Histology

Microscopic examination showed good viability of the encapsulated cells. The cells were organized in small aggregates entrapped in the alginate matrix. These cell clusters were all positive for tyrosine-hydroxylase immunochemistry. There was some disparity in capsule loading within and between batches.

Surgery and Behavior

No infections were observed in the implanted sheep and all CSF samples collected were sterile. No increase in leucocyte counts were observed in the CSF between the implantation and explantation times. The same was true for protein levels with exception of sheep 5 which showed a doubling of CSF protein concentration at the explantation time. A traumatic spinal tap at the explantation may explain this increase. Of the six implanted sheep, two showed a transitory weakness of the hind limbs following the transplantation procedure. An additional sheep showed a complete paralysis at the time of recovery and did not show any improvement in the following hours. This animal was sacrificed on the first day post-transplantation and was therefore not included in the present series. At autopsy the device appeared to have perforated the spinal cord of the animal.

No further surgical complications were encountered. All devices were retrieved through a small skin incision by gentle traction on the tether at 4 or 8 weeks post-implantation. The silicone tethers remained firmly fixed to the capsules; the membranes remained integral and attached to the tether.

Morphologic Analysis

All the retrieved capsules were intact on gross examination. The membrane was devoid of host cells by microscopic examination. Clusters of viable cells dispersed in the alginate matrix were observed throughout the capsule. The cell aggregates were strongly positive for tyrosine hydroxylase. Capsule loading varied between batches, with a general upward trend.

Release

After retrieval, explanted devices were tested for catecholamine release in order to assess chromaffin cell viability and responsiveness to nicotine stimulation. Basal and stimulated release levels were measured and compared to levels in in-vitro cohorts. With the exception of sheep 3, the evoked release of retrieved capsules was in the same range as their respective in vitro cohort evoked release. In sheep 4, the release of the retrieved capsule was higher than that of its in vitro cohort. For Sheep 6, both explanted capsules and in-vitro controls had low levels of catecholamine release.

EXAMPLE 20

Implantation of Encapsulated Cellular Grafts in the Lumbar Subarachnoid Space in Humans Fiber Characteristics The semipermeable membrane fibers used in this trial were double skinned PAN/PVC fibers having the following dimensions: an inner diameter of 773 microns, an outer diameter of 920 microns, and a wall thickness of 73.1 microns.

Preparation and Encapsulation of Calf Adrenal Cells

Bovine adrenal chromaffin cells were prepared and encapsulated as outlined in example 19.

Surgical Procedure

After establishing IV access and administering prophylactic antibiotics (cefazolin sodium, 1 gram IV), the patient was positioned on the operating table, generally in either the lateral decubitus or genu-pectoral position, with the lumbar spine flexed anteriorly. The operative field was sterily prepared and draped exposing the midline dorsal lumbar region from the levels of S-1 to L-1, and allowing for intraoperative imaging of the lumbar spine with C-arm fluoroscopy. Local infiltration with 1.0% lidocaine was used to establish anesthesia of the skin as well as the periosteum and other deep connective tissue structures down to and including the ligamentum flavum.

A 3–5 cm skin incision was made in the parasagital plane 1–2 cm to the right or left of the midline and was continued down to the lumbodorsal fascia using electrocautery for hemostasis. Using traditional bony landmarks including the iliac crests and the lumbar spinous processes, as well as fluoroscopic guidance, and 18 gauge Touhy needle was introduced into the subarachnoid space between L-3 and L-4 via an oblique paramedian approach. The needle was directed so that it entered the space at a shallow, superiorly directed angle that was no greater than 30°–35° with respect to the spinal cord in either the sagittal or transverse plane. Appropriate position of the tip of the needle was confirmed by withdrawal of several ml of cerebrospinal fluid (CSF) for preimplantation catecholamine, enkephalin, glucose, and protein levels and cell counts.

The Touhy needle hub was reexamined to confirm that the opening at the tip is oriented superiorly (opening direction is marked by the indexing notch for the obturator on the needle hub), and the guide wire was passed down the lumen of the needle until it extended 4–5 cm into the subarachnoid space (determined by premeasuring). Care was taken during passage of the wire that there was not resistance to advancement of the wire out of the needle and that the patient did not complain of significant neurogenic symptoms, either of which observations might indicate misdirection of the guide wire and possible impending nerve root or spinal cord injury.

After the guide wire appeared to be appropriately placed in the subarachnoid space, the Touhy needle was separately withdrawn and removed from the wire. The position of the wire in the midline of the spinal canal, anterior to the expected location of the caud equina, and without kinks or unexplainable bends was then confirmed with fluoroscopy. After removal of the Touhy needle the guide wire should be able to be moved freely into and out of the space with only very slight resistance due to the rough surface of the wire running through the dense and fibrous ligamentum flavum.

The 7 French dilator was then placed over the guide wire and the wire was used to direct the dilator as it was gently but firmly pushed through the fascia, paraspinous muscle, and ligamentum flavum, following the track of the wire toward the subarachnoid space. Advancement of the 7 French dilator was stopped and the dilator removed from the wire as soon as a loss of resistance was detected after passing the ligamentum flavum. This was done in order to avoid advancing and manipulating this relatively rigid dilator within the subarachnoid space to any significant degree.

After the wire track was "overdilated" by the 7 French dilator, the 6 French dilator and cannula sheath were assembled and placed over the guide wire. The 6 French dilator and cannula were advanced carefully into the subarachnoid space until the opening tip of the cannula was positioned 7 cm within the space. As with the 7 French dilator, the assembled 6 French dilator and cannula were directed by the wire within the lumen of the dilator. Position within the subarachnoid space was determined by premeasuring the device and was grossly confirmed by fluoroscopy. Great care was taken with manipulation of the dilators and cannula within the subarachnoid space to avoid misdirection and possible neurologic injury.

When appropriate positioning of the cannula was assured, the guide wire and the 6 French dilator were gently removed from the lumen of the cannula in sequence. Depending on the patient's position on the operating table, CSF flow through the cannula at this point should be noticeable and may be very brisk, requiring capping the cannula or very prompt placement of the capsule implant in order to prevent excessive CSF.

The encapsulated adrenal chromaffin cell graft (CytoTherapeutics CereCRIB™) was provided in a sterile, double envelope container, bathed in transport medium, and fully assembled including a tubular silicone tether. Prior to implantation through the cannula and into the subarachnoid space, the capsule was transferred to the insertion kit tray where it was positioned in a location that allowed the capsule to be maintained in transport medium while it was grossly examined for damage or major defects, and while the silicone tether was trimmed, adjusting its length to the pusher and removing the hemaclip™ that plugs its external end.

The tether portion of the CereCRIB™ capsule was mounted onto the stainless steel pusher by inserting the small diameter wire portion of the pusher as the membrane portion of the device was carefully introduced into the cannula. The capsule was advanced until the tip of the membrane reached a point that was 2–10 mm within the cranial tip of the cannula in the subarachnoid space. This placement was achieved by premeasuring the cannula and the capsule-tether-pusher assembly, and it assured that the membrane portion of the capsule was protected by the cannula for the entire time that it was being advanced into position.

After the capsule was positioned within the cannula, the pusher was used to hold the capsule in position (without advancing or withdrawing) in the subarachnoid space while the cannula was completely withdrawn from over the capsule and pusher. The pusher was then removed from the capsule by sliding its wire portion out of the silicone tether. Using this method the final placement of the capsule was such that the 5 cm long membrane portion of the device lay entirely within the CSF containing subarachnoid space ventral to the cauda equina. It was anchored at its caudal end by a roughly 1–2 cm length of silicone tether that ran within the subarachnoid space before the tether exited through the dura and ligamentum flavum. The tether continued externally from this level through the paraspinous muscle and emerged from the lumbodorsal fascia leaving generally 10–12 cm of free tether material that was available for securing the device.

CSF leakage was minimized by injecting fibrin glue (Tissel®) into the track occupied by the tether in the paraspinous muscle, and by firmly closing the superficial fascial opening of the track with a purse-string suture. The free end of the tether was then anchored with non-absorbable suture and completely covered with a 2 layer closure of the skin and subcutaneous tissue.

The patient was then transferred to the neurosurgical recovery area and kept at strict bed rest, recumbent, for 24 hours postoperatively. Antibiotic prophylaxis is also continued for 24 hours following the implantation procedure.

Human Pain Patients

Three human terminally ill patients suffering from intractable pain were implanted according to the method outlined above.

Devices were released for implantation only after individual testing for sterility and for release of catecholamines. The protocol called for a thirty day study that could be extended to a maximum of 90 days upon the request of the patients. Three patients were eligible with terminal cancer, pain incompletely relieved by narcotic therapy, and no evidence of active infection or tumor in the meningeal space. After informed consent was granted by the patients and approval was received from the Ethical Committee of the Faculty of Medicine of the University of Lausanne, Switzerland, the devices were implanted under local anesthesia.

Postoperative recovery was uneventful though all patients experienced some loss of CSF fluid and one patient experienced headaches of several days duration. Two of the three patients recorded improvement on the McGill questionnaire and a visual analog scale of pain; the third did not. Significant increases were observed in the cerebrospinal fluid catecholamine levels of the two patients with improved pain scores. All three patients reduced their intake of narcotics and analgesics (Table 3).

The tethered implants were recovered via simple surgical excision after 43 days and 55 days in two patients and at autopsy in patient #3 who died from her primary disease at day 42. Explanted devices were inspected visually and then examined histologically and for biochemical activity. There was no visible difference between the devices as implanted and as retrieved. Upon microcoscopic examination, external surfaces of all three implants were free of adherent cells, fibrotic overlayers, and other signs of acute phase response or foreign body reaction.

Intracapsular populations of healthy chromaffin cells were observed by histology in all three explants, with cell viability estimated at 80 percent. Cells recovered from the capsules were also positive by immunohistochemistry for tyrosine hydroxylase and metenkaphalins. Basal release of norepinephrine and epinephrine in explanted capsules was in the range of 0.2 and 3 nanomoles per 24 hours. Autopsy reports on the spinal cords became available in all three patients and showed no effect from the implant.

TABLE 3

MORPHINE INTAKE (mg/day)

|  | pre-implant | post implant[1] |
|---|---|---|
| oral |  |  |
| Patient 1 | 60 | 0 |
| Patient 2 | 0 | 0 |
| Patient 3 | 60 | 0 |
| epidural |  |  |
| Patient 1 | 75 | 18 |
| Patient 2 | 60 | 32 |
| Patient 3 | 0 | 0 |

[1]Mean value from day 10 post implant to explant (or death)

EXAMPLE 21

Implantation of Encapsulated Cellular Grafts Intracranially, in the Lateral Ventricle in Humans Two human patients suffering from intractable pain were implanted in the ventricle of the brain with encapsulated adrenal chromaffin cells. The brain ventricles, including the lateral ventricles, lie rostral to the lumbar region. The CSF drains or flows from the brain to the spinal cord. The chromaffin cells and CereCRIB™ capsules were prepared as described in Example 20.

The surgical procedure for implantation into the lateral ventricle of the brain is described below.

Immediately before the implantation procedure, the patient was fitted with a stereotactic head ring assembly and localizer ring (or image localization/marker device) suitable for guided cannula placement within the lateral ventricles using local anesthesia (local infiltration with generally 1% lidocaine). The Radionics® BRW frame was used here, however the Radionics® CRW, Leksell®, or functionally similar devices are also appropriate.

A computed tomography (CT) scan was then performed and used to define a target site(s) and stereotactic coordinates for the implant(s). Implantation cannula trajectory and implant site were chosen with the following considerations: (1) avoiding the frontal sinuses; (2) avoiding the choroid plexus; (3) allowing straight, undistorted positioning of the intended implant within the lateral ventricle. There are three capsule lengths, 2.5, 3.75, or 5.0 cm, currently in use. The two patients in this study were implanted with 2.5 cm CereCRIB™ capsules.

A target site must be selected that will allow a length of the internal end of the cannula that is at least the length of the membrane portion of the desired capsule to lie within an acceptable, CSF filled space within the ventricle. The zero reference point for determining cannula insertion depth is the surface of the skin, as seen on the CT scan, and the target site is defined as the intended target of the internal tip (opening) of the insertion cannula.

Two implant devices may be placed in one patient at a single procedure by placing one implant in each lateral ventricle. Future implantation sites may target the third ventricle and/or the aqueduct. The current stereotactic guidance technique uses CT imaging for reference, however magnetic resonance imaging (MRI), stereotactic at last coordinates, ultrasound or other guidance methods may also be appropriate. Following completion of the data gathering for stereotactic placement of the implant(s), the patient is transferred to the operating room for the implantation procedure.

After establishing IV access and administering prophylactic antibiotics (currently, cefazolin sodium, 1 gram IV), the patient was positioned on the operating table in the semi-supine/seated position with the stereotactic head ring assembly secured to the table. The operative field was sterily prepared and draped exposing the intended implantation site(s) (generally located in the paramedian, frontal region) and allowing for sterile placement and removal of the stereotactic arc system/manipulator to the frame base.

Local infiltration with 1.0% lidocaine was used for anesthesia of the skin and deeper scalp structures down to the periosteum, and a 4–8 cm skin incision was made down to the skull at the calculated entry site(s) for the stereotactically guided insertion canula (generally in the frontal region, in the parasagital plane 3 cm to the right or left of the midline) using electrocautery for hemostasis. A twist drill guided by the stereotactic arc system was then used to create a burr hole (generally 4 mm diameter) down to the level of the dura. The dura was sharply penetrated, and the insertion cannula/obturator assembly was mounted into the stereotaxic microdrive and directed into the burr hole. Blood from the wound was excluded from the burr hole by applying the microdrive guide tube directly against the rim of the burr hole.

The insertion cannula/obturator assembly were advanced manually to the preset depth stop on the microdrive, leaving the tip of the cannula at the target site. The obturator was then carefully withdrawn from the insertion cannula, taking care not to deflect the cannula with the tip of the obturator. Appropriate position of the tip of the cannula within the ventricle may be confirmed by a meniscus of cerebrospinal fluid (CSF) rising up within the clear insertion cannula after removal of the obturator. Samples of CSF may be taken for preimplantation catecholamine, enkephalin, glucose, and protein levels and cell counts.

The encapsulated adrenal chromaffin cell graft (CytoTherapeutics CereCRIB™) was prepared and mounted onto the pusher as described in Example 20.

The CereCRIB™ capsule was handled completely by the silicone tether and the handle of the pusher as the membrane portion of the device was carefully introduced into the cannula. The capsule was advanced until the tip of the membrane reached a point that was within 1–2 mm of the internal tip of the cannula positioned in the lateral ventricle (but not extending beyond the tip of the cannula). This placement was achieved by premeasuring the cannula and the capsule- tether-pusher assembly, and it assured that the membrane portion of the capsule was protected by the cannula for the entire time that it was being advanced into position. After the capsule was positioned manually within the cannula, the pusher was locked into position in the microdrive and used to hold the capsule in position in the ventricle (without advancing or withdrawing) while the cannula was completely withdrawn from over the capsule and pusher. The pusher was then removed from the capsule by sliding its wire portion out of the silicone tether.

Using this method the final placement of the capsule was such that the entire membrane portion of the device lay entirely within an appropriate, CSF containing region of the ventricle. The membrane capsule was anchored at its external end by a length of silicone tether that ran (generally) through a portion of the frontal lobe before it exited through the dura and the skull, leaving generally 5–10 cm of free tether material that was available for securing the device. The free end of the tether was then anchored to the outer table of the skull adjacent to the burr hole using a standard, maxillo-facial miniplate and screws and completely covered with a 2 or 3 layer closure.

The patients were then transferred to the neurosurgical recovery area and followed for 12 hours postoperatively for potential hemorrhagic complications with no special restrictions. Antibiotic prophylaxis was also continued for 24 hours following the implantation procedure.

EXAMPLE 22

Implantation of β-NGF Secreting BHK Cells for Prevention of Neural Damage Due to Excitotoxicity (Huntington's Disease Model)

Subjects

Adult male Sprague-Dawley rats (Taconic Breeders, Germantown, N.Y.) approximately 3 months old and weighing 300–350 grams were used. The animals were housed in groups of 3 in a temperature and humidity-controlled colony room which was maintained on a 12 hr light/dark cycle with lights on at 0700 hrs. Food and water were available ad libitum throughout the experiment.

BHK-NGF Cell Line Production

Two human genomic clones (phbeta N8D8, phbeta N8B9) coding for the 5' and 3' ends of the β-NGF gene were obtained from the ATCC. A 440 bp 5' ScaI-EcoR1 fragment from phbeta N8D8 was ligated to a 3' 2.0 kb EcoR1 fragment isolated from phbeta N8B9. The spliced NGF genomic sequence contained approximately 37 bp of the 3' end of the first intron, the double ATG sequence believed to be the protein translation start for pre- pro-NGF and the complete coding sequence and entire 3' untranslated region of the human gene (Hoyle et al., *Neuron*, 10, pp. 1019–34 (1993)). The combined 2.51 kb β-NGF fragment was subcloned into the DHFR-based pNUT expression vector immediately downstream from the mouse metallothionein-1 promotor (−650 to +7) and the first intron of the rate insulin II gene (Baetge et al., *Proc. Natl. Acad. Sci.*, 83, pp. 5454–58 (1986). The pNUT-βNGF construct was introduced into BHK cells using a standard calcium phosphate-mediated transfection method. Mock-transfected cells served as controls in these experiments. BHK cells were grown in DMEM, 10% fetal bovine serum, antibiotic/antimycotic, and L-glutamine (GIBCO) in 5% CO2 and at 37° C. Transfected BHK cells were selected in medium containing 200 μM methotrexate (Sigma) for 3–4 weeks and resistant cells were maintained as a polyclonal population either with or without 200 μM methotrexate.

Encapsulation Procedure

Asymmetric hollow fibers were cast from solutions of 12.5–13.5% poly (acrylonitrile vinyl chloride, PAN-PVC) copolymer in dimethyl sulfoxide (w/w). The fabrication process utilized a dry-wet (jet) spinning technique according to Cabasso, Hollow Fiber Membranes, vol. 12, *Kirk-Othmer Encyclopedia of Chemical Technology*, Wiley, N.Y., 3rd Ed., pp. 492–517 (1980). Single cell suspensions of BHK cells were prepared using calcium- and magnesium-free Hanks' balanced salts (HBSS) and trypsin/EDTA. Encapsulation devices were manufactured by mounting a 1–1.1 cm length of dry hollow fiber onto hub with a septal fixture at the proximal end which has loading access for cells to be injected into the lumen of the device. Cells were loaded into the prefabricated capsules as follows: BHK control cells and BHK/hNGF cells were loaded at a density of approximately $10^7$ cells/ml. The BHK cell suspensions, at a density of $2 \times 10^7$ cells/ml, were mixed 1:1 with physiologic Vitrogen® (Celtrix, Palo Alto, Calif.), and infused into the capsules through the septal access port. After infusing 2.2.5 μl of the cellular suspension, the septum was cracked off and the access port was sealed using a light-cured acrylate (Luxtrak™ LCM 24, ICI Resins US, Wilmington, Mass.). The capsules were subsequently "tethered" by placing a 1.5 cm 0.020" silastic tube over the acrylic hub. The cell-loaded devices were transferred into sterile 5 ml polypropylene snap cap tubes containing 4.5 ml of PC-1 medium. The 5 ml snap cap tube was then placed inside a sterile 50 ml conical centrifuge tube and sealed for transport.

BHK cell-loaded capsules were maintained in serum-free defined PC-1 medium (Hycor Biomedical Inc., Portland, Me.) for 2–5 days prior to implantation. After 3 or 4 days in vitro, cell-loaded capsules were rinsed in HBSS, placed in 1 ml of fresh PC-1 medium overnight, and the medium analyzed for hNGF by ELISA. NGF ELISA The quantification of hNGF released from encapsulated BHK/hNGF cells was performed as follows. All of the reagents were obtained from Boehringer-Mannheim Biochemicals unless otherwise noted. Nunc-Immuno Maxisorp ELISA plates were coated with 150 μl per well of anti-mouse-β (2.5S) NGF at 1 ng/ml in coating buffer (1×PBS without $CaCl_2$ and without $MgClsub_2$/0.1% sodium azide; pH 9.6). The coated plates were incubated at 37° C. for at least 2 hours or alternatively at 4° C. overnight.

The coating solution was withdrawn from the wells and the wells were washed 3× with 300 μl wash buffer (50 mm Tris-HCl/200 mm $NaCl_2$/1% Triton X-100/0.1% sodium azide; pH 7.0). The wells were then blocked with 300 μl of coating solution containing 10 mg/ml of BSA at room temperature for 30 min. The wells were then washed 3× with 300 μl wash buffer. Conditioned medium samples were diluted 1:1 in 2× sample buffer (the sample buffer is the same as wash buffer, only with 2% BSA), with 10 μl of the prepared samples loaded into the wells. The plates were covered and incubated for at least 2 hours at 37° C. or overnight at 4° C.

The solutions were removed from the wells by suction and washed 3× with 300 μl of wash buffer. To each well, 100 μl of 4U/ml of anti-mouse-β (2.5S) NGF-β-gal conjugate was added. The plates were incubated at 37° C. for at least 1 hour. The solutions were removed from the wells by suction and washed 3× with 300 of wash buffer. Finally, 200 μl of chlorophenol red-β-D-galactopyranoside substrate solution (40 mg CPRG in 100 mm Hepes/150 mm NaCl/2 mm $MgCl_2$/0.1% sodium azide/1% BSA; pH 7.0) was added to the wells, incubated at 37° C. for 30 min to one hr or after the color development was sufficient for photometric determination at 570 nm, with the samples analyzed on a plate reader and measured against recombinant NGF protein standards.

Surgery

Immediately prior to surgery, rats were anesthetized with sodium pentobarbital (45 mg/kg, i.p.), and positioned in a Kopf stereotaxic instrument. A sagittal incision was made in the scalp and two holes drilled for the placement of the cell-loaded capsules into the lateral ventricle. Rats were unilaterally implanted by placing the capsule within an 18 gauge Teflon catheter mounted to the stereotaxic frame as previously described. The stereotaxic coordinates for implantation were: anterior 0.5 mm anterior to gregma, 1.5 mm lateral to the sagittal suture and 8.0 mm below the cortical surface.

Three days following implantation of cell-loaded capsules, animals were anesthetized, placed in the stereotaxic instrument and injected with 225 nmol of quinolinic acid ("QA") or phosphate-buffered saline (PBS) into the striatum at the following coordinates: anterior + +1.2 mm, lateral=±2.6 mm and ventral=−5.5 mm from the surface of the brain. QA (Sigma Chemical Co.) was dissolved in 2N sodium hydroxide and diluted with phosphate buffer at pH 7.2 to a final pH of 7.4 and concentration of 225 nmol/ul. QA was infused into the striatum, using a 28-gauge Hamilton syringe, over five min in a volume of 1 μl. The injection cannula was left in place for an additional two min to allow for diffusion of the perfusate. This procedure resulted in the formation of three experimental groups: 1) quinolinic acid only (QA; N=8), quinolinic acid+NGF-secreting BHK cells (QA/BHK/hNGF; N=6), and quinolinc acid+control BHK cells (QA/BHK/CONTROL; N=7).

Immediately following surgery, animals were injected i.p. with 10 ml of lactated Ringer's solution. Animals were housed postoperatively with food mash and water available ad libitum.

At the conclusion of behavioral testing, animals were anesthetized and placed into the stereotaxic instrument. A craniotomy was performed. over the implantation site and the dural scar surrounding the implant site excised. The cortical surface was cut to expose the underlying capsule witch was retrieved with a pair of Dumont (#5) forceps.

Histology

A subset of animals (3–4 per group) were anesthetized 29–30 days following surgery and prepared for histological analysis. Animals were transcardially perfused, using a peristaltic pump, with 20 ml saline followed by 500 ml of paraformaldehyde. All solutions were ice cold (4° C.) and prepared in 50 mM PBS (pH 7.4). Brains were removed following fixation, placed in 25% buffered sucrose (pH 7.4) and refrigerated for approximately 48 hr.

Tissue was cut at 40 μm intervals on a cryostat and mounted onto polylysine coated slides. Alternating sections were taken throughout the striatum and processed for immunocytochemical localization of choline acetyltransferase (ChAT) and glial fibrillary acidic protein (GFAP) according to the following protocol: 1) overnight incubation in PBS containing 0.8% Triton X-100+10% normal serum, 2) 48 hr incubation with primary antibody (goat antiserum to CHAT;

Chemicon) at a dilution of 1:1000 or (rabbit antiserum to GFAP at a dilution of 1:5,000), 3) 6×5 min rinses in PBS+0.2% Triton X-100 followed by a 1.5 hour incubation in biotinylated secondary antibody (lgG), 4) 6×5 min rinses in PBS+0.2% Triton X-100, 5) incubation with Avidin-Biotin Complex (ABC, Vector Elite) for 1.5 hours, 6) 3×5 min rinses in PBS, 7) 5 min rinse in distilled water, 8) incubation DAB (0.05%) +2% nickel ammonium sulfate (ChAT only) dissolved in 0.1% Tris buffer for 5 min followed by hydrogen peroxide (0.01%) for 5 minutes, (9) the reaction was terminated by 3×1 min rinses in PBS.

A separate series of sections throughout the striatum were stained for NADPH-diaphorase according to the procedure of Vincent et al. Adjacent sections were stained with hematoxylin and eosin (H+E). Sections were mounted, dehydrated and coverslipped.

For analysis of retrieved capsules, capsules were fixed in a 4% paraformaldehyde, 0.5% glutaraldehyde solution, rinsed in PBS and dehydrated up to 95% ethanol. A 1:1 solution of glycol methacrylate (Historesin, Reichert-Jung, Cambridge Instruments) was then added to the capsules for one hr. Pure infiltration solution replaced the 1:1 mixture and remained for a minimum of 2 hrs. The capsules were then rinsed with the embedding solution, transferred to flat molds, and embedded in glycol methacrylate. Sections 5 $\mu$m thick were sectioned (Reichert-Jung, Supercut microtome 2065), mounted on glass slides and stained for H+E.

Behavioral Testing

Beginning 13–14 days following QA injections, animals were tested for apomorphine-induced (1.0 mg/kg in normal saline containing 0.2% ascorbate) rotation behavior in one of six rotation devices (Rotoscan, Omnitech Instruments) which were connected to an IBM computer for automated data collection. Animals were placed into the test chamber for a 5 min habituation period and were then injected with apomorphine. Sensitization of apomorphine-induced rotation behavior occurs following excitotoxin lesions of the striatum. Therefore, animals were tested 4 times with each session separated by a 3–4 day interval. Rotations were defined as complete 360 degree ipsilateral turns and were reported as the net difference between the two directions.

Statistical Analysis

The behavioral results were assessed using a two-way repeated measures analysis of variance (ANOVA). Appropriate pair-wise comparisons were performed using Fisher's Least Significant Difference test. Acceptable statistical significance was established at $p < 0.05$.

Results

Behavioral testing

No overt signs of behavioral or neurological toxicity were observed in any animals following implantation of either BHK/hNGF or BHK control capsules. During the post-operative recovery period following QA injections, the QA/BHK/CONTROL and QA alone groups exhibited whole body barrel rotations which persisted for 2–4 hours. These same animals had a transient period of weight loss, piloerection and diarrhea which subsided 3–4 days following QA. Animals which received QA together the BHK/hNGF capsules did not show whole body rotations but did exhibit a slight motor asymmetry following QA. This asymmetry was transient and recovery was seen within several hrs. No additional signs of systemic toxicity were noted.

Following QA injections, animals displayed apomorphine-induced rotations ipsilateral to the lesion with the extent of rotation behavior increasing with repeated testing. hNGF treatment significantly decreased the extent of rotation behavior produced by QA. A two-way repeated ANOVA revealed significant effects of treatment $F(2, 17)= 16.063$, $p<0.0001$, as well as repeated testing $F(2, 3)=28.861$, $p<0.0001$, and a treatment by testing interation F $(6, 51)=2.937$, $p<0.05$. Post-hoc analysis revealed that the QA/hNGF group rotated significantly less than either the QA alone or QA/BHK control at all test times. No significant differences were observed between the QA alone and QA/BHK control groups at any time during testing.

NGF ELISA

Prior to implantation and following retrieval (immediately prior to perfusion), the encapsulated BHK cells were incubated and the conditioned medium was assayed for hNGF by ELISA. Prior to implantation, the encapsulated BHK/hNGF cells were releasing 34.13 (±6.9) ng NGF/capsule/24 hr while BHK/CONTROL cells showed hNGF levels no different than measured in control medium (0.06 ng NGF/capsule/24 hr). The BHK cell-loaded capsules were easily retrieved with little or no host tissue adhering to the capsule wall. Post explant values of hNGF from capsules averaged 16.03 (±6.0) ng hNGF/capsule/24 hr and was not detected in conditioned medium from BHK/CONTROL capsules.

Histology

The cell-loaded devices were easily retrieved and induced minimal damage to the host tissue. Placement of the capsules was within the lateral ventricle in all cases. Analysis of sections throughout the implant site revealed that the devices abutted the cortex and extended through the corpus callosum to the ventral aspect of the lateral ventricle. The capsules typically extended into the host striatum and in some cases medially into the lateral septum.

Administration of QA produced a substantial atrophy of the striatum together with a marked ventricular dilation. In some cases moderate cell loss was observed in the nucleus accumbens and cortical regions adjacent to the injection site. The lesion core was virtually devoid of neurons with a nearly complete loss of ChAT and NADPH-d positive neurons. In general, the remaining neurons present within the lesion core were shrunken and dystrophic in appearance. GFAP staining revealed the presence of reactive astrocytes throughout the lesion site and extending into the adjacent host tissue.

Implantation of BHK control cell-loaded devices into the lateral ventricles did not effect striatal morphology Furthermore, no alterations in the size of the lesion core or extent of cell loss was observed in these animals. Infiltration of reactive astrocytes dominated the ventricular wall and the striatum immediately adjacent to the implantation site. In contrast, implantation of encapsulated BHK cells which released hNGF exerted a marked protective effect on striatal morphology following QA. In these animals, the lesion core was significantly reduced and frequently consisted of cell necrosis surrounding the injection tract with minimal extension into the surrounding tissue. Within the lesion core there was no apparent sparing of neurons. On the other hand, NADPH-d, and Nissl staining revealed a striking preservation of neurons removed from the central lesion core. In general, the sparing of ChAT-positive neurons appeared greater than that of NADPH-d-positive neurons.

Capsule morphology and cell survival of the encapsulated BHK cells were determined. Few adhering host cells were found on the capsule surface. An abundance of viable BHK cells were evenly distributed throughout the capsule. Areas of focal cell debris were occasionally observed within the cores of large viable cell aggregates. Numerous mitotic figures were observed throughout the capsules and no differences in cell survival were noted between BHK/hNGF and BHK/CONTROL cells.

These data indicate implantation of polymer encapsulated BHK cells, genetically-modified to secrete hNGF, prior to intrastriatal injections of QA, results in attenuation of the associated neurotoxicity. QA alone produced a marked striatal atrophy together with loss of ChAT and NADPH-d-positive neurons. Implantation of BHK/hNGF cells decreased the overall extent of the lesion produced by QA. The attenuation of QA-induced toxicity was associated with a preservation of ChAT and NADPH-d-positive neurons within the striatum. Associated with the histological protection produced by hNGF was a significant attenuation of apomorphine-induced rotational behavior.

EXAMPLE 23

Treatment of Neural Degeneration in Non-Human Primates using Encapsulated Genetically Modified BHK Cells In this example we grafted BHK cells into the lateral ventricle of fornix-transected nonhuman primates and assessed the ability of polymer encapsulated NGF-secreting cells to prevent the degeneration of primate cholinergic basal forebrain neurons which normally occurs following axotomy.

BHK-hNGF Cell Line Production.

The BHK-hNGF cell line was produced as described in Example 22.

Encapsulation Procedure

BHK-hNGF cells were encapsulated as described in Example 22.

Surgical Procedures Young adult cynomolgus (Macaca fascicularis) monkeys of both sexes (N=8; 4–6 kg) were used in this study. Animals were tranquilized with ketamine HCL (10 mg/kg, im) and intravenous lines were secured for fluid administration. The animals were intubated via the orotracheal method and anesthesia maintained throughout the procedure with isoflurane (1.5–2.0%). Animals were placed on a heating pad to maintain body temperature and electrocardiogram leads placed to monitor heart rate and rhythm. To facilitate relaxation of the brain and minimize trauma due to retraction pressure, mannitol (0.250 mg/kg, iv) was administered immediately prior to the craniotomy.

Unilateral transections of the left fornix were performed using an open microsurgical approach developed by Kordower and Fiandaca (1990). After securing the animals in a Kopf stereotoxic headframe, a midline incision was made in the scalp and the skin retracted laterally. The medial attachment of the temporalis muscle was mobilized and a surgical drill used to create a parasagittal bone flap (size=1.5 cm×4.0 cm) which exposed the frontal superior sagittal sinus. The dura was retracted and a self-retaining retractor used to expose the interhemispheric fissure. The parasagittal bridging veins were coagulated where needed to facilitate retraction of the cerebral hemisphere. With the aid of a surgical microscope, arachnoid adhesions were divided. When necessary, veins overlying the corpus callosum were coagulated. The corpus callosum was longitudinally incised exposing medial subcortical structures from the septum and head of the caudate rostrally through the foramen of Monro caudally. At the level of the foramen of Monro, the fornix is easily visualized as a discrete 2–3 mm wide white fiber bundle. The fornix was initially transected using a ball dissector then the cut ends of the fornix were suctioned to ensure completeness of the lesion.

Following the transection of the fornix, individual BHK cell-containing capsules were manually placed within the lateral ventricle with fine forceps between the head of the caudate and the septal nucleus. A total of 5 capsules were implanted in each animal oriented in a row in the rostro-caudal direction. The capsules abutted the caudate and septum, remained upright, and did not require to be secured further. Four animals received BHK/hNGF capsules, three received BHK control cell-loaded capsules and one monkey received a fornix transection but no transplant. With hemostasis achieved, the dura was reapproximated, the bone flap was sutured back in place and the galea and skin was sutured using routine methods. All animals received antibiotics (Cefotaxime, 50 mg/kg, IM) for 4 days postoperatively.

Histology

Twenty-three to twenty-eight days following surgery, animals were anesthetized as described above. Two-three ml of CSF was obtained from either the lumbar region (N=1 BHK control; 2 BHK/hNGF) or cisterna magna (N=2 BHK control; 2 BHK/hNGF) to assay hNGF levels. Animals were then placed into the stereotoxic frame, the previously prepared bone flap was removed, the cerebral hemisphere retracted and the BHK cell-loaded capsules removed. Immediately following removal of the capsules, animals were transcardially perfumed using a peristaltic pump with 1 liter of phosphate-buffered saline (pH=7.4) containing 1 ml of Heparin followed fixation with 3.5 lifers of 4% paraformaldehyde. The brains were blocked in the transverse plane following fixation, stored in 25% buffered sucrose (pH 7.4) and refrigerated for 5–7 days.

Frozen sections were cut (30 μm) on a sliding knife microtome and every seventh section through the septal/diagonal band complex was processed immunocytochemically for choline acetyltransferase (CHAT) and the low affinity p75 NGF receptor (NGFr). Immunocytochemical labeling was conducted according to previously published protocols and briefly consisted of: 1) overnight incubation in PBS containing 0.4% Triton+2% normal serum, 2) 48 hour incubation in the primary CHAT polyclonal antibody (Chemicon; 1:10,000), or NGFR monoclonal antibody (generously provided by Dr. Mark Bothwell; 1:20,000), 3) overnight rinse in PBS+0.2% Triton, 4) 6×5 minute rinse in PBS followed by a 1.5 hour incubation in the appropriate biotinylated secondary IgG antibody (Vector; 1:100), 5) 6×5 minute rinses in PBS+Triton, 6) incubation with "Elite" Avidin-Biotin complex (Vector, 1:1000) for 1.5 hours, 7) 3×10 minutes rinses in PBS, 8) incubation in the chromagen solution containing 0.05% 3,3' diaminobenzidine, 2.5% nickel ammonium sulfate dissolved in 0.1% Tris buffer for 5 minutes followed by hydrogen peroxide (0.01%) for 5 minutes. The reaction was terminated by 3×1 minute rinses in PBS. Sections were mounted, dehydrated in alcohols and coverslipped. Control sections were processed in an identical manner except the primary antibody solvent or an irrelevant IgG was substituted for the primary antibody. Adjacent sections were stained with hematoxylin and eosin (H & E) to aid in cytoarchitectonic delineation.

To verify the completeness of the lesion, sections through the hippocampus were processed histochemically for the visualization of acetylcholinesterase (AChE) using the procedure of Hedreen and coworkers ( ). Sections were incubated for 1 hour in a solution (pH 5.0) containing 100 mM sodium acetate (65ml), 50 mg acetythiocholine iodide, 100 mm sodium citrate (5 ml) 30 mm copper sulfate (10 ml), 15 ml dH20, 5 mM potassium ferricyanide (4 ml) and 0.001M tetraisopropylpyrophophoramide (iso-OMPA). After 3×10 minute washes in sodium acetate buffer, the sections were incubated for 1 minute in 4% ammonium sulfide. After 5×10 minute washes in sodium nitrite, the section were incubated for 1 minute in a 0.05% silver nitrate solution. After 5×10 minute washes in sodium nitrate, sections were mounted, dehydrated, and coverslipped as before. For control, sections were processed in an identical manner except that acetylthiocholine iodide was omitted from the incubation medium.

For quantification of cholinergic cell loss, the number of ChAT and NGFr-positive neurons were manually counted within the medial septum (MS) and vertical limb of the diagonal band (VLDB) at a total magnification of 10×. ChAT-positive neurons on the midline were excluded from this analysis. Representative sections (4 per brain) located approximately 200 $\mu$M from each animal were used for this analysis. For statistical analysis, the numbers of neurons ipsilateral to the lesion were expressed as percentages of neurons contralateral to the lesion. Student's t test was used to determine differences between the BHK-control and BHK-hNGF groups.

NGF-induced Neurite Outgrowth

Conditioned media (CM) from encapsulated BHK-control and BHK-hNGF cells was passed thru a 0.2 $\mu$m filter and added to PC12A cells grown on standard tissue culture 6 or 24 well plates at a concentration of 200,000 cells/ml to test for the presence of hNGF in the CM. All medium conditioning and neurite outgrowth assays were performed in 5% $CO_2$ and at 37° C. As a positive control, 2.5S mouse NGF was added to some of the wells to induce neuritic extensions (50 ng/ml). The PC12A cells were scored for neurite processes that were $\geq 3$ times the length of the cell body diameter after a period of 1–4 days. In addition, the rate of neurite induction, and the stability of the neurites was observed and a comparison was made between the culture conditions.

NGF ELISA

Quantification of hNGF released from both encapsulated BHK-hNGF cells was performed as described in Example 22.

Results

The BHK cell-loaded devices were retrieved from the lateral ventricles 23–28 days following implantation with little to no host tissue adhering to the capsules. The level of hNGF produced by the capsules prior to implantation was 21.4±2.0 ng/capsule/24 hr and 8.3+1.2 ng/capsule/24 hr in the retrieved capsules. The BHK-control capsules produced no detectable hNGF.

The BHK-hNGF cell-loaded devices were left in situ in 1 of the BHK-control animals for fixation to demonstrate placement of the devices and observe the host tissue response. All capsules were placed within the lateral ventricle and abutted both the head of the caudate and the lateral septum. The host response to these capsules was excellent, with little evidence of immune cells surrounding the capsules. A proliferation of small to moderate sized blood vessels and a mild gliotic response was observed around the capsules particularly at the interface between adjacent capsules.

In retrieved capsules containing BHK-hNGF cells, few adhering host cells were found on the capsule wall and a large number of viable BHK cells, evenly distributed at high density, were present within the polymeric device. Numerous mitotic figures were observed throughout all of the cell-loaded capsules. Morphologic analysis of H & E-stained acrylate sections revealed that encapsulated cell survival was equivalent between the control and BHK-hNGF cell-loaded capsules.

In all animals, histological examination revealed that the left fornix was completely transected while the contralateral fornix remained intact. The completeness of the lesion was verified by demonstrating that within the hippocampus ipsilateral to the lesion there was a profound reduction in AChE staining. Some remaining AChE-positive fibers were observed diffusely distributed within the lesioned hippocampus and little reduction of staining was observed within the inner third of the molecular layer of the dentate gyrus.

No differences in the extent of the fornix lesion or the loss of cholinergic neurons were observed between the animal that received no transplant and those receiving control BHK cells. Accordingly, the data from these groups were combined. In these animals, a significant reduction was observed in the number of cholinergic neurons ipsilateral to the lesion. NGFr-positive neurons were decreased 54% within the MS and 30% within the VLDB compared to the intact side. The loss of ChAT-positive neurons paralleled the loss of NGFr labeled neurons and was 53% within the MS and 21% within the VLDB. While many surviving cholinergic neurons ipsilateral to the lesion appeared normal, others appeared shrunken, pale and dystrophic. In contrast, BHK-NGF transplants resulted in a significant attenuation of the loss of cholinergic neurons following fornix transection. Analysis of NGFr-positive neurons revealed a modest loss neurons within the MS (19%) and VLDB (7%).

Similarly, ChAT-immunoreactive neurons in NGF-treated animals were decreased only 20% in the MS and 7% in the VLDB. Cholinergic neurons in the NGF-treated animals were generally larger and appeared to be more intensely labeled than those in the BHK-control animals. Sections through the septum of the NGF-treated animals revealed a dense sprouting of cholinergic fibers within the septum in both the ChAT and NGFr preparations. These fibers ramified against the ependyinal lining of the ventricle adjacent to the transplant site and were particularly prominent within the dorsolateral quadrant of the septum corresponding to the normal course of the fornix. This sprouting of cholinergic fibers was not observed in animals receiving BHK-control implants. Despite the prevention of the loss of cholinergic neurons and induction of sprouting of these same neurons, hNGF was not detectable (limit of detection equals 25 pg) within CSF taken from either lumbar and cisterna magna taps.

These findings support use of polymer-encapsulated cell therapy in treating neurodegenerative diseases such as Alzheimer's disease where basal forebrain degeneration is a consistent pathological feature.

EXAMPLE 24

Treatment of Neural Degeneration in Aged Non-Human Primates using Encapsulated Genetically Modified BHK Cells Many mammalian species, including humans, are known to undergo neuronal loss as a natural consequence of the aging process. Aged non-human primates were used in this experiment to evaluate whether aged neurons would respond to growth factors in a manner similar to neurons in younger animals. Fimbria fornix lesions were performed in aged non-human primates according to the method described in example 23. The encapsulated cells, surgical procedure and analytical methods were the same as reported in example 23. The animals used in these studies were 24–29 year old Rhesus monkeys. Similar protection of cholinergic basal forebrain neurons to that observed in example 23 was also obtained in these older animals.

EXAMPLE 25

Delivery of a Putative Parkinson's Factor (GDNF) into the Rat CNS using Encapsulated BHK Cells Parkinson's disease is a progressive neurodegererative disorder of unknown etiology in which midbrain dopaminergic neurons are gradually lost, leading to movement disorders and eventually death. A growth factor, glial cell line-derived neurotrophic factor, (GDNF) has been described that exhibits an apparent trophic activity for midbrain dopaminergic neurons in vitro (Lin et al., Science, 260, p. 1130 (1993)). These experiments evaluated the in vivo effect on dopaminergic function of delivery of rGDNF using encapsulated genetically modified BHK cells.

PCR Cloning of GDNF

Reverse transcription—PCR was performed on total RNA extracted from E18 rat brain. The PCR primers that were used were synthesized based on the published sequence (Lin et al., Science, 260, pp. 1130 (1993)) for cloning into the pNUT expression vector (Baetge et al. Proc. Natl. Acad. Sci., 83, pp. 5454–58 (1986)).

The cDNA was subcloned into the pNUT vector and restriction digests were done to determine insert orientation. A sense and antisense clone were selected and then prepared for transfection. A modified calcium phosphate transfection method was used to introduce the expression vectors into BHK cells. The cells were then selected in methotrexate for 6–8 weeks to amplify the vector and the gene expression.

Cell Culture

The BHK cells were cultured in standard cell cultured medium containing fetal bovine serum. Conditioned medium was obtained by adding a defined, serum-free medium to both the sense and antisense BHK cell lines for 48 hours. The primary mesencephalic tissues were dissected from E15 rat fetuses and enzymatically dissociated and plated in 24 well plates (Nunc) in a serum-free, defined medium (Hycor) and incubated at 37° C. and 5% CO2. To assess the potential of the GDNF to enhance tyrosine hydrosine hydroxylase (TH) neuron survival, various amounts of the conditioned medium from both cell lines was added in separate wells to the mesencephalic cultures for up to 3 weeks.

Dopaminergic neuron survival was assayed by staining the cultures for TH after treatment for 1, 2 or 3 weeks. Immunocytochemistry was performed using a mouse monoclonal antibody for TH (IncStar) followed by detection with a Vector Mouse ELITE kit and visualized using diaminobenzidine. Cell counts of TH-positive neurons was done using an inverted microscope with bright field optics.

In general, the TH+ neurons in the cultures treated with the rGDNF exhibit an increased arborization of processes, increased TH immunoreactivity and in general a more robust appearance.

GDNF MRNA and protein expression was verified in the BHK-rGDNF(sense) cell line using Northern blot analysis and with a primary ventral mesencephalic neuronal bioassay for dopaminergic neuron survival (TH-positive).

To determine whether rGDNF has any effect on dopaminergic function in vivo, both cell lines (sense or antisense) or untransfected BHK cells were encapsulated in immunoisolatory polymeric devices and implanted unilaterally into the striatum of normal Lewis rats. In those animals receiving rGDNF, behavioral alterations including movement asymmetries were detected after a 1–2 mg/kg dose of amphetamine. No such asymmetry was seen in the control animals.

A repeated measures analysis of variance was conducted including cell type, and with amphetamine dose and turning direction included as repeated measures. Rats were more active with increasing doses of amphetamine, the main effect of amphetamine dose was statistically significant, $F(2,32)=36.90$, $p=0.0001$. The main effect of movement direction was also significant, $F(1,6)=19.81$, $p=0.0004$. This asymmetry in movement direction increased as the drug dose increased, the drug dose by turning direction interaction was statistically significant, $F(2,32)=8.43$, $p=0.001$, and the movement asymmetry was significantly larger in the rats receiving encapsulated GDNF-transfected bHK cells than in the rats receiving the encapsulated non-transfected bHK cells, the movement direction by cell type interaction was statistically significant, $F(1,16)=24.74$, $p=0.0001$. It should be noted that the direction of the movement asymmetry in the rats implanted with encapsulated GDNF-transfected BHK cells was such that they moved more in the direction contralateral to the implant than in the direction ipsilateral to the implant.

What is claimed is:

1. A method of forming an implantable and retrievable immunoisolatory vehicle, the method comprising the steps of:
   (a) forming a jacket of biocompatible thermoplastic or hydrogel, and
   (b) loading said jacket with a core comprising a volume of at least 1 $\mu$l and at least $10^4$ cells capable of secreting a biologically active product or biocompatible matrix comprising a hydrogel, said jacket having a molecular weight cutoff permitting passage of molecules thereacross to provide said biologically active product of said function.

2. The method of claim 1 in which said jacket is formed of a hydrogel.

3. The method of claim 2 in which said jacket hydrogel comprises alginate.

4. The method of claim 1 in which said jacket is formed of a thermoplastic.

5. A method of forming an implantable and retrievable immunoisolatory vehicle, the method comprising the steps of:
   (a) forming a jacket of biocompatible thermoplastic or hydrogel, and
   (b) loading said jacket with a core comprising a volume of at least 1 $\mu$l and at least $10^4$ cells capable of secreting a biologically active product or providing a metabolic or immunologic function, said cells being dispersed in a biocompatible matrix comprising extracellular matrix components, said jacket having a molecular weight cutoff permitting passage of molecules thereacross to provide said biologically active product or said function.

6. The method of claim 5 in which said jacket is formed of a hydrogel.

7. The method of claim 5 in which said jacket comprises alginate.

8. The method of claim 5 in which said jacket is formed of a thermoplastic.

9. The method of claim 5 wherein the jacket is selected from the group consisting of polyacrylonitrile-polyvinylchloride, polyacrylonitrile, polymethylmethacrylate, polyvinyldifluoride, polyolefins, polysulfones and celluloses.

10. The method of claim 1 or 5 wherein the jacket further comprises a hydropilic or hydrophobic additive.

11. The method of claim 1 wherein the core matrix is selected from the group consisting of alginate, collagen, laminin containing hydrogels, agarose, cellulose, methylcellulose, block copolymer of ethyl ethylene-vinylalcohol, sodium polystyrene sulfonate, vinyl-methyl-tribenzyl ammonium chloride, phosphazene, and polyvinylalcohol.

12. The method of claim 5 wherein the core matrix is selected from the group consisting of collagen, laminin, glycoaminoglycans, proteoglycans, fibronectin, clastin, and mixtures thereof.

13. The method of claim 12 wherein the glycosaminoglycans are selected from the group consisting of hyaluronic acid, chondroitin sulfate, heparin, and heparin sulfate.

14. The method of claim 1 or 5 wherein the biologically active product is selected from the group consisting of antibodies, enzymes, trophic factors, growth factors, hormones, biological response modifiers, cytokines, lymphokine and neurotransmitters.

15. The method of claim 1 or 5 wherein the biologically active product is selected from the group consisting of enkephalins, catecholamines, opioid peptides, and mixtures thereof.

16. The method of claim 1 or 5 wherein accessory cells are coisolated with the cells in the core.

17. The method of claim 1 or 5 wherein the cells are primary cells.

18. The method of claim 1 or 5 wherein the cells are selected from the group consisting of insulin-producing cells, adrenal chromaffin cells, antibody-secreting cells, fibroblasts, astrocytes, Beta cell lines, and Chinese hamster ovary cells.

19. The method of claim 1 or 5 wherein the cells are neural stem cells.

20. The method of claim 1 or 5 wherein the cells are adrenal chromaffin cells.

21. The method of claim 1 or 5 wherein the core has a volume in excess of 10 $\mu$l.

22. The method of claim 1 or 5 wherein the jacket is between 5 and 200 $\mu$m thick.

23. The method of claim 1 or 5 wherein the jacket has a molecular weight cutoff between 50 kD and 2000 kD.

24. The method of claim 1 or 5 wherein the jacket is shaped to form a hollow fiber.

25. The method of claim 1 or 5 wherein the jacket is shaped to form a flat sheet.

* * * * *